US008957023B2

(12) United States Patent
Cox

(10) Patent No.: US 8,957,023 B2
(45) Date of Patent: Feb. 17, 2015

(54) METHODS FOR MAKING PROTEINS CONTAINING FREE CYSTEINE RESIDUES

(75) Inventor: George N. Cox, Louisville, CO (US)

(73) Assignee: Bolder Biotechnology Inc., Boulder, CO (US)

( * ) Notice: Subject to any disclaimer, the term of this patent is extended or adjusted under 35 U.S.C. 154(b) by 0 days.

(21) Appl. No.: 13/616,608

(22) Filed: Sep. 14, 2012

(65) Prior Publication Data
US 2013/0217629 A1 Aug. 22, 2013

Related U.S. Application Data

(60) Continuation of application No. 13/088,830, filed on Apr. 18, 2011, now Pat. No. 8,288,126, which is a continuation-in-part of application No. 12/604,165, filed on Oct. 22, 2009, now Pat. No. 7,947,655, which is a continuation-in-part of application No. 10/857,644, filed on May 27, 2004, now Pat. No. 7,629,314, which is a division of application No. 09/889,273, filed as application No. PCT/US00/00931 on Jan. 14, 2000, now Pat. No. 6,753,165.

(60) Provisional application No. 60/116,041, filed on Jan. 14, 1999.

(51) Int. Cl.
*A61K 38/27* (2006.01)
*A61K 47/48* (2006.01)
*C07K 1/113* (2006.01)
*C07K 14/505* (2006.01)
*C07K 14/56* (2006.01)
*C07K 14/61* (2006.01)
*C07K 14/72* (2006.01)
*C12P 21/02* (2006.01)

(52) U.S. Cl.
CPC ............ *A61K 38/27* (2013.01); *A61K 47/48215* (2013.01); *C07K 1/1133* (2013.01); *C07K 14/505* (2013.01); *C07K 14/56* (2013.01); *C07K 14/61* (2013.01); *C07K 14/72* (2013.01); *C12P 21/02* (2013.01)
USPC ...................................................... 514/11.4

(58) Field of Classification Search
CPC ........ C07K 14/61; C07K 38/27; C07K 47/48; C07K 47/48215
See application file for complete search history.

(56) References Cited

U.S. PATENT DOCUMENTS

| 4,588,585 | A | 5/1986  | Mark et al.       |
|-----------|---|---------|-------------------|
| 4,636,463 | A | 1/1987  | Altman et al.     |
| 4,678,751 | A | 7/1987  | Goeddel           |
| 4,738,844 | A | 4/1988  | Bell et al.       |
| 4,751,077 | A | 6/1988  | Bell et al.       |
| 4,810,643 | A | 3/1989  | Souza             |
| 4,855,238 | A | 8/1989  | Gray et al.       |
| 4,904,584 | A | 2/1990  | Shaw              |
| 4,921,699 | A | 5/1990  | DeChiara et al.   |
| 4,929,554 | A | 5/1990  | Goeddel et al.    |
| 5,096,705 | A | 3/1992  | Goeddel et al.    |
| 5,153,265 | A | 10/1992 | Shadle et al.     |
| 5,162,111 | A | 11/1992 | Grabstein et al.  |
| 5,166,322 | A | 11/1992 | Shaw et al.       |
| 5,178,855 | A | 1/1993  | Bonnem            |
| 5,206,344 | A | 4/1993  | Katre et al.      |
| 5,208,158 | A | 5/1993  | Bech et al.       |
| 5,214,132 | A | 5/1993  | Kuga et al.       |
| 5,223,407 | A | 6/1993  | Wong et al.       |
| 5,229,496 | A | 7/1993  | Deeley et al.     |
| 5,382,657 | A | 1/1995  | Karasiewicz et al.|
| 5,391,485 | A | 2/1995  | Deeley et al.     |
| 5,393,870 | A | 2/1995  | Deeley et al.     |
| 5,441,734 | A | 8/1995  | Reichert et al.   |
| 5,574,137 | A | 11/1996 | Gray et al.       |
| 5,578,301 | A | 11/1996 | Myers             |
| 5,582,824 | A | 12/1996 | Goeddel et al.    |
| 5,595,888 | A | 1/1997  | Gray et al.       |
| 5,602,007 | A | 2/1997  | Dunn et al.       |
| 5,629,283 | A | 5/1997  | Nicola et al.     |
| 5,681,720 | A | 10/1997 | Kuga et al.       |
| 5,690,925 | A | 11/1997 | Gray et al.       |
| 5,710,027 | A | 1/1998  | Hauptmann et al.  |
| 5,720,952 | A | 2/1998  | Clark et al.      |
| 5,766,897 | A | 6/1998  | Braxton           |
| 5,824,778 | A | 10/1998 | Ishikawa et al.   |
| 5,824,784 | A | 10/1998 | Kinstler et al.   |
| 5,849,535 | A | 12/1998 | Cunningham et al. |
| 5,891,429 | A | 4/1999  | Clark et al.      |

(Continued)

FOREIGN PATENT DOCUMENTS

| CA | 2066370 | 4/1996  |
|----|---------|---------|
| CA | 2287521 | 10/1998 |

(Continued)

OTHER PUBLICATIONS

Abdel-Meguide et al., "Three dimensional structure of a genetically engineered variant of porcine growth hormone," 1987, PNAS, vol. 84, pp. 6434-6437.
Alberts et al., "The birth, assembly and death of proteins," Chapter 5 in Molecular Biology of the Cell, Third Edition, Garland Publishing, Inc. New York, NY, 1994, ISBN 0-8153-1619-4, pp. 212-216.
Barton et al., "Identification of Three Distinct Receptor Binding Sites of Murine Interleukin-11," The Journal of Biological Chemistry, Feb. 1999, vol. 274(9), pp. 5755-5761.
Bazan et al., "Unraveling the Structure of IL-2," Science, Jul. 1992, vol. 257(5068), pp. 410-413.

(Continued)

*Primary Examiner* — Marianne P Allen
(74) *Attorney, Agent, or Firm* — Sheridan Ross P.C.

(57) ABSTRACT

The present invention relates to novel methods of making soluble proteins having free cysteines in which a host cell is exposed to a cysteine blocking agent. The soluble proteins produced by the methods can then be modified to increase their effectiveness. Such modifications include attaching a PEG moiety to form pegylated proteins.

30 Claims, 1 Drawing Sheet

(56) References Cited

U.S. PATENT DOCUMENTS

| | | |
|---|---|---|
| 5,895,646 A | 4/1999 | Wang |
| 5,908,621 A | 6/1999 | Glue et al. |
| 5,908,763 A | 6/1999 | Clark et al. |
| 5,916,773 A | 6/1999 | Mele et al. |
| 5,942,221 A | 8/1999 | Clark et al. |
| 6,042,822 A | 3/2000 | Gilbert et al. |
| 6,171,824 B1 | 1/2001 | Todaro et al. |
| 6,177,074 B1 | 1/2001 | Glue et al. |
| 6,250,469 B1 | 6/2001 | Kline |
| 6,287,557 B1 | 9/2001 | Boursnell et al. |
| 6,323,006 B1 | 11/2001 | Peregrino Ferreira et al. |
| 6,362,162 B1 | 3/2002 | Rybak et al. |
| 6,461,605 B1 | 10/2002 | Cutler et al. |
| 6,472,373 B1 | 10/2002 | Albrecht |
| 6,497,871 B1 | 12/2002 | Gray et al. |
| 6,514,729 B1 | 2/2003 | Bentzien |
| 6,524,570 B1 | 2/2003 | Glue et al. |
| 6,531,122 B1 | 3/2003 | Pedersen et al. |
| 6,608,183 B1 | 8/2003 | Cox, III |
| 6,632,426 B2 | 10/2003 | Osslund |
| 6,753,165 B1 | 6/2004 | Cox et al. |
| 6,780,613 B1 | 8/2004 | Wells et al. |
| 6,800,740 B1 | 10/2004 | Cunningham et al. |
| 6,809,178 B2 | 10/2004 | Evans et al. |
| 7,038,015 B2 | 5/2006 | Jensen |
| 7,148,333 B2 | 12/2006 | Cox, III |
| 7,153,943 B2 | 12/2006 | Cox, III et al. |
| 7,214,779 B2 | 5/2007 | Cox, III |
| 7,232,885 B2 | 6/2007 | Cox, III |
| 7,253,267 B2 | 8/2007 | Cox, III |
| 7,270,809 B2 | 9/2007 | Cox, III |
| 7,306,931 B2 | 12/2007 | Rosendahl et al. |
| 7,309,781 B2 | 12/2007 | Cox, III |
| 7,314,921 B2 | 1/2008 | Cox, III |
| 7,345,149 B2 | 3/2008 | Cox, III |
| 7,345,154 B2 | 3/2008 | Cox, III |
| 7,399,839 B2 | 7/2008 | Cox et al. |
| 7,495,087 B2 | 2/2009 | Cox, III |
| 7,560,101 B2 | 7/2009 | Cox, III |
| 7,629,314 B2 | 12/2009 | Cox, III |
| 7,732,572 B2 | 6/2010 | Cox, III |
| 7,795,396 B2 | 9/2010 | Cox, III |
| 7,824,669 B2 | 11/2010 | Cox et al. |
| 7,947,655 B2 | 5/2011 | Cox, III et al. |
| 7,959,909 B2 | 6/2011 | Cox, III |
| 7,964,184 B2 | 6/2011 | Cox, III |
| 7,994,124 B2 | 8/2011 | Cox, III |
| 8,133,480 B2 | 3/2012 | Cox, III |
| 8,288,126 B2 | 10/2012 | Cox, III |
| 2003/0166865 A1 | 9/2003 | Cox, III |
| 2004/0136955 A1 | 7/2004 | Barker et al. |
| 2008/0076706 A1 | 3/2008 | Cox, III |
| 2009/0060863 A1 | 3/2009 | Cox, III |
| 2009/0269804 A1 | 10/2009 | Rosendahl et al. |
| 2011/0172151 A1 | 7/2011 | Cox, III et al. |
| 2011/0250169 A1 | 10/2011 | Cox, III |
| 2012/0231040 A1 | 9/2012 | Cox, III |

FOREIGN PATENT DOCUMENTS

| | | |
|---|---|---|
| EP | 0185459 | 6/1986 |
| EP | 0243153 | 10/1987 |
| EP | 0312358 | 4/1989 |
| EP | 0355460 | 2/1990 |
| EP | 0458064 | 11/1991 |
| EP | 0612846 | 8/1994 |
| EP | 0668354 | 8/1995 |
| JP | 02-234692 | 9/1990 |
| JP | 04-164098 | 9/1992 |
| JP | 04-507099 | 12/1992 |
| JP | 5-268983 | 10/1993 |
| JP | 6-510904 | 12/1994 |
| JP | 9-503396 | 4/1997 |
| JP | 10-507080 | 7/1998 |
| JP | 04-504801 | 2/2004 |
| WO | WO 86/05804 | 10/1986 |
| WO | WO 87/01132 | 2/1987 |
| WO | WO 89/10964 | 11/1989 |
| WO | WO 90/12874 | 11/1990 |
| WO | WO 90/13310 | 11/1990 |
| WO | WO 93/00109 | 1/1993 |
| WO | WO 93/06217 | 4/1993 |
| WO | WO 94/01453 | 1/1994 |
| WO | WO 94/12219 | 6/1994 |
| WO | WO 94/12638 | 6/1994 |
| WO | WO 94/12639 | 6/1994 |
| WO | WO 94/22466 | 10/1994 |
| WO | WO 95/11987 | 5/1995 |
| WO | WO 95/32003 | 11/1995 |
| WO | WO 95/34326 | 12/1995 |
| WO | WO 96/04385 | 2/1996 |
| WO | WO 96/11949 | 4/1996 |
| WO | WO 96/31537 | 10/1996 |
| WO | WO 96/36362 | 11/1996 |
| WO | WO 97/11370 | 3/1997 |
| WO | WO 97/41887 | 11/1997 |
| WO | WO 98/25971 | 6/1998 |
| WO | WO 98/37200 | 8/1998 |
| WO | WO 99/03887 | 1/1999 |
| WO | WO 00/42175 | 7/2000 |
| WO | WO 01/87925 | 11/2001 |
| WO | WO 02/44717 | 6/2002 |

OTHER PUBLICATIONS

Bazan, "Haemopoietic receptors and helical cytokines," Immunology Today, 1990, vol. 11, pp. 350-354.

Beilharz et al., "Antiviral and Antiproliferative Activities of Interferon-α1: The Role of Cysteine Residues," J. Interferon Res., 1986, vol. 6, pp. 677-685.

Benhar et al. "*Pseudomonas* exotoxin A mutants. Replacement of surface-exposed residues in domain III with cysteine residues that can be modified with polyethylene glycol in a site-specific manner." Journal of Biological Chemistry, May 1994, vol. 269, No. 18, pp. 13398-13404.

Bill et al., "Expression and mutagenesis of recombinant human and murine erythropoietins in *Escherichia coli*," Biochimica et Biophysica Acta, 1995, vol. 1261, pp. 34-43.

Bittorf et al., "Structural and functional characterisation of recombinant human erythropoietin analogues," Febs. Lett., 1993, vol. 366, pp. 133-136.

Black, RJ, "Animal Studies of Prophylaxis," Am. J. Med., 1997, vol. 102, pp. 39-44.

Boissel et al., "Erythropoietin Structure-Function Relationships," J. Biol. Chem., 1993, vol. 268(21), pp. 15983-15993.

Bowie et al., "Deciphering the Message in Protein Sequences: Tolerance to Amino Acid Substitutions," Science, Mar. 1999, vol. 247(4948), pp. 1306-1310.

Campbell et al., "Pegylated peptides: V. Carboxy-terminal PEGylated analogs of growth hormone-releasing factor (GRF) display enhanced duration of biological activity in vivo," J Peptide Res, Jun. 1997, vol. 49, pp. 527-537.

Cantrell et al., "Cloning, sequence, and expression of a human granulocyte/macrophage colony-stimulating factor," Proceedings of the National Academy of Sciences, USA, 1985, vol. 82(18), pp. 6250-6254.

Caron et al., "Engineered humanized dimeric forms of IgG are more effective antibodies," J Exp Med, Oct. 1992, vol. 176(4), pp. 1191-1195.

Chang et al., "High level of secretion of human growth hormone by *E. coli*," Gene, 1987, vol. 55, pp. 189-196.

Cheetham et al., "NMR structure of human erythropoietin and a comparison with its receptor bound conformation," Nat. Structural Biol., 1998, vol. 5, pp. 861-866.

Cheetham et al., "Structure-function studies of human interferons-α: enhanced activity on human and murine cells," Antiviral Research, 1991, vol. 15, pp. 27-39.

Chen et al., "Construction, properties and specific fluorescent labeling of a bovine prothrombin mutant engineered with a free C-terminal cysteine," Protein Engr., 1996, vol. 9(6), pp. 545-533.

(56) References Cited

OTHER PUBLICATIONS

Chene et al., "Crystallization of the Complex of Human IFN-gamma and the Extracellular Domain of the IFN-gamma Receptor," Proteins: Structure, Function, and Genetics, 1995, vol. 23, pp. 591-594.
Chern et al., "Structural role of amino acids 99-110 in recombinant human erythropoietin," European Journal of Biochemistry, Dec. 1991, vol. 202(2), pp. 225-229.
Clark et al., "Long-acting Growth Hormones Produced by Conjugation with Polyethylene Glycol," J. Biol. Chem., 1996, vol. 271(36), pp. 21969-21977.
Clark-Lewis et al., "Structure-function studies of human granulocyte-macrophage colony-stimulating factor. Identification of residues required for activity," Journal of Immunology, Aug. 1988, vol. 141(3), pp. 881-889.
Cosenza et al., "Disulfide Bond Assignment in Human Interleukin-7 by Matrix-assisted Laser Desorption/Ionization Mass Spectroscopy and Site-directed Cysteine to Serine Mutational Analysis," The Journal of Biological Chemistry, Dec. 26, 1997, vol. 272(52), pp. 32995-33000.
Cox et al., "A long acting mono-pegylated human growth hormone analog is a potent stimulator of weight gain and bone growth in hypophysectiomized rates," Endocrinology, 2007, vol. 148(4), pp. 1590-1597.
Cunningham et al., "High-Resolution Epitope Mapping of hGH-Receptor Interactions by Alanine-Scanning Mutagenesis," Science, 1989, vol. 244, pp. 1081-1085.
Cunningham et al., "Receptor and Antibody Epitopes in Human Growth Hormone Identified by Homolog-Scanning Mutagenesis," Science, 1989, vol. 243, pp. 1330-1336.
Czupryn et al., "Alanine-scanning Mutagenesis of Human Interleukin-11: Identification of Regions Important for Biological Activity," Annals of the New York Academy of Sciences, Jul. 1995, vol. 762, pp. 152-164.
Czupryn et al., "Structure-Function Relationships in Human Interleukin-11," Journal of Biological Chemistry, Jan. 1995, vol. 270(2), pp. 978-985.
Dechiara et al., "Procedures for in Vitro DNA Mutagenesis of Human Leukocyte Interferon Sequences," Methods in Enzymology, 1986, vol. 119(58), pp. 403-415.
DeVos et al., "Human Growth Hormone and Extracellular Domain of Its Receptor: Crystal Structure of the Complex," Science, vol. 255, Jan. 17, 1992, pp. 306-312.
Diederichs et al., "Novel fold and putative receptor binding site of granulocyte-macrophage colony-stimulating factor," Science, 1991, vol. 254(5039), pp. 1779-1782.
Dube et al., "Glycosylation at Specific Sites of Erythropoietin Is Essential for Biosynthesis, Secretion, and Biological Function," The Journal of Biol. Chem., 1988, vol. 263(33), pp. 17516-17521.
"Dulbecco's Modified Eagle's Medium/Ham's Nutrient Mixture F12," product information, SAFC Biosciences, Inc., 2006, 2 pages.
Ealick et al. "Three-dimensional structure of recombinant human interferon-gamma," Science, May 3, 1991, vol. 252(5006), pp. 698-702.
Edge et al., "Interferon Analogues from Synthetic Genes: An Approach to Protein Structure-Activity Studies," Interferon, 1986, vol. 7, pp. 1-46.
Elliot et al., "Mapping of the Active Site of Recombinant Human Erythropoietin," Blood, 1997, vol. 89, pp. 493-502.
Evinger et al., "Recombinant Human Leukocyte Interferon Produced in Bacteria Has Antiproliferative Activity," J. Biol. Chem., 1981, vol. 256(5), pp. 2113-2114.
Fibi et al., "Evidence for the Location of the Receptor-Binding Site of Human Erythropoietin at the Carboxyl-Terminal Domain," Blood, Mar. 15, 1991, vol. 77(6), pp. 1203-1210.
Fujii et al., "Structure of KW-2228, a tailored human granulocyte colony-stimulating factor with enhanced biological activity and stability," FEBS Lett, 1997, vol. 410, pp. 131-135.
Ganser et al., "The effect of recombinant human granulocyte-macrophage colony-stimulating factor on neutropenia and related morbidity in chronic severe neutropenia," Annals of Internal Medicine, Dec. 1989, vol. 111(11), pp. 887-892.
Goodson et al., "Site-Directeed Pegylation of Recombinant Interleukin-2 at its Glycosylation Site," Bio/Technology, 1990, vol. 8, pp. 343-346.
Goodwin et al., "Human interleukin 7: Molecular cloning and growth factor activity on human and murine B-lineage cells," Proc. Natl. Acad. Sci. USA, Jan. 1989, vol. 86, pp. 302-306.
Grodberg et al., "Alanine scanning mutagenesis of human erythropoietin identifies four amino acids which are critical for biological activity," European Journal of Biochemistry, 1993, vol. 218(2), pp. 597-601.
Harmegnies et al., "Characterization of a potent human interleukin-11 agonist," Biochemical Journal, 2003, vol. 375, pp. 23-32.
Hill et al., "The structure of granulocyte-colony-stimulating factor and its relationship to other growth factors," Proc. Natl. Acad. Sci. USA, 1993, vol. 90, pp. 5167-5171.
Hsiung et al., "High level of expression, efficient ad folding of human growth hormone E. coli," Bio/Technology, 1986, vol. 4, pp. 991-995.
Hu et al., "Human IFN-α Protein Engineering: The Amino Acid Residues at Positions 86 and 90 Are Important for Antiproliferative Activity," Journal of Immunology, 2001, 167, pp. 1482-1489.
Ishikawa et al., "The Substitution of Cysteine 17 of Recombinant Human G-CSF with Alanine Greatly Enhanced its Stability," Cell Structure and Function, 1992, vol. 17(1), pp. 61-65.
Karpusas et al., "The crystal structure of human interferon β at 2.2-Å resolution," Proc. Natl. Acad. Sci. USA, 1997, vol. 94, pp. 11813-11818.
Karpusas et al., "The structure of human interferon-beta: implications for activity," Cell. Mol. Life sci., 1998, vol. 54, pp. 1203-1216.
Kawashima et al., "Molecular cloning of cDNA encoding adipogenesis inhibitory factor and identity with interleukin-11," FEBS Letters, Jun. 1991, vol. 283(2), pp. 199-202.
Kinstler et al. "Mono-N-terminal poly(ethylene glycol)-protein conjugates," Advanced Drug Delivery Reviews, Jun. 2002, vol. 54, No. 4, pp. 477-485.
Knulsi et al., "Polyethylene glycol (PEG) modification of granulocyte-macrophage colony stimulating factor (GM-CSF) enhances neutrophil priming activity but not colony stimulating activity," British Journal of Haematology, 1992, vol. 82(4), pp. 654-663.
Kroemer et al., "Prediction of three-dimensional structure of IL-7 by homology modeling," Protein Engineering, 1996, vol. 9, pp. 493-498.
Kuan et al. "*Pseudomonas* exotoxin A mutants. Replacement of surface exposed residues in domain II with cysteine residues that can be modified with polyethylene glycol in a site-specific manner." Journal of Biological Chemistry, Mar. 1994, vol. 269, No. 10, pp. 7610-7616.
Kuga et al., "Mutagenesis of human granulocyte colony stimulating factor," Biochem Biophys Res Commun, 1989, vol. 159, pp. 103-111.
Lee et al., "Isolation of cDNA for a human granulocyte-macrophage colony-stimulating factor by functional expression in mammalian cells," Proceedings of the National Academy of Sciences, USA, 1985, vol. 82(13), pp. 4360-4364.
Lin et al., "Cloning and expression of the human erythropoietin gene," Proceedings of the National Academy of Sciences, USA, Nov. 1985, vol. 82(22), pp. 7580-7584.
Lowman and Wells, "Affinity Maturation of Human Growth Hormone by Monovalent Phage Display," J. Mol. Biol., 1993, vol. 234, pp. 564-578.
Lydon et al., "Immunochemical Mapping of α-2 Interferon," Biochemistry, 1985, vol. 24, pp. 4131-4141.
Matthews et al., "A sequential dimerization mechanism for erythropoietin receptor activation," PNAS, 1996, vol. 93, pp. 9471-9476.
McElroy et al., "Structural and Biophysical Studies of the Human IL-7/IL-7Rα Complex," Structure, 2009, vol. 17(1), pp. 54-65, NIH Public Acess Author Manuscript, 25 pages.
Miyadi et al., "Importance of the Carboxy-terminus of Human Interleukin-11 in Conserving Its Biological Activity," Bioscience, biotechnology, and biochemistry, Mar. 1996, vol. 60(3), pp. 541-542.

(56) References Cited

OTHER PUBLICATIONS

Mori et al., "Recombinant human granulocyte-macrophage colony-stimulating factor (rhGM-CSF) and rhG-CSF in the treatment of a child with severe chronic neutropenia," Blood, Nov. 1994, vol. 84(9), pp. 3244-3245.
Mott and Campbell, "Four-helix bundle growth factors and their receptors: protein-protein interactions," Curr Opin Struct Biol, 1995, vol. 5, pp. 114-121.
Nagata, S., "Granulocyte Colony Stimulating Factor and its Receptor," Chapter 20 of Cytokine Handbook, Angus W. Thomson, ed., Academic Press, Harcourt Brace & Company, 1994, pp. 371-385.
Nielson et al., "Erythropoietin-beta-D-galactosidase. The generation, purification and use of a fusion protein," Journal of Immunological Methods, Jun. 1988, vol. 111(1), pp. 1-9.
Nisbet et al., "Single Amino Acid Substitutions at Conserved Residues of Human Interferon-α Can Effect Antiviral Specific Activity," Biochem. Int., 1985, vol. 11, pp. 301-309.
Olins et al., "Saturation muatgenesis of human interleukin-3," Journal of Biological Chemistry, Oct. 1995, vol. 270(40), pp. 23754-23760.
Paul et al., "Molecular cloning of a cDNA encoding interleukin 11, a stromal cell-derived lymphonpoietic and hematopoietic cytokine," Proceedings of the National Academy of Sciences, USA, Oct. 1990, vol. 87(19), pp. 7512-7516.
Petoukov et al., "Addition of Missing Loops and Domains to Protein Models by X-Ray Solution Scattering," Biophys. J., 2002, vol. 83, pp. 3113-3125.
Quelle et al., "Phosphorylatable and epitope-tagged human erythropoietins: utility and purification of native baculovirus-derived forms," Protein Expr Purif, Dec. 1992, vol. 3(6), pp. 461-469.
Radhakrishnan et al., "Zinc mediated dimer of human interferon-α2b revealed by X-ray crystallography," Structure, 1996, vol. 4(12), pp. 1453-1463.
Rozwarski et al., "Refined crystal structure and mutagenesis of human granulocyte-macrophage colony-stimulating factor," Proteins, Nov. 1996, vol. 26(3), pp. 304-313.
Senda et al., "Refined crystal structure of recombinant murine interferon-beta at 2.15 A resolution," J. Mol. Biol., 1995, vol. 253, pp. 187-207.
Shanafelt et al., "Identification of critical regions in mouse granulocyte-macrophage colony-stimulating factor by scanning-deletion analysis," Proceedings of the National Academy of Sciences, USA, 1989, vol. 86, pp. 4872-4876.
Sprang et al., "Cytokine structural taxonomy and mechanisms of receptor engagement," Curr. Opin. Struct. Biol., 1993, vol. 3, pp. 815-827.
Syed et al., "Efficiency of sinalling through ecytokine receptors depends critically on receptor orientation," Nature, 1998, vol. 395, pp. 511-516.
Sytkowski et al., "Human erythropoietin dimers with markedly enhance in vivo activity," Proc. Nat. Acad. Sci. USA, 1998, vol. 95, pp. 1184-1188.
Sytkowski et al., "Immunoshemical studies of human erythropoietin using site-specific anti-peptide antibodies," Journal of Biological Chemistry, 1987, vol. 262(3), pp. 1161-1165.
Tacken et al., "Definition of receptor binding sites on human interleukin-11 by molecular modeling-guided mutagenesis," European Journal of Biochemistry, Oct. 1999, vol. 265(2), pp. 645-655.
Takahashi et al., "Beneficial Effect of Brewers' Yeast Extract on Daily Activity in a Murine Model of Chronic Fatigue Syndrome," Advance Access Publication, eCAM, Jan. 23, 2006, vol. 3(1), pp. 109-115.
Takahashi et al., "Short stature caused by a mutant growth hormone with an antagonistic effect," Endocr J., Oct. 1996, vol. 43, Suppl:S27-32.
Tanaka et al., "Pharmacokinetics of Recombinant Human Granulocyte Colony-stimulating Factor Conjugated to Polyethylene Glycol in Rats," Cancer Research, 1991, vol. 51, pp. 3710-3714.
Tang et al., "Studies on the PEGylation of Protein at a Specific Site: Sulfhydryl-PEGylation of 97Cys-IFN-gamma," Sheng Wu Hua Xue Yu Sheng Wu Wu Li Xue Bao (Shanghai), 1996, vol. 28(3), pp. 312-315 (Abstract only).
Tiebel et al., "Conformational changes necessary for gene regulation by Tet repressor assayed by reversible disulfide bond formation," The EMBO Journal, Sep. 1998, vol. 17(17), pp. 5112-5119.
Tymms et al., "Functional significance of amino acid residues within conserved hydrophilic regions in human interferons-α," Antiviral Res., 1989, vol. 12, pp. 37-47.
Valenzuela et al., "Is Sequence Conservation in Interferons Due to Selection for Functional Proteins," Nature, Feb. 1985, vol. 313(21), pp. 698-700.
Walter et al., "Crystal structure of a complex between interferon-gamma and its soluble high-affinity receptor," Nature, 2000, vol. 376, pp. 230-235.
Walter et al., "Crystal Structure of Interleukin 10 Reveals and Interferon γ-like fold," Biochemistry, 1995, vol. 34, pp. 12118-12125.
Walter et al., "Three-dimensional structure of recombinant human granulocyte-macrophage colony-stimulating factor," J. Mol. Biol., 1992, vol. 224, pp. 1075-1085.
Wang et al., "Engineering and use of (32)P-labeled human recombinant interleukin-11 for receptor binding studies," Eur. J. Biochem., 2002, vol. 269, pp. 61-68.
Watson, Molecular Biology of the gene, Third Edition, Benjamin, eds., 1977, ISBN 0-8053-9609-8, p. 337.
Weich et al., "Interleukin-3/erythropoietin fusion proteins: in vitro effects on hematopoietic cells," Experimental Hematology, May 1993, vol. 21(5), pp. 647-655.
Wells, "Additivity of Mutational Effects in Proteins," Biochemistry, Sep. 1990, vol. 29(37), pp. 8509-8517.
Wells, "Hematopoietic Receptor Complexes," Ann. Rev. Biochem., 1996, vol. 65, pp. 609-634.
Wen et al., "Erythropoietin Structure-Function Relationships," The Journal of Biol. Chem., 1994, vol. 269(36), pp. 22839-22846.
Wojchowski et al., "Biotinylated Recombinant Human Erythropoietins: Bioactivity and Utility as Receptor Ligand," Blood, Aug. 15, 1989, vol. 74(3), pp. 952-958.
Yamasaki et al., "Effect of Divalent Polyethylene Glycol Units, Conjugated on Human Granulocyte Colony-Stimulating Factor, on Biological Activities in vitro and in Vivo," Drugs Exptl.Clin. Res., 1998, vol. 24(4), pp. 191-196.
Youngster et al. "Structure, biology, and therapeutic implications of pegylated interferon alpha-2b," Current Pharmaceutical Design, Nov. 2002, vol. 8, No. 24, pp. 2139-2157.
Zalipsky, "Chemistry of polyethylene glycol conjugates with biologically active molecules," Adv. Drug Delivery Reviews, 1995, vol. 16, pp. 157-182.
Zhang et al., "Characterization of asparagine deamidation and aspartate isomerization in recombinant human interleukin-11," Pharmaceutical Research, Aug. 2002, vol. 19(8), pp. 1223-1231.
Zurawaki et al., "Definition and spatial location of mouse interleukin-2 residues that interact with the heterotrimeric receptor," Embo Journal, 1993, vol. 12, pp. 5113-5119.
Opposition to European Patent Application No. EP 00902412.6, filed by Bayer Intellectual Property GmbH and Bayer HealthCare LLC dated Jun. 27, 2012, 21 pages.
European Search Report for European Patent Application No. 10012486.6, dated Feb. 7, 2011.
International Search Report for International (PCT) Patent Application No. PCT/US00/00931, mailed Apr. 26, 2000.
Written Opinon for International (PCT) Patent Application No. PCT/US00/00931, Feb. 16, 2001.
International Preliminary Examination Report for International (PCT) Patent Application No. PCT/US00/00931, mailed Jun. 19, 2001.
Hurley et al., "Translating tissue culture results into animal models: the case of *Salmonella typhimurium*," Trends in Microbiology, 2003, vol. 11, No. 12, pp. 562-569.
Inoue et al., "The role of interferon-β in the treatment of multiple sclerosis and experimental autoimmune encephalomyelitis—in the perspective of inflammasomes," Immunology, 2013, vol. 139, Iss. 1, pp. 11-18.
Van Holten et al., "Interferon-β for treatment of rheumatoid arthritis?," Arthritis Research, 2002, vol. 4, No. 6, pp. 346-352.

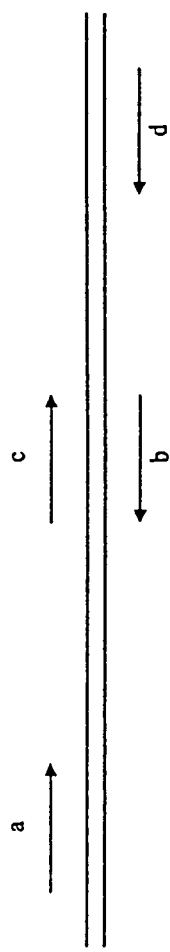

SEQUENCE LISTING

```
<160> NUMBER OF SEQ ID NOS: 87

<210> SEQ ID NO 1
<211> LENGTH: 39
<212> TYPE: DNA
<213> ORGANISM: artificial sequence
<220> FEATURE:
<223> OTHER INFORMATION: primer

<400> SEQUENCE: 1
ccccggatcc gccaccatgg atctctggca gctgctgtt                              39

<210> SEQ ID NO 2
<211> LENGTH: 40
<212> TYPE: DNA
<213> ORGANISM: artificial sequence
<220> FEATURE:
<223> OTHER INFORMATION: primer

<400> SEQUENCE: 2
ccccgtcgac tctagagcca ttagatacaa agctcttggg                             40

<210> SEQ ID NO 3
<211> LENGTH: 39
<212> TYPE: DNA
<213> ORGANISM: artificial sequence
<220> FEATURE:
<223> OTHER INFORMATION: primer

<400> SEQUENCE: 3 ggggtcgac catatgttcc caaccattcc cttatccag                               39

<210> SEQ ID NO 4
<211> LENGTH: 33
<212> TYPE: DNA
<213> ORGANISM: artificial sequence
<220> FEATURE:
<223> OTHER INFORMATION: primer

<400> SEQUENCE: 4 ggggatcct cactagaagc cacagctgcc ctc                                     33

<210> SEQ ID NO 5
<211> LENGTH: 32
<212> TYPE: DNA
<213> ORGANISM: artificial sequence
<220> FEATURE:
```

<223> OTHER INFORMATION: primer

<400> SEQUENCE: 5
cgcggatccg attagaatcc acagctcccc tc                                32

<210> SEQ ID NO 6
<211> LENGTH: 65
<212> TYPE: DNA
<213> ORGANISM: artificial sequence
<220> FEATURE:
<223> OTHER INFORMATION: primer

<400> SEQUENCE: 6
gcatctatgt tcgttttctc tatcgctacc aacgcttacg cattcccaac cattcccttta   60 tccag                                                              65

<210> SEQ ID NO 7
<211> LENGTH: 66
<212> TYPE: DNA
<213> ORGANISM: artificial sequence
<220> FEATURE:
<223> OTHER INFORMATION: primer

<400> SEQUENCE: 7 cccctctag acatatgaag aagaacatcg cattcctgct ggcatctatg ttcgttttct    60
ctatcg                                                             66

<210> SEQ ID NO 8
<211> LENGTH: 62
<212> TYPE: DNA
<213> ORGANISM: artificial sequence
<220> FEATURE:
<223> OTHER INFORMATION: primer

<400> SEQUENCE: 8
gcagtggcac tggctggttt cgctaccgta gcgcaggcct tcccaaccat tcccttatcc   60
ag                                                                 62

<210> SEQ ID NO 9
<211> LENGTH: 59
<212> TYPE: DNA
<213> ORGANISM: artificial sequence
<220> FEATURE:
<223> OTHER INFORMATION: primer

<400> SEQUENCE: 9
ccccgtcgac acatatgaag aagacagcta tcgcgattgc agtggcactg gctggtttc    59

<210> SEQ ID NO 10
<211> LENGTH: 36
<212> TYPE: DNA
<213> ORGANISM: artificial sequence
<220> FEATURE:
<223> OTHER INFORMATION: primer

<400> SEQUENCE: 10
ctgcttgaag atctgcccac accgggggct gccatc                             36

<210> SEQ ID NO 11
<211> LENGTH: 24
<212> TYPE: DNA
<213> ORGANISM: artificial sequence
<220> FEATURE:
<223> OTHER INFORMATION: primer

```
<400> SEQUENCE: 11
gtagcgcagg ccttcccaac catt                                              24

<210> SEQ ID NO 12
<211> LENGTH: 39
<212> TYPE: DNA
<213> ORGANISM: artificial sequence
<220> FEATURE:
<223> OTHER INFORMATION: primer

<400> SEQUENCE: 12
ctgcttgaag atctgcccag tccgggggca gccatcttc                              39

<210> SEQ ID NO 13
<211> LENGTH: 51
<212> TYPE: DNA
<213> ORGANISM: artificial sequence
<220> FEATURE:
<223> OTHER INFORMATION: primer

<400> SEQUENCE: 13
gggcagatct tcaagcagac ctacagcaag ttcgactgca actcacacaa c                51

<210> SEQ ID NO 14
<211> LENGTH: 34
<212> TYPE: DNA
<213> ORGANISM: artificial sequence
<220> FEATURE:
<223> OTHER INFORMATION: primer

<400> SEQUENCE: 14
cgcggtaccc gggatccgat tagaatccac agct                                   34

<210> SEQ ID NO 15
<211> LENGTH: 36
<212> TYPE: DNA
<213> ORGANISM: artificial sequence
<220> FEATURE:
<223> OTHER INFORMATION: primer

<400> SEQUENCE: 15
gggcagatct tcaagcagac ctactgcaag ttcgac                                 36

<210> SEQ ID NO 16
<211> LENGTH: 42
<212> TYPE: DNA
<213> ORGANISM: artificial sequence
<220> FEATURE:
<223> OTHER INFORMATION: primer

<400> SEQUENCE: 16
cgcggtaccg gatccttagc agaagccaca gctgccctcc ac                          42

<210> SEQ ID NO 17
<211> LENGTH: 36
<212> TYPE: DNA
<213> ORGANISM: artificial sequence
<220> FEATURE:
<223> OTHER INFORMATION: primer

<400> SEQUENCE: 17
gtcagaggcg ccgtacacca ggcagttggc gaagac                                 36

<210> SEQ ID NO 18
```

<211> LENGTH: 42
<212> TYPE: DNA
<213> ORGANISM: artificial sequence
<220> FEATURE:
<223> OTHER INFORMATION: primer

<400> SEQUENCE: 18
gtcagaggcg ccgtacacca ggctgttgca gaagacactc ct          42

<210> SEQ ID NO 19
<211> LENGTH: 54
<212> TYPE: DNA
<213> ORGANISM: artificial sequence
<220> FEATURE:
<223> OTHER INFORMATION: primer

<400> SEQUENCE: 19
gcgctgcagg aatgaatact tctgttcctt tgggatatag cattcttcaa actc          54

<210> SEQ ID NO 20
<211> LENGTH: 66
<212> TYPE: DNA
<213> ORGANISM: artificial sequence
<220> FEATURE:
<223> OTHER INFORMATION: primer

<400> SEQUENCE: 20 cccccctctag acatatgaag aagaacatcg cattcctgct ggcatctatg ttcgttttct          60
ctatcg          66

<210> SEQ ID NO 21
<211> LENGTH: 33
<212> TYPE: DNA
<213> ORGANISM: artificial sequence
<220> FEATURE:
<223> OTHER INFORMATION: primer

<400> SEQUENCE: 21
gcgctgcagg aagcaatact tctgttcctt tgg          33

<210> SEQ ID NO 22
<211> LENGTH: 65
<212> TYPE: DNA
<213> ORGANISM: artificial sequence
<220> FEATURE:
<223> OTHER INFORMATION: primer

<400> SEQUENCE: 22
gcatctatgt tcgttttctc tatcgctacc aacgcttacg cattcccatg cattcccta          60 tccag          65

<210> SEQ ID NO 23
<211> LENGTH: 33
<212> TYPE: DNA
<213> ORGANISM: artificial sequence
<220> FEATURE:
<223> OTHER INFORMATION: primer

<400> SEQUENCE: 23
agcctggtgt acggctgctc tgacagcaac gtc          33

<210> SEQ ID NO 24
<211> LENGTH: 33
<212> TYPE: DNA
<213> ORGANISM: artificial sequence

```
<220> FEATURE:
<223> OTHER INFORMATION: primer

<400> SEQUENCE: 24
gacgttgctg tcagagcagc cgtacaccag gct                                33

<210> SEQ ID NO 25
<211> LENGTH: 31
<212> TYPE: DNA
<213> ORGANISM: artificial sequence
<220> FEATURE:
<223> OTHER INFORMATION: primer

<400> SEQUENCE: 25
cccggatcca tgggggtgca cgaatgtcct g                                  31

<210> SEQ ID NO 26
<211> LENGTH: 31
<212> TYPE: DNA
<213> ORGANISM: artificial sequence
<220> FEATURE:
<223> OTHER INFORMATION: primer

<400> SEQUENCE: 26
cccgaattct atgcccaggt ggacacacct g                                  31

<210> SEQ ID NO 27
<211> LENGTH: 8
<212> TYPE: PRT
<213> ORGANISM: Artificial sequence
<220> FEATURE:
<223> OTHER INFORMATION: synthetic peptide

<400> SEQUENCE: 27

Asp Tyr Lys Asp Asp Asp Asp Lys
1               5

<210> SEQ ID NO 28
<211> LENGTH: 7
<212> TYPE: PRT
<213> ORGANISM: Artificial sequence
<220> FEATURE:
<223> OTHER INFORMATION: synthetic peptide

<400> SEQUENCE: 28

Ser Gly Gly Ser Gly Gly Ser
1               5

<210> SEQ ID NO 29
<211> LENGTH: 33
<212> TYPE: DNA
<213> ORGANISM: artificial sequence
<220> FEATURE:
<223> OTHER INFORMATION: primer

<400> SEQUENCE: 29
cgcggatcca aaatgggggt gcacgaatgt cct                                33

<210> SEQ ID NO 30
<211> LENGTH: 51
<212> TYPE: DNA
<213> ORGANISM: artificial sequence
<220> FEATURE:
<223> OTHER INFORMATION: primer

<400> SEQUENCE: 30
```
gtctttgtag tccgagcctc cgcttccgcc cgatctgtcc cctgtcctgc a    51

<210> SEQ ID NO 31
<211> LENGTH: 45
<212> TYPE: DNA
<213> ORGANISM: artificial sequence
<220> FEATURE:
<223> OTHER INFORMATION: primer

<400> SEQUENCE: 31
cgcgaattct tatttatcgt catcgtcttt gtagtccgag cctcc    45

<210> SEQ ID NO 32
<211> LENGTH: 39
<212> TYPE: DNA
<213> ORGANISM: artificial sequence
<220> FEATURE:
<223> OTHER INFORMATION: primer

<400> SEQUENCE: 32
gaggccaagg aggccgagtg tatcacgacg ggctgtgct    39

<210> SEQ ID NO 33
<211> LENGTH: 31
<212> TYPE: DNA
<213> ORGANISM: artificial sequence
<220> FEATURE:
<223> OTHER INFORMATION: primer

<400> SEQUENCE: 33
cccgaattct ggtggatatg cccaggtgga c    31

<210> SEQ ID NO 34
<211> LENGTH: 38
<212> TYPE: DNA
<213> ORGANISM: artificial sequence
<220> FEATURE:
<223> OTHER INFORMATION: primer

<400> SEQUENCE: 34
gaggccaagg aggccgagaa atctgtacgg gctgtgct    38

<210> SEQ ID NO 35
<211> LENGTH: 31
<212> TYPE: DNA
<213> ORGANISM: artificial sequence
<220> FEATURE:
<223> OTHER INFORMATION: primer

<400> SEQUENCE: 35
cccggatcca tgggggtgca cgaatgtcct g    31

<210> SEQ ID NO 36
<211> LENGTH: 33
<212> TYPE: DNA
<213> ORGANISM: artificial sequence
<220> FEATURE:
<223> OTHER INFORMATION: primer

<400> SEQUENCE: 36
agcttgaatg agtgtatcac tgtcccagac acc    33

<210> SEQ ID NO 37
<211> LENGTH: 33
<212> TYPE: DNA
<213> ORGANISM: artificial sequence
<220> FEATURE:
<223> OTHER INFORMATION: primer

<400> SEQUENCE: 37
ggtgtctggg acagtgatac actcattcaa gct                          33

<210> SEQ ID NO 38
<211> LENGTH: 33
<212> TYPE: DNA
<213> ORGANISM: artificial sequence
<220> FEATURE:
<223> OTHER INFORMATION: primer

<400> SEQUENCE: 38
agcttgaatg agaatatctg tgtcccagac acc                          33

<210> SEQ ID NO 39
<211> LENGTH: 33
<212> TYPE: DNA
<213> ORGANISM: artificial sequence
<220> FEATURE:
<223> OTHER INFORMATION: primer

<400> SEQUENCE: 39
ggtgtctggg acacagatat tctcattcaa gct                          33

<210> SEQ ID NO 40
<211> LENGTH: 39
<212> TYPE: DNA
<213> ORGANISM: artificial sequence
<220> FEATURE:
<223> OTHER INFORMATION: primer

<400> SEQUENCE: 40
gccctgttgg tctgctcttc ccagccgtgg gagcccctg                    39

<210> SEQ ID NO 41
<211> LENGTH: 39
<212> TYPE: DNA
<213> ORGANISM: artificial sequence
<220> FEATURE:
<223> OTHER INFORMATION: primer

<400> SEQUENCE: 41
caggggctcc cacggctggg aagagcagac caacagggc                    39

<210> SEQ ID NO 42
<211> LENGTH: 39
<212> TYPE: DNA
<213> ORGANISM: artificial sequence
<220> FEATURE:
<223> OTHER INFORMATION: primer

<400> SEQUENCE: 42
gccctgttgg tcaactcttg ccagccgtgg gagcccctg                    39

<210> SEQ ID NO 43
<211> LENGTH: 39
<212> TYPE: DNA
<213> ORGANISM: artificial sequence
<220> FEATURE:
<223> OTHER INFORMATION: primer

<400> SEQUENCE: 43
caggggctcc cacggctggc aagagttgac caacagggc                    39

```
<210> SEQ ID NO 44
<211> LENGTH: 27
<212> TYPE: DNA
<213> ORGANISM: artificial sequence
<220> FEATURE:
<223> OTHER INFORMATION: primer

<400> SEQUENCE: 44
ccagatgcgg cctgtgctgc tccactc                                27

<210> SEQ ID NO 45
<211> LENGTH: 27
<212> TYPE: DNA
<213> ORGANISM: artificial sequence
<220> FEATURE:
<223> OTHER INFORMATION: primer

<400> SEQUENCE: 45
gagtggagca gcacaggccg catctgg                                27

<210> SEQ ID NO 46
<211> LENGTH: 51
<212> TYPE: DNA
<213> ORGANISM: artificial sequence
<220> FEATURE:
<223> OTHER INFORMATION: primer

<400> SEQUENCE: 46
tttgtagtcc gagcctccgc ttccgcccga acatctgtcc cctgtcctgc a     51

<210> SEQ ID NO 47
<211> LENGTH: 36
<212> TYPE: DNA
<213> ORGANISM: artificial sequence
<220> FEATURE:
<223> OTHER INFORMATION: primer

<400> SEQUENCE: 47
cgcggatccg ccaccatggg ggtgcacgaa tgtcct                      36

<210> SEQ ID NO 48
<211> LENGTH: 33
<212> TYPE: DNA
<213> ORGANISM: artificial sequence
<220> FEATURE:
<223> OTHER INFORMATION: primer

<400> SEQUENCE: 48
cgcgaattct catctgtccc ctgtcctgca gcc                         33

<210> SEQ ID NO 49
<211> LENGTH: 36
<212> TYPE: DNA
<213> ORGANISM: artificial sequence
<220> FEATURE:
<223> OTHER INFORMATION: primer

<400> SEQUENCE: 49
cgcgaattct caacatctgt ccctgtcct gcagcc                       36

<210> SEQ ID NO 50
<211> LENGTH: 33
<212> TYPE: DNA
<213> ORGANISM: artificial sequence
<220> FEATURE:
<223> OTHER INFORMATION: primer
```

<400> SEQUENCE: 50
cgcgaattcg gatatgtaaa tagatacaca gtg                                33

<210> SEQ ID NO 51
<211> LENGTH: 33
<212> TYPE: DNA
<213> ORGANISM: artificial sequence
<220> FEATURE:
<223> OTHER INFORMATION: primer

<400> SEQUENCE: 51
cgcaagctta aaagatttaa atcgtgtcat ggt                                33

<210> SEQ ID NO 52
<211> LENGTH: 66
<212> TYPE: DNA
<213> ORGANISM: artificial sequence
<220> FEATURE:
<223> OTHER INFORMATION: primer

<400> SEQUENCE: 52
cgcaagcttc atatgtgtga tctgcctcaa acccacagcc tgggttctag aaggaccttg    60
atgctc                                                             66

<210> SEQ ID NO 53
<211> LENGTH: 69
<212> TYPE: DNA
<213> ORGANISM: artificial sequence
<220> FEATURE:
<223> OTHER INFORMATION: primer

<400> SEQUENCE: 53
cgcgaattct tattccttac ttcttaaact ttcttgcaag tttgtcgaca aagaaaagga    60
tctcatgat                                                          69

<210> SEQ ID NO 54
<211> LENGTH: 66
<212> TYPE: DNA
<213> ORGANISM: artificial sequence
<220> FEATURE:
<223> OTHER INFORMATION: primer

<400> SEQUENCE: 54
gcatctatgt tcgttttctc tatcgctacc aacgcttacg catgtgatct gcctcaaacc    60
cacagc                                                             66

<210> SEQ ID NO 55
<211> LENGTH: 22
<212> TYPE: DNA
<213> ORGANISM: artificial sequence
<220> FEATURE:
<223> OTHER INFORMATION: primer

<400> SEQUENCE: 55
ctatgcggca tcagagcaga ta                                            22

<210> SEQ ID NO 56
<211> LENGTH: 22
<212> TYPE: DNA
<213> ORGANISM: artificial sequence
<220> FEATURE:
<223> OTHER INFORMATION: primer -continued

<400> SEQUENCE: 56
tgtggaattg tgagcggata ac                                           22

<210> SEQ ID NO 57
<211> LENGTH: 27
<212> TYPE: DNA
<213> ORGANISM: artificial sequence
<220> FEATURE:
<223> OTHER INFORMATION: primer

<400> SEQUENCE: 57
tgtgatctgc cttgtaccca cagcctg                                      27

<210> SEQ ID NO 58
<211> LENGTH: 27
<212> TYPE: DNA
<213> ORGANISM: artificial sequence
<220> FEATURE:
<223> OTHER INFORMATION: primer

<400> SEQUENCE: 58
caggctgtgg gtacaaggca gatcaca                                      27

<210> SEQ ID NO 59
<211> LENGTH: 21
<212> TYPE: DNA
<213> ORGANISM: artificial sequence
<220> FEATURE:
<223> OTHER INFORMATION: primer

<400> SEQUENCE: 59
aggcagatca gatgcgtaag c                                            21

<210> SEQ ID NO 60
<211> LENGTH: 21
<212> TYPE: DNA
<213> ORGANISM: artificial sequence
<220> FEATURE:
<223> OTHER INFORMATION: primer

<400> SEQUENCE: 60
gcttacgcat ctgatctgcc t                                            21

<210> SEQ ID NO 61
<211> LENGTH: 27
<212> TYPE: DNA
<213> ORGANISM: artificial sequence
<220> FEATURE:
<223> OTHER INFORMATION: primer

<400> SEQUENCE: 61
cttttggaac tggcagccaa actcctc                                      27

<210> SEQ ID NO 62
<211> LENGTH: 27
<212> TYPE: DNA
<213> ORGANISM: artificial sequence
<220> FEATURE:
<223> OTHER INFORMATION: primer

<400> SEQUENCE: 62
gaggagtttg gctgccagtt ccaaaag                                      27

<210> SEQ ID NO 63
<211> LENGTH: 27

-continued

```
<212> TYPE: DNA
<213> ORGANISM: artificial sequence
<220> FEATURE:
<223> OTHER INFORMATION: primer

<400> SEQUENCE: 63
ttcagccttt tggcactggt tgccaaa                                         27

<210> SEQ ID NO 64
<211> LENGTH: 27
<212> TYPE: DNA
<213> ORGANISM: artificial sequence
<220> FEATURE:
<223> OTHER INFORMATION: primer

<400> SEQUENCE: 64
tttggcaacc agtgccaaaa ggctgaa                                         27

<210> SEQ ID NO 65
<211> LENGTH: 27
<212> TYPE: DNA
<213> ORGANISM: artificial sequence
<220> FEATURE:
<223> OTHER INFORMATION: primer

<400> SEQUENCE: 65
ttcagccttt tggcactggt tgccaaa                                         27

<210> SEQ ID NO 66
<211> LENGTH: 27
<212> TYPE: DNA
<213> ORGANISM: artificial sequence
<220> FEATURE:
<223> OTHER INFORMATION: primer

<400> SEQUENCE: 66
tttggcaacc agtgccaaaa ggctgaa                                         27

<210> SEQ ID NO 67
<211> LENGTH: 27
<212> TYPE: DNA
<213> ORGANISM: artificial sequence
<220> FEATURE:
<223> OTHER INFORMATION: primer

<400> SEQUENCE: 67 agcctttttgg aaacagttgc caaactc                                        27

<210> SEQ ID NO 68
<211> LENGTH: 27
<212> TYPE: DNA
<213> ORGANISM: artificial sequence
<220> FEATURE:
<223> OTHER INFORMATION: primer

<400> SEQUENCE: 68
gagtttggca actgtttcca aaaggct                                         27

<210> SEQ ID NO 69
<211> LENGTH: 27
<212> TYPE: DNA
<213> ORGANISM: artificial sequence
<220> FEATURE:
<223> OTHER INFORMATION: primer

<400> SEQUENCE: 69
```
ggtttcagcc ttacagaact ggttgcc                                              27

<210> SEQ ID NO 70
<211> LENGTH: 27
<212> TYPE: DNA
<213> ORGANISM: artificial sequence
<220> FEATURE:
<223> OTHER INFORMATION: primer

<400> SEQUENCE: 70
ggcaaccagt tctgtaaggc tgaaacc                                              27

<210> SEQ ID NO 71
<211> LENGTH: 27
<212> TYPE: DNA
<213> ORGANISM: artificial sequence
<220> FEATURE:
<223> OTHER INFORMATION: primer

<400> SEQUENCE: 71
agggatggtt tcacactttt ggaactg                                              27

<210> SEQ ID NO 72
<211> LENGTH: 27
<212> TYPE: DNA
<213> ORGANISM: artificial sequence
<220> FEATURE:
<223> OTHER INFORMATION: primer

<400> SEQUENCE: 72
cagttccaaa agtgtgaaac catccct                                              27

<210> SEQ ID NO 73
<211> LENGTH: 27
<212> TYPE: DNA
<213> ORGANISM: artificial sequence
<220> FEATURE:
<223> OTHER INFORMATION: primer

<400> SEQUENCE: 73
taggagggtc tcacaccaag cagcaga                                              27

<210> SEQ ID NO 74
<211> LENGTH: 27
<212> TYPE: DNA
<213> ORGANISM: artificial sequence
<220> FEATURE:
<223> OTHER INFORMATION: primer

<400> SEQUENCE: 74
tctgctgctt ggtgtgagac cctccta                                              27

<210> SEQ ID NO 75
<211> LENGTH: 27
<212> TYPE: DNA
<213> ORGANISM: artificial sequence
<220> FEATURE:
<223> OTHER INFORMATION: primer

<400> SEQUENCE: 75
caggggagtc tcacacaccc ccacccc                                              27

<210> SEQ ID NO 76
<211> LENGTH: 27
<212> TYPE: DNA
<213> ORGANISM: artificial sequence

```
<220> FEATURE:
<223> OTHER INFORMATION: primer

<400> SEQUENCE: 76
ggggtggggg tgtgtgagac tccctg                                    27

<210> SEQ ID NO 77
<211> LENGTH: 27
<212> TYPE: DNA
<213> ORGANISM: artificial sequence
<220> FEATURE:
<223> OTHER INFORMATION: primer

<400> SEQUENCE: 77
gcctgtgtga tatgtggggt gggggtg                                   27

<210> SEQ ID NO 78
<211> LENGTH: 27
<212> TYPE: DNA
<213> ORGANISM: artificial sequence
<220> FEATURE:
<223> OTHER INFORMATION: primer

<400> SEQUENCE: 78
cttcatcagg ggacactctg tcacccc                                   27

<210> SEQ ID NO 79
<211> LENGTH: 27
<212> TYPE: DNA
<213> ORGANISM: artificial sequence
<220> FEATURE:
<223> OTHER INFORMATION: primer

<400> SEQUENCE: 79
ggggtgacag agtgtcccct gatgaag                                   27

<210> SEQ ID NO 80
<211> LENGTH: 27
<212> TYPE: DNA
<213> ORGANISM: artificial sequence
<220> FEATURE:
<223> OTHER INFORMATION: primer

<400> SEQUENCE: 80
cacccccacc ccacatatca cacaggc                                   27

<210> SEQ ID NO 81
<211> LENGTH: 27
<212> TYPE: DNA
<213> ORGANISM: artificial sequence
<220> FEATURE:
<223> OTHER INFORMATION: primer

<400> SEQUENCE: 81
catcagggga gtacatgtca cccccac                                   27

<210> SEQ ID NO 82
<211> LENGTH: 27
<212> TYPE: DNA
<213> ORGANISM: artificial sequence
<220> FEATURE:
<223> OTHER INFORMATION: primer

<400> SEQUENCE: 82
gtgggggtga catgtactcc cctgatg                                   27
```

<210> SEQ ID NO 83
<211> LENGTH: 27
<212> TYPE: DNA
<213> ORGANISM: artificial sequence
<220> FEATURE:
<223> OTHER INFORMATION: primer

<400> SEQUENCE: 83
cccctgtatc acagaggctt ccaggtc                                    27

<210> SEQ ID NO 84
<211> LENGTH: 27
<212> TYPE: DNA
<213> ORGANISM: artificial sequence
<220> FEATURE:
<223> OTHER INFORMATION: primer

<400> SEQUENCE: 84
gacctggaag cctctgtgat acagggg                                    27

<210> SEQ ID NO 85
<211> LENGTH: 33
<212> TYPE: DNA
<213> ORGANISM: artificial sequence
<220> FEATURE:
<223> OTHER INFORMATION: primer

<400> SEQUENCE: 85
cgcgaattct tattccttac atcttaaact ttc                             33

<210> SEQ ID NO 86
<211> LENGTH: 36
<212> TYPE: DNA
<213> ORGANISM: artificial sequence
<220> FEATURE:
<223> OTHER INFORMATION: primer

<400> SEQUENCE: 86
cgcgaattct taacattcct tacttcttaa actttc                          36

<210> SEQ ID NO 87
<211> LENGTH: 30
<212> TYPE: DNA
<213> ORGANISM: artificial sequence
<220> FEATURE:
<223> OTHER INFORMATION: primer

<400> SEQUENCE: 87
cgcgaattct taacacttac ttcttaaact                                 30

METHODS FOR MAKING PROTEINS CONTAINING FREE CYSTEINE RESIDUES

CROSS REFERENCE TO RELATED APPLICATIONS

This application is a Continuation of U.S. application Ser. No. 13/088,830, filed Apr. 18, 2011, now U.S. Pat. No. 8,288,126, which is a Continuation-in-part of U.S. patent application Ser. No. 12/604,165, filed Oct. 22, 2009, now U.S. Pat. No. 7,947,655, which is a Continuation-in-part of U.S. patent application Ser. No. 10/857,644, filed on May 27, 2004, now U.S. Pat. No. 7,629,314, which is a Division of U.S. patent application Ser. No. 09/889,273, filed on Sep. 6, 2001, now U.S. Pat. No. 6,753,165, which is a national phase of International Patent Application No. PCT/US00/00931, filed Jan. 14, 2000, which claims the benefit of U.S. Provisional Patent Application No. 60/116,041, filed Jan. 14, 1999. Each of the above-identified patent applications is incorporated herein by reference in its entirety for all purposes.

GOVERNMENT SUPPORT

This invention was made with government support under Grant Nos., 1R43 CA079361 and 2R44 CA079361 awarded by the National Institutes of Health. The Government of the United States has certain rights in the invention.

REFERENCE TO A SEQUENCE LISTING

This application contains a Sequence Listing submitted electronically as a text file by EFS-Web. The text file, named "Sequence_Listing", has a size in bytes of 17 KB, and was recorded on Oct. 22, 2009. The information contained in the text file is incorporated herein by reference in its entirety pursuant to 37 CFR §1.52(e)(5).

FIELD OF THE INVENTION

The present invention relates generally to methods of making proteins and more specifically to recombinant proteins containing a "free" cysteine residue that does not form a disulfide bond.

BACKGROUND OF THE INVENTION

There is considerable interest on the part of patients and healthcare providers in the development of low cost, long-acting, "user-friendly" protein therapeutics. Proteins are expensive to manufacture and unlike conventional small molecule drugs, are usually not readily absorbed by the body. Moreover they are digested if taken orally. Therefore, proteins must typically be administered by injection. After injection most proteins are cleared rapidly from the body, necessitating frequent, often daily, injections. Patients dislike injections, which leads to reduced compliance and reduced drug efficacy. Some proteins such as erythropoietin (EPO) are effective when administered less often (three times per week for EPO) but this is due to the fact that the proteins are glycosylated. Glycosylation requires that the recombinant proteins be manufactured using mammalian cell expression systems, which is expensive and increases the cost of protein pharmaceuticals.

Thus, there is a strong need to develop protein delivery technologies that lower the costs of protein therapeutics to patients and healthcare providers. One solution to this problem is the development of methods to prolong the circulating half-lives of protein therapeutics in the body so that the proteins do not have to be injected frequently. This solution also satisfies the needs and desires of patients for protein therapeutics that are "user-friendly", i.e., protein therapeutics that do not require frequent injections.

Covalent modification of proteins with polyethylene glycol (PEG) has proven to be a useful method to extend the circulating half-lives of proteins in the body (Abuchowski et al., 1984; Hershfield, 1987; Meyers et al., 1991). Covalent attachment of PEG to a protein increases the protein's effective size and reduces its rate of clearance from the body. PEGs are commercially available in several sizes, allowing the circulating half-lives of PEG-modified proteins to be tailored for individual indications through use of different size PEGs. Other documented in vivo benefits of PEG modification are an increase in protein solubility, stability (possibly due to protection of the protein from proteases) and a decrease in protein immunogenicity (Katre et al., 1987; Katre, 1990).

One known method for PEGylating proteins uses compounds such as N-hydroxy succinimide (NHS)-PEG to attach PEG to free amines, typically at lysine residues or at the N-terminal amino acid. A major limitation of this approach is that proteins typically contain several lysines, in addition to the N-terminal amino acid, and the PEG moiety attaches to the protein non-specifically at any of the available free amines, resulting in a heterogeneous product mixture. Many NHS-PEGylated proteins are unsuitable for commercial use because of low specific activities and heterogeneity. Inactivation results from covalent modification of one or more lysine residues or the N-terminal amino acid required for biological activity or from covalent attachment of the PEG moiety near the active site of the protein.

Of particular relevance to this application is the finding that modification of human growth hormone (hGH) with amine-reactive reagents, including NHS-PEG reagents, reduces biological activity of the protein by more than 10-fold (Teh and Chapman, 1988; Clark et al., 1996). GH is a 22 kDa protein secreted by the pituitary gland. GH stimulates metabolism of bone, cartilage and muscle and is the body's primary hormone for stimulating somatic growth during childhood. Recombinant human GH (rhGH) is used to treat short stature resulting from GH inadequacy, Turner's Syndrome and renal failure in children. GH is not glycosylated and is fully active when produced in bacteria. The protein has a short in vivo half-life and must be administered by daily subcutaneous injection for maximum effectiveness (MacGillivray et al., 1996).

There is considerable interest in the development of long-acting forms of hGH. Attempts to create long-acting forms of hGH by PEGylating the protein with amine-reactive PEG reagents have met with limited success due to significant reductions in bioactivity upon PEGylation. Further, the protein becomes PEGylated at multiple sites (Clark et al., 1996). hGH contains nine lysines, in addition to the N-terminal amino acid. Certain of these lysines are located in regions of the protein known to be critical for receptor binding (Cunningham et al., 1989; Cunningham and Wells, 1989). Modification of these lysine residues significantly reduces receptor binding and bioactivity of the protein (de la Llosa et al., 1985; Martal et al., 1985; Teh and Chapman, 1988; Cunningham and Wells, 1989). hGH is readily modified by NHS-PEG reagents, but biological activity of the NHS-PEG protein is severely compromised, amounting to only 1% of wild type GH biological activity for a GH protein modified with five 5 kDa PEG molecules (Clark et al., 1996). The $EC_{50}$ for this multiply PEGylated GH protein is 440 ng/ml or approximately 20 nM (Clark et al., 1996). In addition to possessing significantly reduced biological activity, NHS-PEG-hGH is very heterogeneous due to different numbers of PEG molecules attached to the protein and at different amino acid residues, which has an impact on its usefulness as a potential therapeutic. Clark et al. (1996) showed that the circulating half-life of NHS-PEG-hGH in animals is significantly prolonged relative to non-modified GH. Despite possessing significantly reduced in vitro biological activity, NHS-PEG-hGH was effective and could be administered less often than non-modified hGH in a rat GH-deficiency model (Clark et al., 1996). However, high doses of NHS-PEG-hGH (60-180 μg per injection per rat) were required for efficacy in the animal models due to the low specific activity of the modified protein. There is a clear need for better methods to create PEGylated hGH proteins that retain greater bioactivity. There also is a need to develop methods for PEGylating hGH in a way that creates a homogeneous PEG-hGH product.

Biological activities of several other commercially important proteins are significantly reduced by amine-reactive PEG reagents. EPO contains several lysine residues that are critical for bioactivity of the protein (Boissel et al., 1993; Matthews et al., 1996) and modification of lysine residues in EPO results in near complete loss of biological activity (Wojchowski and Caslake, 1989). Covalent modification of alpha-interferon-2 with amine-reactive PEGs results in 40-75% loss of bioactivity (Goodson and Katre, 1990; Karasiewicz et al., 1995). Loss of biological activity is greatest with large (e.g., 10 kDa) PEGs (Karasiewicz et al., 1995). Covalent modification of G-CSF with amine-reactive PEGs results in greater than 60% loss of bioactivity (Tanaka et al., 1991). Extensive modification of IL-2 with amine-reactive PEGs results in greater than 90% loss of bioactivity (Goodson and Katre, 1990).

A second known method for PEGylating proteins covalently attaches PEG to cysteine residues using cysteine-reactive PEGs. A number of highly specific, cysteine-reactive PEGs with different reactive groups (e.g., maleimide, vinylsulfone) and different size PEGs (2-40 kDa) are commercially available. At neutral pH, these PEG reagents selectively attach to "free" cysteine residues, i.e., cysteine residues not involved in disulfide bonds. Cysteine residues in most proteins participate in disulfide bonds and are not available for PEGylation using cysteine-reactive PEGs. Through in vitro mutagenesis using recombinant DNA techniques, additional cysteine residues can be introduced anywhere into the protein. The newly added "free" cysteines can serve as sites for the specific attachment of a PEG molecule using cysteine-reactive PEGs. The added cysteine residue can be a substitution for an existing amino acid in a protein, added preceding the amino-terminus of the protein or after the carboxy-terminus of the protein, or inserted between two amino acids in the protein. Alternatively, one of two cysteines involved in a native disulfide bond may be deleted or substituted with another amino acid, leaving a native cysteine (the cysteine residue in the protein that normally would form a disulfide bond with the deleted or substituted cysteine residue) free and available for chemical modification. Preferably the amino acid substituted for the cysteine would be a neutral amino acid such as serine or alanine. Growth hormone has two disulfide bonds that can be reduced and alkylated with iodoacetimide without impairing biological activity (Bewley et al., (1969). Each of the four cysteines would be reasonable targets for deletion or substitution by another amino acid.

Several naturally-occurring proteins are known to contain one or more "free" cysteine residues. Examples of such naturally-occurring proteins include human Interleukin (IL)-2, beta interferon (Mark et al., 1984), G-CSF (Lu et al., 1989) and basic fibroblast growth factor (Thompson, 1992). IL-2, G-CSF and beta interferon contain an odd number of cysteine residues, whereas basic fibroblast growth factor contains an even number of cysteine residues.

However, expression of recombinant proteins containing free cysteine residues has been problematic due to reactivity of the free sulfhydryl at physiological conditions. Several recombinant proteins containing free cysteines have been expressed as intracellular proteins in bacteria such as E. coli. Examples include natural proteins such as IL-2, beta interferon, G-CSF, basic fibroblast growth factor and engineered cysteine muteins of IL-2 (Goodson and Katre, 1990), IL-3 (Shaw et al., 1992), Tumor Necrosis Factor Binding Protein (Tuma et al., 1995), IGF-I (Cox and McDermott, 1994), IGFBP-1 (Van Den Berg et al., 1997) and protease nexin and related proteins (Braxton, 1998). All of these proteins were insoluble when expressed intracellularly in bacteria. The insoluble proteins could be refolded into their native conformations by performing a series of denaturation, reduction and refolding procedures. These steps add time and cost to the manufacturing process for producing the proteins in bacteria. Improved stability and yields of IL-2 (Mark et al., 1985) and beta interferon (DeChiara et al., 1986) have been obtained by substituting another amino acid, e.g., serine, for the free cysteine residue. It would be preferable to express the recombinant proteins in a soluble, biologically active form to eliminate these extra steps.

One known method of expressing soluble recombinant proteins in bacteria is to secrete them into the periplasmic space or into the media. It is known that certain recombinant proteins such as GH are expressed in a soluble active form when they are secreted into the E. coli periplasm, whereas they are insoluble when expressed intracellularly in E. coli. Secretion is achieved by fusing DNA sequences encoding growth hormone or other proteins of interest to DNA sequences encoding bacterial signal sequences such as those derived from the stII (Fujimoto et al., 1988) and ompA proteins (Ghrayeb et al., 1984). Secretion of recombinant proteins in bacteria is desirable because the natural N-terminus of the recombinant protein can be maintained. Intracellular expression of recombinant proteins requires that an N-terminal methionine be present at the amino-terminus of the recombinant protein. Methionine is not normally present at the amino-terminus of the mature forms of many human proteins. For example, the amino-terminal amino acid of the mature form of human growth hormone is phenylalanine. An amino-terminal methionine must be added to the amino-terminus of a recombinant protein, if a methionine is not present at this position, in order for the protein to be expressed efficiently in bacteria. Typically addition of the amino-terminal methionine is accomplished by adding an ATG methionine codon preceding the DNA sequence encoding the recombinant protein. The added N-terminal methionine often is not removed from the recombinant protein, particularly if the recombinant protein is insoluble. Such is the case with hGH, where the N-terminal methionine is not removed when the protein is expressed intracellularly in E. coli. The added N-terminal methionine creates a "non-natural" protein that potentially can stimulate an immune response in a human. In contrast, there is no added methionine on hGH that is secreted into the periplasmic space using stII (Chang et al., 1987) or ompA (Cheah et al., 1994) signal sequences; the recombinant protein begins with the native amino-terminal amino acid phenylalanine. The native hGH protein sequence is maintained because of bacterial enzymes that cleave the stII-hGH protein (or ompA-hGH protein) between the stII (or ompA) signal sequence and the start of the mature hGH protein. While the periplasmic space is believed to be an oxidizing environment that should promote disulfide bond formation, coexpression of protein disulfide isomerase with bovine pancreatic trypsin inhibitor resulted in a six-fold increase in the yield of correctly folded protein from the *E. coli* periplasm (Ostermeier et al., (1996). This result would suggest that periplasmic protein folding can at times be inefficient and is in need of improvement for large scale protein production.

hGH has four cysteines that form two disulfides. hGH can be secreted into the *E. coli* periplasm using stII or ompA signal sequences. The secreted protein is soluble and biologically active (Hsiung et al., 1986). The predominant secreted form of hGH is a monomer with an apparent molecular weight by sodium dodecyl sulfate polyacrylamide gel electrophoresis (SDS-PAGE) of 22 kDa. Recombinant hGH can be isolated from the periplasmic space by using an osmotic shock procedure (Koshland and Botstein, 1980), which preferentially releases periplasmic, but not intracellular, proteins into the osmotic shock buffer. The released hGH protein is then purified by column chromatography ((Hsiung et al., 1986).

When similar procedures were attempted to secrete hGH variants containing a free cysteine residue (five cysteines; 2N+1), it was discovered that the recombinant hGH variants formed multimers and aggregates when isolated using standard osmotic shock and purification procedures developed for hGH. Very little of the monomeric hGH variant proteins could be detected by non-reduced SDS-PAGE in the osmotic shock lysates or during purification of the proteins by column chromatography.

Alpha interferon (IFN-α2) also contains four cysteine residues that form two disulfide bonds. IFN-α2 can be secreted into the *E. coli* periplasm using the stII signal sequence (Voss et al., 1994). The secreted protein is soluble and biologically active (Voss et al., 1994). The predominant secreted form of IFN-α2 is a monomer with an apparent molecular weight by SDS-PAGE of 19 kDa. Secreted recombinant IFN-α2 can be purified by column chromatography (Voss et al., 1994).

When similar procedures were attempted to secrete IFN-α2 variants containing a free cysteine residue (five cysteines; 2N+1), it was discovered that the recombinant IFN-α2 variants formed multimers and aggregates when isolated using standard purification procedures developed for IFN-α2. The IFN-α2 variants eluted from the columns very differently than IFN-α2 and very little of the monomeric IFN-α2 variant proteins could be purified using column chromatography procedures developed for IFN-α2.

An alternative method to synthesizing a protein containing a free cysteine residue is to introduce a thiol group into a protein post-translationally via a chemical reaction with succinimidyl 6-[3-2-pyridyldithio)propionamido]hexanoate (LC-SPDP, commercially available from Pierce Chemical Company). LC-SPDP reacts with lysine residues to create a free sulfhydryl group. Chemically cross-linked dimeric EPO was prepared using this reagent in conjunction with a maleimide protein modifying reagent (Sytkowsk et al., 1998). A heterologous mixture of chemically cross-linked EPO proteins was recovered after purification due to non-specific modification of the various lysine residues in EPO. Enhanced pharmacokinetics and in vivo potency of the chemically cross-linked EPO proteins were observed.

Another method that has been used to increase the size of a protein and improve its in vivo potency involves dimerization of the protein using chemical crosslinking reagents. GH is thought to transduce a cellular signal by cross-linking two GH receptors. A GH-GH dimer might facilitate enhanced receptor dimerization and subsequent amplification of the intracellular signal.

Chemically cross-linked dimeric hGH proteins have been described by Mockridge et al. (1998). Using a water soluble cross-linking reagent 1-ethyl-3-(3-dimethylaminopropyl)-carbodiimide (EDC), GH was randomly derivatized to give predominantly amide-linked dimers but also amide-linked multimers, depending on the concentration of EDC reagent used. While an increase in in vivo potency was observed, the final protein preparation was heterogeneous due to non-specific reaction of the EDC reagent with various amino acids in the protein, including lysine, aspartic acid and glutamic acid residues and the amino- and carboxy-termini. Injection of such a preparation into humans would be undesirable due to the toxic nature of EDC, potential immunogenic response to the unnatural amide bond formed between the proteins. Generating consistent batches of a purified protein also would be difficult at the manufacturing scale.

Therefore, despite considerable effort, a need still exists for a process for generating homogeneous preparations of long acting recombinant proteins by enhancement of protein molecular weight. A need also for methods that allow secretion and recovery of recombinant proteins containing free cysteine residues in high yield. The present invention satisfies these needs and provides related advantages as well.

SUMMARY OF THE INVENTION

The present invention relates to methods for obtaining a soluble protein having a free cysteine. The methods are generally accomplished by obtaining a host cell capable of expressing the soluble protein, exposing the host cell to a cysteine blocking agent, and isolating the soluble protein from the host cell. In one embodiment in which the protein is not secreted into the media by the host cell, the host cell is disrupted in the presence of the cysteine blocking agent and the soluble protein is isolated or purified from the soluble fraction of the disrupted host cell. In another embodiment in which the soluble protein is secreted by the host cell into the media, the host cell is exposed to the cysteine blocking agent before, during or after synthesis of the soluble protein by the host cell.

Suitable host cells include bacteria, yeast, insect or mammalian cells. Preferably, the host cell is a bacterial cell, particularly *E. coli*.

Preferably, the soluble protein produced by the methods of the present invention are recombinant proteins, especially cysteine variants or muteins of a protein. The methods are useful for producing proteins including, without limitation, human growth hormone, EPO and interferon, especially alpha interferon, their derivatives or antagonists. Other proteins include members of the TGF-beta superfamily, platelet derived growth factor-A, platelet derived growth factor-B, nerve growth factor, brain derived neurotophic factor, neurotrophin-3, neurotrophin-4, vascular endothelial growth factor, or a derivative or an antagonist thereof. Cysteine muteins of heavy or light chain of an immunoglobulin or a derivative thereof are also contemplated.

Useful cysteine blocking agents include any thiol-reactive compound, including for example, cystine, cystamine, dithioglycolic acid, oxidized glutathione, iodine, hydrogen peroxide, dihydroascorbic acid, tetrathionate, O-iodosobenzoate or oxygen in the presence of a metal ion.

The present methods further include various methods of attaching a PEG moiety to the soluble protein to form pegylated proteins in which the PEG moiety is attached to the soluble protein through the free cysteine. Higher order multimeric proteins involving the coupling of two or more of the soluble proteins are also within the present invention.

The present invention further includes the soluble proteins and their derivatives, including pegylated proteins, made by the methods disclosed herein. Such pegylated proteins include monopegylated hGh, EPO and alpha interferon.

The present invention also provides methods for pegylating the soluble proteins obtained by the methods described herein. Such methods include purifying the protein, reducing at least partially the protein with a disulfide-reducing agent and exposing the protein to a cysteine-reactive moiety. Optionally, the modified cysteine protein can be isolated from unmodified protein.

Methods of treating conditions treatable by growth hormone, EPO and alpha interferon are also within the present invention. The soluble proteins or their derivatives, including pegylated derivatives, are administered to patients suffering from conditions in which known growth hormone, EPO or alpha interferon is effective.

BRIEF DESCRIPTION OF THE FIGURE

FIG. 1 is a diagram of mutagenesis by overlap extension in which two separate fragments are amplified from a target DNA segment.

DESCRIPTION OF THE INVENTION

The present invention provides novel methods of obtaining proteins having free cysteine residues. The invention further provides novel proteins, particularly recombinant proteins, produced by these novel methods as well as derivatives of such recombinant proteins. The novel methods for preparing such proteins are generally accomplished by:
(a) obtaining a host cell capable of expressing a protein having a free cysteine;
(b) exposing the host cell to a cysteine blocking agent; and
(c) isolating the protein from the host cell.

In one embodiment, the methods include the steps of disrupting the host cell in the presence of the cysteine blocking agent, followed by isolating the protein from the soluble fraction of the disrupted cell.

In a further embodiment in which the proteins are secreted into the media by prokaryotic or eukaryotic host cells, the methods include the steps of:
(a) obtaining a host cell capable of expressing a protein having a free cysteine;
(b) exposing the host cell to a cysteine blocking agent during synthesis, or after synthesis but prior to purification, of the protein having a free cysteine residue; and
(d) isolating the protein from other cellular components in the media.

As identified above, the first step in these methods is to obtain a host cell capable of expressing a protein having a free cysteine residue. Suitable host cells can be prokaryotic or eukaryotic. Examples of appropriate host cells that can be used to express recombinant proteins include bacteria, yeast, insect and mammalian cells. Bacteria cells are particularly useful, especially *E. coli*.

As used herein, the term "protein having a free cysteine residue" means any natural or recombinant protein peptide containing 2N+1 cysteine residues, where N can be 0 or any integer, and proteins or peptides containing 2N cysteines, where two or more of the cysteines do not normally participate in a disulfide bond. Thus, the methods of the present invention are useful in enhancing the expression, recovery and purification of any protein or peptide having a free cysteine, particularly cysteine added variant recombinant proteins (referred to herein as "cysteine muteins" or "cysteine variants") having one or more free cysteines and/or having 2 or more cysteines that naturally form a disulfide bond. Although the expression, recovery and purification of a natural protein having a free cysteine expressed by its natural host cell can be enhanced by the methods of the present invention, the description herein predominantly refers to recombinant proteins for illustrative purposes only. In addition, the proteins can be derived from any animal species including human, companion animals and farm animals.

Accordingly, the present invention encompasses a wide variety of recombinant proteins. These proteins include, but are not limited to, glial-derived neurotrophic factor (GDNF), transforming growth factor-beta1 (TGF-beta1), TGF-beta2, TGF-beta3, inhibin A, inhibin B, bone morphogenetic protein-2 (BMP-2), BMP-4, inhibin alpha, Mullerian inhibiting substance (MIS), OP-1 (osteogenic protein 1), which are all members of the TGF-beta superfamily. The monomer subunits of the TGF-beta superfamily share certain structural features: they generally contain 8 highly conserved cysteine residues that form 4 intramolecular disulfides. Typically a ninth conserved cysteine is free in the monomeric form of the protein but participates in an intermolecular disulfide bond formed during the homodimerization or heterodimerication of the monomer subunits. Other members of the TGF-beta superfamily are described by Massague (1990), Daopin et al. (1992), Kingsley (1994), Kutty et al. (1998), and Lawton et al. (1997), incorporated herein by reference.

Immunoglobulin heavy and light chain monomers also contain cysteine residues that participate in intramolecular disulfides as well as free cysteines (Roitt et al., 1989 and Paul, 1989). These free cysteines normally only participate in disulfide bonds as a consequence of multimerization events such as heavy chain homodimerization, heavy chain-light chain heterodimerization, homodimerization of the (heavy chain-light chain) heterodimers, and other higher order assemblies such as pentamerization of the (heavy chain-light chain) heterodimers in the case of IgM. Thus, the methods of the present invention can be employed to enhance the expression, recovery and purification of heavy and/or light chains (or various domains thereof) of human immunoglobulins such as IgG1, IgG2, IgG3, IgG4, IgM IgA1, IgA2, secretory IgA, IgD and IgE. Immunoglobulins from other species could also be similarly expressed, recovered and purified. Proteins genetically fused to immunoglobulins or immunoglobulin domains as described in Chamow & Ashkenazi (1996) could also be similarly expressed, recovered and purified.

The present methods can also enhance the expression, recovery and purification of additional recombinant proteins including members of growth hormone superfamily. The following proteins are encoded by genes of the growth hormone (GH) supergene family (Bazan (1990); Bazan (1991); Mott and Campbell (1995); Silvennoinen and Ihle (1996); Martin et al., 1990; Hannum et al., 1994): growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, oncostatin M, ciliary neurotrophic factor, leukemia inhibitory factor, alpha interferon, beta interferon, gamma interferon, omega interferon, tau interferon, granulocyte-colony stimulating factor (G-CSF), granulocyte-macrophage colony stimulating factor (GM-CSF), macrophage colony stimulating factor (M-CSF), cardiotrophin-1 (CT-1), Stem Cell Factor and the flt3/flk2 ligand ("the GH supergene family"). It is anticipated that additional members of this gene family will be identified in the future through gene cloning and sequencing. Members of the GH supergene family have similar secondary and tertiary structures, despite the fact that they generally have limited amino acid or DNA sequence identity. The shared structural features allow new members of the gene family to be readily identified.

A group of proteins has been classed as a structural superfamily based on the shared structural motif termed the "cystine knot". The cystine knot is defined by six conserved cysteine residues that form three intramolecular disulfide bonds that are topologically "knotted" (McDonald and Hendrickson, 1993). These proteins also form homo- or heterodimers and in some but not all instances dimerization involves intermolecular disulfide formation. Members of this family include the members of the TGF-beta superfamily and other proteins such as platelet derived growth factor-A (PDGF-A), PDGF-B, nerve growth factor (NGF), brain derived neurotrophic factor (BDNF), neurotrophin-3 (NT-3), NT-4, and vascular endothelial growth factor (VEGF). Cystine and other cysteine blocking reagents could also enhance expression, recovery and purification of proteins with this structural motif.

The present methods can also enhance the expression, recovery and purification of other recombinant proteins and/or cysteine added variants of those proteins. Classes of proteins would include proteases and other enzymes, protease inhibitors, cytokines, cytokine antagonists, allergens, chemokines, gonadotrophins, chemotactins, lipid-binding proteins, pituitary hormones, growth factors, somatomedans, immunoglobulins, interleukins, interferons, soluble receptors, vaccines, and hemoglobins. Specific examples of proteins include, for example, leptin, insulin, insulin-like growth factor 1 (IGF1), superoxide dismutase, catalase, asparaginase, uricase, fibroblast growth factors, arginase, phenylalanine ammonia, angiostatin, endostatin, Factor VIII, Factor IX, interleukin 1 receptor antagonist, protease nexin and antithrombin III.

Other protein variants that would benefit from PEGylation and would therefore be reasonable candidates for cysteine added modifications include proteins or peptides with poor solubility or a tendency to aggregate, proteins or peptides that are susceptable to proteolysis, proteins or peptides needing improved mechanical stability, proteins or peptides that are cleared rapidly from the body, or proteins or peptides with undesirable immunogenic or antigenic properties.

If desired, muteins of natural proteins can be generally constructed using site-directed PCR-based mutagenesis as described in general in Methods in Molecular Biology, Vol. 15: PCR Protocols: Current Methods and Applications edited by White, B. A. (1993) Humana Press, Inc., Totowa, N.J. and PCR Protocols: A Guide to Methods and Applications edited by Innis, M. A. et al. (1990) Academic Press, Inc. San Diego, Calif. Typically, PCR primer oligonucleotides are designed to incorporate nucleotide changes to the coding sequence of proteins that result in substitution of a cysteine residue for an amino acid at a specific position within the protein. Such mutagenic oligonucleotide primers can also be designed to incorporate an additional cysteine residue at the carboxy terminus or amino terminus of the coding sequence of proteins. In this latter case one or more additional amino acid residues could also be incorporated amino terminal and/or carboxy terminal to the added cysteine residue if that were desirable. Moreover oligonucleotides can be designed to incorporate cysteine residues as insertion mutations at specific positions within the protein coding sequence if that were desirable. Again, one or more additional amino acids could be inserted along with the cysteine residue and these amino acids could be positioned amino terminal and/or carboxy terminal to the cysteine residue.

The choice of sequences for mutagenic oligos is dictated by the position where the desired cysteine residue is to be placed and the propinquity of useful restriction endonuclease sites. Generally it is desirable to place the mutation, i.e. the mis-matched segment near the middle of the oligo to enhance the annealing of the oligo to the template. It is also desirable for the mutagenic oligo to span a unique restriction site so that the PCR product can be cleaved to generate a fragment that can be readily cloned into a suitable vector. An example would be one that can be used to express the mutein or that provides convenient restriction sites for excising the mutated gene and readily cloning it into such an expression vector. It is generally desirable to employ mutagenic oligos under 80 bases in length and lengths of 30-40 bases are more preferable. Sometimes mutation sites and restriction sites are separated by distances that are greater than that which is desirable for synthesis of synthetic oligonucleotides. In such instances, multiple rounds of PCR can be employed to incrementally extend the length of the PCR product such that it includes the desired useful restriction site or genes targeted for mutagenesis can be reengineered or resynthesized to incorporate restriction sites at appropriate positions. Alternatively, variations of PCR mutagenesis protocols, such as the so-called "Megaprimer Method" (Batik, S. pp 277-286 in Methods in Molecular Biology, Vol. 15: PCR Protocols: Current Methods and Applications edited by White, B. A. (1993) Humana Press, Inc., Totowa, N.J.) or "Gene Splicing by Overlap Extension" (Horton, R. M. pp 251-261 in Methods in Molecular Biology, Vol. 15: PCR Protocols: Current Methods and Applications edited by White, B. A, (1993) Humana Press, Inc., Totowa, N.J.), both incorporated herein by reference, can also be employed to construct such mutations.

Next, the host cell is exposed to a cysteine blocking agent. In one embodiment, the blocking agent is present at the time of cell disruption, and preferably is added prior to disrupting the cells. Cell disruption can be accomplished by, for example, mechanical sheer such as a French pressure cell, enzymatic digestion, sonication, homogenization, glass bead vortexing, detergent treatment, organic solvents, freeze thaw, grinding with alumina or sand and the like (Bollag et al., 1996).

In an alternative embodiment, the cysteine blocking agent can be exposed to the host cell before, during or after the host cell is induced to express the desired protein. For example, the host cell can be cultured in the presence of the cysteine blocking agent, which might be preferred for expression of proteins that are secreted into the media such as erythropoietin, for example. Alternatively, prior to or at the time of, exposing the host cell to the cysteine blocking agent, the host cell can be induced to express the desired protein, either as a secreted protein in the periplasm or media, or as a cytoplasmic protein. Methods known in the art can be used to induce such expression in the cytoplasm or to direct secretion depending on cell origin, including, for example, the methods described in the examples below. A wide variety of signal peptides have been used successfully to transport proteins to the periplasmic space. Examples of these include prokaryotic signal sequences such as ompA, stII, PhoA signal (Denefle et al., 1989), OmpT (Johnson et al., 1996), LamB and OmpF (Hoffman and Wright, 1985), beta-lactamase (Kadonaga et al., 1984), enterotoxins LT-A, LT-B (Morioka-Fujimoto et al., 1991), and protein A from S. aureus (Abrahmsen et al., 1986). A number of non-natural, synthetic, signal sequences that facilitate secretion of certain proteins are also known to those skilled in the art.

For proteins secreted to the periplasm, an osmotic shock treatment can be used to selectively disrupt the outer membrane of the host cells with the resulting release of periplasmic proteins. The osmotic shock buffer can be any known in the art, including, for example, the osmotic shock buffer and procedures described in Hsiung et al. (1986), or as described in the examples below. For proteins secreted into the media, preferably the media should contain the cysteine blocking agent during the time the cells express and secrete the protein. The cysteine blocking agent also could be added to the media following secretion of the protein but prior to purification of the protein.

The cysteine blocking agent can be added to the culture media at a concentration in the range of about 0.1 µM to about 100 mM. Preferably, the concentration of cysteine blocking agent in the media is about 50 µM to about 5 mM Although not wishing to be bound by any particular theory, it is believed that the cysteine blocking agents used in the present methods covalently attach to the "free" cysteine residue, forming a mixed disulfide, thus stabilizing the free cysteine residue and preventing multimerization and aggregation of the protein. Alternatively, the presence of an oxidizing agent in the osmotic shock buffers may be augmenting the protein refold process in case incomplete renaturation had occurred following secretion of the protein into the periplasmic space. However, as noted above, periplasmic protein refolding can be inefficient. For this reason it is believed that addition of cystine to osmotic shock buffers also may increase the recovery of recombinant proteins containing an even number of cysteine residues, even if the cysteines normally form disulfide bonds. In addition, the inventors believe it may be advantageous to add cystine or similar compounds to the fermentation media during bacterial growth because these compounds should diffuse into the periplasm due to the porous nature of the bacterial outer membrane. Protein folding and blocking of the free cysteine can be accomplished before cell recovery and lysis. Early protein stabilization protects against proteolysis and can contribute to higher recovery yields of recombinant proteins.

A number of thiol-reactive compounds can be used as cysteine blocking agents to stabilize proteins containing free cysteines. In addition to cystine, blocking agents can also include reagents containing disulfide linkages such as cystamine, dithioglycolic acid, oxidized glutathione, 5,5'-dithiobis (2-nitrobenzoic acid (Ellman's reagent), pyridine disulfides, compounds of the type R—S—S—CO—OCH$_3$, other derivatives of cystine such as diformylcystine, diacetylcystine, diglycylcystine, dialanylcystine diglutaminylcystine, cystinyldiglycine, cystinyldiglutamine, dialanylcystine dianhydride, cystine phenylhydantoin, homocystine, dithiodipropionic acid, dimethylcystine, or any dithiol or chemical capable of undergoing a disulfide exchange reaction. Sulfenyl halides can also be used to prepare mixed disulfides. Other thiol blocking agents that may find use in stabilizing cysteine added protein variants include compounds that are able to reversibly react with free thiols. These agents include certain heavy metals salts or organic derivatives of zinc, mercury, and silver. Other mercaptide forming agents or reversible thiol reactive compounds are described by R. Cecil and J. R. McPhee (1959) and Torchinskii (1971).

In the final step of the general method, the desired protein is recovered and purified from the soluble cytoplasmic fraction, the soluble periplasmic fraction or the soluble fraction of the media. Any method for recovering and purifying proteins from the media, cytoplasmic or periplasmic fraction can be used. Such recovery and purification methods are known or readily determined by those skilled in the art, including, for example, centrifugation, filtration, dialysis, chromatography, including size exclusion, procedures and the like. A suitable method for the recovery and purification of a desired protein will depend, in part, on the properties of the protein and the intended use.

The present invention further provides novel methods for producing soluble interferon, particularly alpha interferon, that results in a significant increase in the percent of the recovered interferon that has been properly processed. These methods include culturing host cells capable of expressing interferon at a pH range of about 5 to about 6.5, and preferably about 5.5 to about 6.5. Published reports (Voss et al. (1994)) using a higher pH only resulted in 50% properly processed interferon, whereas the new methods of the present invention at lower pHs recovered about 80-90%.

A discovery was made that certain of the monomeric hGH cysteine variants formed disulfide-linked dimeric hGH proteins during the chromatography procedures used to purify these proteins. The disulfide-linked hGH dimers formed when cystine was removed from the column buffers. New procedures were developed to purify the disulfide-linked dimeric hGH proteins because the disulfide-linked dimeric hGH proteins behaved differently than monomeric hGH proteins during the column chromatography steps used to purify the proteins. Unexpectedly, it was discovered that the disulfide-linked dimeric hGH proteins were biologically active in in vitro bioassays. Biologically active, homogeneous, disulfide-linked dimeric hGH proteins are novel. Accordingly, the present invention further relates to these biologically active, homogeneous di-sulfide lined, dimeric hGH proteins as well. Higher order multimers are also contemplated, including trimers, tetramers and the like, as described in the examples below.

The purified proteins can then be further processed if desired. For example, the proteins can be PEGylated at the free cysteine site with various cysteine-reactive PEG reagents, and subsequently purified as monoPEGylated proteins. The term "monoPEGylated" is defined to mean a protein modified by covalent attachment of a single PEG molecule at a specific site on the protein. Any method known to those skilled in the art can be used, including, for example, the methods described in the examples below, particularly Example 11.

Braxton (1998) teaches methods for PEGylating cysteine muteins of proteins, and in particular cysteine muteins of GH and erythropoietin. Braxton (1998) specifically teaches that the buffers used to PEGylate the cysteine muteins should not contain a reducing agent. Examples of reducing agents provided by Braxton (1998) are beta-mercaptoethanol (BME) and dithiothreitol (DTT). When similar procedures were used to PEGylate cysteine muteins of GH, erythropoietin and alpha interferon, it was discovered that the cysteine muteins did not PEGylate. It has now been discovered that treatment of the purified cysteine muteins with a reducing agent is required for the proteins to be PEGylated. Although not wanting to be bound by any particular theory, the inventors believe that the reducing agent is required to reduce the mixed disulfide and expose the free cysteine residue in the protein so that the free cysteine can react with the PEG reagent. Thus, the present invention also relates to methods for PEGylating cysteine muteins of GH, erythopoietin, alpha interferon and other proteins containing 2N+1 cysteine residues, proteins containing 2N cysteine residues where two or more of the cysteine residues are free, particularly those muteins and proteins in which the free cysteine residue is blocked by a mixed disulfide.

The present invention further relates to purified, monoPEGylated protein variants produced by the methods disclosed herein that are not only biologically active, but also retain high specific activity in protein-dependent mammalian cell proliferation assays. Such protein variants include, for example, the following purified, monPEGylated cysteine muteins: hGH, EPO and alpha IFN. For example, the in vitro biological activities of the monoPEGylated hGH variants were 10- to 100-fold greater than the biological activity of hGH that has been PEGylated using NHS-PEG reagents.

In one embodiment of the monoPEGylated hGH, the polyethylene glycol is attached to the C-D loop of hGH and the resulting monoPEGylated hGH has an $EC_{50}$ less than about 110 ng/ml (5 nM), preferably less than about 50 ng/ml (2.3 nM). Alternatively, the polyethylene glycol moiety can be attached to a region proximal to the Helix A of hGH and the resulting monoPEGylated hGH has an $EC_{50}$ less than about 110 ng/ml (5 nM), preferably less than 11 ng/ml (0.5 nM), and more preferably less than about 2.2 ng/ml (0.1 nM).

In one embodiment of the monoPEGylated EPO, the polyethylene glycol is attached to the C-D loop of EPO and the resulting monoPEGylated EPO has an $EC_{50}$ less than about 1000 ng/ml (21 nM), preferably less than about 100 ng/ml (approximately 6 nM), more preferably less than about 10 ng/ml (approximately 0.6 nM) and most preferably less than about 1 ng/ml (approximately 0.06 nM). Alternatively, the polyethylene glycol moiety can be attached to the A-B loop of EPO and the resulting monoPEGylated EPO has an $EC_{50}$ less than about 100 ng/ml (approximately 5 nM), preferably less than 20 ng/ml (approximately 1 nM), and more preferably less than about 1 ng/ml (approximately 0.05 nM).

In one embodiment of the monoPEGylated alpha IFN, the polyethylene glycol is attached to the region proximal to Helix A of alpha IFN and the resulting monoPEGylated alpha IFN has an $IC_{50}$ less than about 100 pg/ml (approximately 5 pM), more preferably less than about 50 pg/ml (approximately 2.5 pM) and most preferably about 22 ng/ml (approximately 1.2 pM). Alternatively, the polyethylene glycol moiety can be attached to the C-D loop of IFN-α2 and the resulting monoPEGylated IFN-α2 has an $EC_{50}$ less than about 100 pg/ml (approximately 5 pM).

There are over 25 distinct IFN-α genes (Pestka et al., 1987). Members of the IFN-α family share varying degrees of amino acid homology and exhibit overlapping sets of biological activities. Non-natural recombinant IFN-αs, created through joining together regions of different IFN-α proteins are in various stages of clinical development (Horisberger and DiMarco, 1995). A non-natural "consensus" interferon (Blatt et al., 1996), which incorporates the most common amino acid at each position of IFN-α, also has been described. Appropriate sites for PEGylating cysteine muteins of IFN-α2 should be directly applicable to other members of the IFN-α gene family and to non-natural IFN-αs. Kinstler et al., (1996) described monoPEGylated consensus interferon in which the protein is preferentially mono PEGylated at the N-terminal, non-natural methionine residue. Bioactivity of the PEGylated protein was reduced approximately 5-fold relative to non-modified consensus interferon (Kinstler et al., 1996).

The present invention further provides protein variants that can be covalently attached or conjugated to each other or to a chemical group to produce higher order multimers, such as dimers, trimers and tetramers. Such higher order multimers can be produced according to methods known to those skilled in the art or as described in Example 15 below. For example, such a conjugation can produce a hGH, EPO or alpha IFN adduct having a greater molecular weight than the corresponding native protein. Chemical groups suitable for coupling are preferably non-toxic and non-immunogenic. These chemical groups would include carbohydrates or polymers such as polyols.

The "PEG moiety" useful for attaching to the cysteine variants of the present invention to form "pegylated" proteins include any suitable polymer, for example, a linear or branched chained polyol. A preferred polyol is polyethylene glycol, which is a synthetic polymer composed of ethylene oxide units. The ethylene oxide units can vary such that PEGylated-protein variants can be obtained with apparent molecular weights by size-exclusion chromatography ranging from approximately 30-500,000. The size of the PEG moiety directly impacts its circulating half-life Yamaoka et al. (1994). Accordingly, one could engineer protein variants with differing circulating half-lives for specific therapeutic applications or preferred dosing regimes by varying the size or structure of the PEG moiety. Thus, the present invention encompasses GH protein variants having an apparent molecular weight greater than about 30 kDa, and more preferably greater than about 70 kDa as determined by size exclusion chromatography, with an $EC_{50}$ less than about 400 ng/ml (18 nM), preferably less than 10 ng/ml (5 nM), more preferably less than about 10 ng/ml (0.5 nM), and even more preferably less than about 2.2 ng/ml (0.1 nM). The present invention further encompasses EPO protein variants having an apparent molecular weight greater than about 30 kDa, and more preferably greater than about 70 kDa as determined by size exclusion chromatography, with an $EC_{50}$ less than about 1000 ng/ml (21 nM), preferably less than 100 ng/ml (6 nM), more preferably less than about 10 ng/ml (0.6 nM), and even more preferably less than about 1 ng/ml (0.06 nM). The present invention further encompasses alpha IFN (IFN-α) protein variants having an apparent molecular weight greater than about 30 kDa, and more preferably greater than about 70 kDa as determined by size exclusion chromatography, with an $IC_{50}$ less than about 1900 pg/ml (100 pM), preferably less than 400 pg/ml (21 pM), more preferably less than 100 pg/ml (5 nM), and even more preferably less than about 38 pg/ml (2 pM).

The reactive PEG end group for cysteine modification includes but is not limited to vinylsulfone, maleimide and iodoacetyl moieties. The PEG end group should be specific for free thiols with the reaction occurring under conditions that are not detrimental to the protein.

Antagonist hGH variants also can be prepared using a cysteine-added variant GH where chemical derivatization does not interfere with receptor binding but does prohibit the signaling process. Conditions that would benefit from the administration of a GH antagonist include acromegaly, vascular eye diseases, diabetic nephropathy, restenosis following angioplasty and growth hormone responsive malignancies.

As used herein, the term "derivative" refers to any variant of a protein expressed and recovered by the present methods. Such variants include, but are not limited to, PEGylated versions, dimers and other higher order variants, amino acid variants, fusion proteins, changes in carbohydrate, phosphorylation or other attached groups found on natural proteins, and any other variants disclosed herein.

The compounds produced by the present methods can be used for a variety of in vitro and in vivo uses. The proteins and their derivatives of the present invention can be used for research, diagnostic or therapeutic purposes that are known for their wildtype, natural, or previously-known modified counterparts. In vitro uses include, for example, the use of the protein for screening, detecting and/or purifying other proteins.

For therapeutic uses, one skilled in the art can readily determine the appropriate dose, frequency of dosing and route of administration. Factors in making such determinations include, without limitation, the nature of the protein to be administered, the condition to be treated, potential patient compliance, the age and weight of the patient, and the like. The compounds of the present invention can also be used as delivery vehicles for enhancement of the circulating half-life of the therapeutics that are attached or for directing delivery to a specific target within the body.

The following examples are not intended to be limiting, but only exemplary of specific embodiments of the invention.

EXAMPLE 1

Development of an In Vitro Bioassay for Human Growth Hormone

An hGH cell proliferation assay that uses the murine FDC-P1 cell line stably transfected with the rabbit GH receptor was developed (Rowlinson et al., 1995). The mouse FDC-P1 cell line was purchased from the American Type Culture Collection and routinely propagated in RPMI 1640 media supplemented with 10% fetal calf serum, 50 µg/ml penicillin, 50 µg/ml streptomycin, 2 mM glutamine and 17-170 Units/ml mouse IL-3 (FDC-P1 media).

A. Cloning a cDNA Encoding the Rabbit GH Receptor

The rabbit GH receptor was cloned by PCR using forward primer BB3 (5'-CCCCGGATCCGCCACCATG-GATCTCTGG CAGCTGCTGTT-3') (SEQ.ID.NO. 1) and reverse primer BB36 (5'-CCCCGTCGACTCTAGAGC-CATTA GATACAAAGCTCT TGGG-3') (SEQ.ID.NO. 2). BB3 anneals to the DNA sequence encoding the initiator methionine and amino terminal portion of the receptor. BB3 contains an optimized KOZAK sequence preceding the initiator methionine and a Bam HI site for cloning purposes. BB36 anneals to the 3' untranslated region of the rabbit GH receptor mRNA and contains Xba I and Sal I restriction sites for cloning purposes. Rabbit liver poly(A)$^+$ mRNA (purchased from CLONTECH, Inc.) was used as the substrate in first strand synthesis of single-stranded cDNA to produce template for PCR amplification. First strand synthesis of single-stranded cDNA was accomplished using a 1st Strand cDNA Synthesis Kit for RT-PCR (AMV) from Boehringer Mannheim Corp. Parallel first strand cDNA syntheses were performed using random hexamers or BB36 as the primer. Subsequent PCR reactions using the products of the first strand syntheses as templates were carried out with primers BB3 and BB36. The expected ~1.9 kb PCR product was observed in PCR reactions using random hexamer-primed or BB36-primed cDNA as template. The random hexamer-primed cDNA was digested with Bam HI and Xba I, which generates two fragments (~365 bp and ~1600 bp) because the rabbit GH receptor gene contains an internal Bam HI site. Both fragments were gel-purified. The full-length rabbit GH receptor cDNA was then cloned in two steps. First the ~1600 bp Bam HI-Xba I fragment was cloned into pcDNA3.1(+) (Invitrogen Corporation) that had been digested with these same two enzymes. These clones were readily obtained at reasonable frequencies and showed no evidence of deletions as determined by restriction digests and subsequent sequencing. To complete the rabbit receptor cDNA clone, one of the sequenced plasmids containing the 1600 bp Bam HI-Xba I fragment was digested with Bam HI, treated with calf alkaline phosphatase, gel-purified and ligated with the gel-purified ~365 bp Bam HI fragment that contains the 5' portion of the rabbit GH receptor gene. Transformants from this ligation were picked and analyzed by restriction digestion and PCR to confirm the presence of the ~365 bp fragment and to determine its orientation relative to the distal segment of the rabbit GH receptor gene. The sequence for one full length clone was then verified. This plasmid, designated pBBT118, was used to stably transfect FDC-P1 cells.

B. Selection of Stably Transfected FDC-P1 Cells Expressing the Rabbit GH Receptor Endotoxin-free pBBT118 DNA was prepared using a Qiagen "Endo-Free Plasmid Purification Kit" and used to transfect FDC-P1 cells. Mouse IL-3 was purchased from R&D Systems. FDC-P1 cells were transfected with plasmid pBBT118 using DMRIE-C cationized lipid reagent purchased from GIBCO, following the manufacturer's recommended directions. Briefly, 4 µg of plasmid DNA were complexed with 4-30 µl of the DMRIE-C reagent in 1 ml of OptiMEM media (GIBCO) for 45 minutes in six well tissue culture dishes. Following complex formation, $2 \times 10^6$ FDC-P1 cells in 200 µl of OptiMEM media supplemented with mouse IL-3 were added to each well and the mixture left for 4 h at 37° C. The final mouse IL-3 concentration was 17 Units/ml. Two ml of FDC-P1 media containing 15% fetal bovine serum were added to each well and the cells left overnight at 37° C. The next day transfected cells were transferred to T-75 tissue culture flasks containing 15 ml FDC-P1 media supplemented with IL-3 (17 U/ml), hGH (5 nM) and 10% horse serum rather than fetal calf serum. Horse serum was used because of reports that fetal calf serum contains a growth-promoting activity for FDC-P1 cells. Three days later the cells were centrifuged and resuspended in fresh FDC-P1 media containing 400 g/ml G418, 17 U/ml IL-3, 5 nM hGH, 10% horse serum and incubated at 37° C. Media was changed every few days. The cells from each transfection were split into T-75 tissue culture flasks containing fresh media and either mouse IL-3 (17 U/ml) or hGH (5 nM). G418 resistant cells were obtained from both the IL-3- and hGH-containing flasks. The transformants used in the bioassays originated from flasks containing hGH. Twelve independent cell lines were selected by limiting dilution. Five of the cell lines (GH-R3, -R4, -R5, -R6 and -R9) showed a good proliferative response to hGH. Preliminary experiments indicated that the $EC_{50}$ for hGH was similar for each cell line, although the magnitude of the growth response varied depending upon the line. The GH-R4 cell line was studied in most detail and was used for the assays presented below. The cell lines were routinely propagated in RPMI 1640 media containing 10% horse serum, 50 Units/ml penicillin, 50 µg/ml streptomycin, 2 mM glutamine, 400 µg/ml G418 and 2-5 nM pituitary hGH or rhGH.

C. Development of an hGH Bioassay Using FDC-P1 Expressing the Rabbit GH Receptor A modified version of the MTT cell proliferation assay described by Rowlinson et al. (1995) was developed to measure hGH bioactivity. Our assay measures uptake and reduction of the dye MTS, which creates a soluble product, rather than MTT, which creates an insoluble product that must be solubilized with organic solvents. The advantage of using MTS is that absorbance of the wells can be determined without the need to lyse the cells with organic solvents.

GH-R4 cells were washed three times with phenol red-free RPMI 1640 media and suspended in assay media (phenol red-free RPMI 1640, 10% horse serum, 50 Units/ml penicillin, 50 µg/ml streptomycin, 400 µg/ml G418) at a concentration of $1 \times 10^5$ cells/ml. Fifty microliters of the cell suspension ($5 \times 10^3$ cells) were added to wells of a 96 well flat bottomed tissue culture plate. Serial three-fold dilutions of protein samples were prepared in assay media and added to microtiter wells in a volume of 50 µl, yielding a final volume of 100 µl per well. Protein samples were assayed in triplicate wells. Plates were incubated at 37° C. in a humidified 5% $CO_2$ tissue culture incubator for 66-72 h, at which time 20 µl of an MTS/PES (PES is an electron coupler) reagent mixture (Cell- Titer 96 Aqueous One solution reagent, Promega Corporation) was added to each well. Absorbance of the wells at 490 nm was measured 2-4 h later. Absorbance value means+/− standard deviations for the triplicate wells were calculated. Control wells contained media but no cells. Absorbance values for the control wells (typically 0.06-0.2 absorbance units) were subtracted from the absorbance values for the sample wells. Control experiments demonstrated that absorbance signals correlated with cell number up to absorbance values of 2. All assays included a human pituitary GH standard. Experiments utilizing the parental FDC-P1 cell line were performed as described above except that the assay media did not contain G418 and fetal calf serum was substituted for horse serum.

EXAMPLE 2

Cloning and Expression of rhGH

A. Cloning a cDNA Encoding Human Growth Hormone (GH)

A human GH cDNA was amplified from human pituitary single-stranded cDNA (commercially available from CLONTECH, Inc., Palo Alto, Calif.) using the polymerase chain reaction (PCR) technique and primers BB1 and BB2. The sequence of BB1 is (5'-GGGGGTCGACCATATGTTC-CCAACCATTCCCTTATCCAG-3') (SEQ.ID.NO. 3). The sequence of BB2 is (5'-GGGGGATCCTCACTAGAAGC-CACAGCTGCCCTC-3') (SEQ.ID.NO. 4). Primer BB1 was designed to encode an initiator methionine preceding the first amino acid of mature GH, phenylalanine, and Sal I and Nde I sites for cloning purposes. The reverse primer, BB2, contains a Bam HI site for cloning purposes. The PCR reactions contained 20 pmoles of each oligo primer, 1×PCR buffer (Perkin-Elmer buffer containing $MgCl_2$), 200 μM concentration of each of the four nucleotides dA, dC, dG and dT, 2 ng of single-stranded cDNA, 2.5 units of Taq polymerase (Perkin-Elmer) and 2.5 units of Pfu polymerase (Stratagene, Inc). The PCR reaction conditions were: 96° C. for 3 minutes, 35 cycles of (95° C., 1 minute; 63° C. for 30 seconds; 72° C. for 1 minute), followed by 10 minutes at 72° C. The thermocycler employed was the Amplitron II Thermal Cycler (Thermolyne) The approximate 600 bp PCR product was digested with Sal I and Bam HI, gel-purified and cloned into similarly digested plasmid pUC19 (commercially available from New England BioLabs, Beverly, Mass.). The ligation mixture was transformed into E. coli strain DH5alpha and transformants selected on LB plates containing ampicillin Several colonies were grown overnight in LB media and plasmid DNA isolated using miniplasmid DNA isolation kits purchased from Qiagen, Inc (Valencia, Calif.). Clone LB6 was determined to have the correct DNA sequence.

For expression in E. coli, clone LB6 was digested with Nde I and Eco RI, the approximate 600 bp fragment gel-purified, and cloned into plasmid pCYB 1 (commercially available from New England Biolabs, Beverly, Mass.) that had been digested with the same enzymes and treated with calf alkaline phosphatase. The ligation mixture was transformed into E. coli DH5alpha and transformants selected on LB ampicillin plates. Plasmid DNA was isolated from several transformants and screened by digestion with Nde I and Eco RI. A correct clone was identified and named pCYB1: wtGH (pBBT120). This plasmid was transformed into E. coli strains JM109 or W3110 (available from New England BioLabs and the American Type Culture Collection).

B. Construction of stII-GH

Wild type GH clone LB6 (pUC19: wild type GH) was used as the template to construct a GH clone containing the E. coli stII signal sequence. Because of its length, the stII sequence was added in two sequential PCR reactions. The first reaction used forward primer BB12 and reverse primer BB10. BB10 has the sequence (5' CGCGGATCCGATTAGAATCCA-CAGCTCCCCTC 3') (SEQ.ID.NO. 5). BB12 has the sequence (5'-GCATCTATGTTCGTTTTCTCTATCGC-TACCAACGCTTACGCA TTCCCAACCATTCCCTTATC-CAG-3') (SEQ.ID.NO. 6). The PCR reactions were as described for amplifying wild type GH. The approximate 630 bp PCR product was gel-purified using the Qiaex II Gel Extraction Kit (Qiagen, Inc), diluted 50-fold in water and 2 l used as template for the second PCR reaction. The second PCR reaction used reverse primer BB10 and forward primer BB11. BB11 has the sequence (5'CCCCCTCTAGACATAT-GAAGAAGAACATCGCATTCCTGCTGGCATCT ATGT-TCGTTTTCTCTATCG-3') (SEQ.ID.NO. 7). Primer BB11 contains XbaI and NdeI sites for cloning purposes. PCR conditions were as described for the first reaction. The approximate 660 bp PCR product was digested with XbaI and BamHI, gel-purified and cloned into similarly cut plasmid pcDNA3.1(+) (Invitrogen, Inc. Carlsbad, Calif.). Clone pcDNA3.1(+)::stII-GH(5C) or "5C" was determined to have the correct DNA sequence.

Clone "5C" was cleaved with NdeI and BamHI and cloned into similarly cut pBBT108 (a derivative of pUC19 which lacks a Pst I site, this plasmid is described below). A clone with the correct insert was identified following digestion with these enzymes. This clone, designated pBBT111, was digested with Nde I and Sal I, the 660 bp fragment containing the stII-GH fusion gene, was gel-purified and cloned into the plasmid expression vector pCYB1 (New England BioLabs) that had been digested with the same enzymes and treated with calf alkaline phosphatase. A recombinant plasmid containing the stII-GH insertion was identified by restriction endonuclease digestions. One such isolate was chosen for further studies and was designated pBBT114. This plasmid was transformed into E. coli strains JM109 or W3110 (available from New England BioLabs and the American Type Culture Collection).

C. Construction of ompA-GH

Wild type GH clone LB6 (pUC19: wild type GH) was used as the template to construct a GH clone containing the E. coli ompA signal sequence. Because of its length, the ompA sequence was added in two sequential PCR reactions. The first reaction used forward primer BB7 (5'GCAGTGGC ACTGGCTGGTTTCGCTACCGTAGCGCAG-GCCTTCCCAACCATTCCCTTATCCAG 3') (SEQ.ID.NO. 8) and reverse primer BB10: (5' CGCGGATCCGATTA-GAATCCACAGCTCCCCTC 3') (SEQ.ID.NO. 5). The PCR reactions were as described for amplifying wild type GH except that approximately 4 ng of plasmid LB6 was used as the template rather than single-stranded cDNA and the PCR conditions were 96° C. for 3 minutes, 30 cycles of (95° C. for 1 minute; 63° C. for 30 seconds; 72° C. for 1 minute) followed by 72° C. for 10 minutes. The approximate 630 bp PCR product was gel-purified using the Qiaex II Gel Extraction Kit (Qiagen, Inc), diluted 50-fold in water and 2 l used as template for the second PCR reaction. The second PCR reaction used reverse primer BB10 and forward primer BB6: (5'CCCCG TCGACACATATGAAGAAGACAGC-TATCGCGATTGCAGT GGCACTGGCTGGTTTC 3') (SE-Q.ID.NO. 9). PCR conditions were as described for the first reaction. The approximate 660 bp PCR product was gel-purified, digested with Sal I and Bam H1 and cloned into pUC19 (New England BioLabs) which was cut with Sal I and Bam H1 or pcDNA3.1(+) (Invitrogen) which had been cut by Xho I and Bam H1 (Sal I and Xho I produce compatible single-stranded overhangs). When several clones were sequenced, it was discovered that all pUC19 (8/8) clones contained errors in the region of the ompA sequence. Only one pcDNA3.1(+) clone was sequenced and it contained a sequence ambiguity in the ompA region. In order to generate a correct ompA-GH fusion, gene segments of two sequenced clones, which contained different errors separated by a convenient restriction site were recombined and cloned into the pUC19-derivative that lacks the Pst I site (see pBBT108 described below). The resulting plasmid, termed pBBT112, carries the ompA-GH fusion gene cloned as an Nde I-Bam H1 fragment into these same sites in pBBT108. This plasmid is designated pBBT112 and is used in PCR-based, site-specific mutagenesis of GH as described below.

D. Construction of Pst I⁻pUC19 (pBBT 108)

To facilitate mutagenesis of the cloned GH gene for construction of selected cysteine substitution and insertion mutations, a derivative of the plasmid pUC19 (New England BioLabs) lacking a Pst I site was constructed as follows. pUC19 plasmid DNA was digested with Pst I and subsequently treated at 75° C. with Pfu DNA Polymerase (Stratagene) using the vendor-supplied reaction buffer supplemented with 200 M dNTPs. Under these conditions the polymerase will digest the 3' single-stranded overhang created by Pst I digestion but will not digest into the double-stranded region and the net result will be the deletion of the 4 single-stranded bases which comprise the middle four bases of the Pst I recognition site. The resulting molecule has double-stranded, i.e. "blunt", ends. Following these enzymatic reactions the linear monomer was gel-purified using the Qiaex II Gel Extraction Kit (Qiagen, Inc). This purified DNA was treated with T4 DNA Ligase (New England BioLabs) according to the vendor protocols, digested with Pst I, and used to transform *E. coli* DH5alpha. Transformants were picked and analyzed by restriction digestion with Pst I and Bam H1. One of the transformants which was not cleaved by Pst I but was cleaved at the nearby Bam H1 site was picked and designated pBBT108.

E. Expression of met-hGH and stII-hGH in *E. coli* pBBT120, which encodes met-hGH, and pBBT114, which encodes stII-hGH were transformed into *E. coli* strain W3110. The parental vector pCYB 1 also was transformed into W3110. The resulting strains were given the following designations:

BOB130: W3110 (pCYB1)=vector only
BOB133: W3110 (pBBT120)=met-hGH
BOB132: W3110 (pBBT114)=stII-hGH These strains were grown overnight at 37° C. in Luria Broth (LB) containing 100 μg/ml ampicillin. The saturated overnight cultures were diluted to ~0.025 O.D.s at $A_{600}$ in LB containing 100 μg/ml ampicillin and incubated at 37° C. in shake flasks. When culture O.D.s reached ~0.25-0.5, IPTG was added to a final concentration of 0.5 mM to induce expression of the recombinant proteins. For initial experiments, cultures were sampled at 0, 1, 3, 5 and ~16 h post-induction. Samples of induced and uninduced cultures were pelleted and resuspended in SDS-PAGE sample buffer with the addition of 1% β-mercaptoethanol (BME) when desirable. Samples were electrophoresed on precast 14% Tris-glycine polyacrylamide gels. Gels were stained with Coomassie Blue or were analyzed by Western blotting.

Coomassie staining of whole cell lysates from strains BOB133, expressing met-hGH, and BOB132, expressing stII-hGH, showed a band of ~22 kDa that co-migrated with a purified rhGH standard purchased from Research Diagnostics Inc. The rhGH band was most prominent in induced cultures following overnight induction. Western blots using a polyclonal rabbit anti-hGH antiserum purchased from United States Biological, Inc. confirmed the presence of rhGH in lysates of induced cultures of BOB132 and BOB133 at both 3 and 16 h post-induction. No rhGH was detected by Western Blotting of induced cultures of the control strain BOB130 (vector only) at 3 or 16 h post-induction.

An induced culture of BOB132 (expressing stII-hGH) was prepared as described above and subjected to osmotic shock based on the analytical procedure of Koshland and Botstein (1980). This procedure ruptures the *E. coli* outer membrane and releases the contents of the periplasm into the surrounding medium. Subsequent centrifugation separates the soluble periplasmic components (recovered in the supernatant) from cytoplasmic, insoluble periplasmic, and cell-associated components (recovered in the pellet). Specifically, *E. coli* strain W3110 containing the st-II hGH plasmid was grown at 37° C. overnight in LB containing 100 μg/ml ampicillin. The saturated overnight culture was diluted to 0.03 O.D. at $A_{600}$ in 25 ml of LB containing 100 μg/ml ampicillin and incubated at 37° C. in a 250 ml shake flask. When the culture O.D. reached approximately 0.4, 100 mM IPTG was added for a final concentration of 0.5 mM to induce expression of the recombinant protein. The induced culture was then incubated at 37° C. overnight (~16 h). The induced overnight culture reached an O.D. of 3.3 at $A_{600}$ and 4 O.D.s (1.2 ml) was centrifuged in a Eppendorf model 5415C microfuge at 14,000 rpm for 5 minutes at 4° C. The cell pellet was resuspended to approximately 10 O.D. in ice cold 20% sucrose, 10 mM Tris-HCl pH 8.0 by trituration and vortexing and EDTA pH 8.0 was added for a final concentration of 17 mM. Resuspended cells were incubated on ice for 10 minutes and centrifuged as above. The resultant pellet was resuspended at 10 O.D.s in ice cold water by trituration and vortexing and incubated on ice for 10 minutes. The resuspended cells were then centrifuged as above and the resultant supernatant (soluble periplasmic fraction) and cell pellet (insoluble periplasmic and cell associated components) were analyzed by SDS-PAGE.

The bulk of the rhGH synthesized by BOB132 was found to be soluble and localized to the periplasm. The periplasmic rhGH protein was indistinguishable in size from a purified pituitary hGH standard indicating that the stII signal sequence was removed during protein secretion.

EXAMPLE 3

Purification and Bioactivity of rhGH

A. Purification of Wild-Type rhGH

In order to purify a significant quantity of wild-type rhGH, a 330 ml culture of BOB132 (expressing stII-hGH) was induced, cultured overnight and subjected to osmotic shock based on the preparative procedure described by Hsiung et al. (1986). Specifically, *E. coli* strain W3110 containing the st-II hGH plasmid was grown at 37° C. overnight in LB containing 100 μg/ml ampicillin. The saturated overnight culture was diluted to 0.03 O.D. at $A_{600}$ in 2×250 ml (500 ml total volume) of LB containing 100 μg/ml ampicillin and incubated at 37° C. in 2 L shake flasks. When the culture's O.D. reached approximately 0.4, 100 mM IPTG was added for a final concentration of 0.5 mM to induce expression of the recombinant protein. The induced culture was incubated at 37° C. overnight (~16 h). The induced overnight cultures reached an O.D. of approximately 3.8 at $A_{600}$ and were centrifuged using a Sorval RC-5 centrifuge and a GSA rotor at 8,000 rpm for 5 minutes at 4° C. The cell pellets were combined and resuspended to approximately 47 O.D. in ice cold 20% sucrose, 10 mM Tris-HCl pH 8.0 by trituration and EDTA pH 8.0 was added for a final concentration of ~25 mM. Resuspended cells were incubated on ice for 10 minutes and centrifuged in an IEC Centra MP4R centrifuge with an 854 rotor at 8,500 rpm for 7 minutes at 4° C. The resultant pellets were resuspended at 47 O.D. in ice cold water by trituration and vortexing and incubated on ice for 30 minutes. The resuspended cells were centrifuged in the IEC centrifuge as above and the resultant supernatant (soluble periplasmic fraction) and cell pellet (insoluble periplasmic and cell associated components) were analyzed by SDS-PAGE. Again the gel showed that rhGH produced was soluble, periplasmic, and indistinguishable in size from the pituitary hGH standard.

rhGH was purified in a two step procedure based on that described by Becker and Hsiung (1986). The supernatant from the osmotic shock was loaded onto a 5 ml Pharmacia HiTrap Q Sepharose column equilibrated in 10 mM Tris-HCl pH 8.0 and the bound proteins were eluted with a 15 column volume 50-250 mM linear NaCl gradient. Column fractions were analyzed by SDS-PAGE. Fractions 22-25 eluting at a salt concentration of around 100-125 mM were enriched for hGH, and were pooled, concentrated and further fractionated on a Superdex 200 HR 10/30 sizing column. Fractions 34-36 from the Superdex column (representing MWs around 21-22 kDA based on the elution profile of MW standards) contained most of the rhGH, were pooled and stored as frozen aliquots at −80° C. The final yield of rhGH, as determined by absorbance at 280 nm and by using a Bradford protein assay kit (Bio-Rad Laboratories), was about 2 mg. Non-reduced pituitary hGH migrates with a slightly smaller apparent molecular weight than reduced pituitary hGH when analyzed by SDS-PAGE. This molecular weight change is indicative of proper disulfide bond formation. Our purified rhGH co-migrated with pituitary hGH under both reducing and non-reducing conditions indicating that the rhGH was properly folded and disulfide-bonded. Data presented below indicates that the biological activity of rhGH is indistinguishable from that of pituitary hGH.

B. Bioassay Results for Pituitary hGH and rhGH

The parental FDC-P1 cell line shows a strong proliferative response to mouse IL-3, but not to pituitary hGH. In the absence of IL-3, the majority of FDC-P1 cells die, giving absorbance values less than 0.2. In contrast, FDC-P1 cells transformed with the rabbit growth hormone receptor proliferate in response to pituitary hGH, as evidenced by a dose-dependent increase in cell number and absorbance values. The $EC_{50}$ (protein concentration required to achieve half-maximal stimulation) for this effect ranged from 0.75-1.2 ng/ml pituitary hGH (0.03-0.05 nM) in different experiments, similar to what has been reported in the literature (Rowlinson et al., 1995). A significant difference between the parental FDC-P1 line and FDC-P1 cells transformed with the rabbit growth hormone receptor is that the latter cells survive in the absence of IL-3 or hGH, resulting in higher absorbance values (typically 0.6-1.1, depending upon the assay and length of incubation with MTS in the zero growth factor control wells). The initial pool of rabbit growth hormone receptor transformants and all five independent growth hormone receptor cell lines isolated showed the same effect. A similar result was obtained with a second set of independently isolated rabbit growth hormone receptor transfectants. Rowlinson et al. (1995) observed a similar effect, suggesting that IL-3/GH-independent survival is a consequence of the transformation procedure. Although the growth hormone receptor cell lines did not require IL-3 or hGH for growth, they still showed a robust proliferative response to IL-3 and hGH. The practical effect of the higher absorbance values in the absence of hGH is to decrease the "window" of the hGH response (the difference between the maximum and minimum absorbance values). This window consistently ranged from 40-70% of the zero growth factor values, similar to what was reported by Rowlinson et al. (1995).

Pituitary GH and wild-type rhGH prepared by us had similar dose response curves in the bioassay with $EC_{50}$s ranging from 0.6-1.2 ng/ml in different experiments (Table 1).

TABLE 1

Bioactivities of hGH and hGH Cysteine Muteins

| | Form Assayed | Mean $EC_{50}$ (ng/ml) | $EC_{50}$ Range (ng/ml)[1] |
|---|---|---|---|
| Pituitary hGH | Monomer | 1 +/− 0.1 (N = 11) | 0.75-1.2 |
| RhGH | Monomer | 0.8 +/− 0.3 (N = 3) | 0.6, 0.8, 1.1 |
| T3C | Dimer | 1.4 +/− 0.6 (N = 7) | 0.75-2.5 |
| S144C | Monomer | 1.6 +/− 0.8 (N = 5) | 1.1, 1.1, 1.5, 2.2, 2.7 |
| T148C-lotA | Monomer | 0.5 (N = 2) | 0.4, 0.5 |
| T148C-lotB | Monomer | 2.5 +/− 1.0 (N = 4) | 1.5, 1.9, 3.1, 3.6 |

N/A, not applicable
[1]$EC_{50}$ values from individual experiments. An $EC_{50}$ range is shown when N > 5.

EXAMPLE 4

Construction of hGH Cysteine Muteins

The cysteine substitution mutation T135C was constructed as follows. The mutagenic reverse oligonucleotide BB28 (5>CTGCTTGAAGATCTGCCCACACCG GGGG CTGC-CATC>3) (SEQ.ID.NO. 10) was designed to change the codon ACT for threonine at amino acid residue 135 to a TGT codon encoding cysteine and to span the nearby Bgl II site. This oligo was used in PCR along with BB34 (5>GTAGCG-CAGGCCTTCCCAACC ATT>3) (SEQ.ID.NO. 11) which anneals to the junction region of the ompA-GH fusion gene and is not mutagenic. The PCR was performed in a 50 µl reaction in 1×PCR buffer (Perkin-Elmer buffer containing 1.5 mM $MgCl_2$), 200 µM concentration of each of the four nucleotides dA, dC, dG and dT, with each oligonucleotide primer present at 0.5 µM, 5 pg of pBBT112 (described above) as template and 1.25 units of AmpliTaq DNA Polymerase (Perkin-Elmer) and 0.125 units of Pfu DNA Polymerase (Stratagene). Reactions were performed in a Robocycler Gradient 96 thermal cycler (Stratagene). The program used entailed: 95° C. for 3 minutes followed by 25 cycles of [95° C. for 60 seconds, 45° C. or 50° C. or 55° C. for 75 seconds, 72° C. for 60 seconds] followed by a hold at 6° C. The PCR reactions were analyzed by agarose gel electrophoresis which showed that all three different annealing temperatures gave significant product of the expected size; ~430 bp. The 45° C. reaction was "cleaned up" using the QIAquick PCR Purification Kit (Qiagen) and digested with Bgl II and Pst I. The resulting 278 bp Bgl II-Pst I fragment, which includes the putative T135C mutation, was gel-purified and ligated into pBBT111, the pUC19 derivative carrying the stII-GH fusion gene (described above) which had been digested with Bgl II and Pst I and gel-purified. Transformants from this ligation were initially screened by digestion with Bgl II and Pst I and subsequently one clone was sequenced to confirm the presence of the T135C mutation and the absence of any additional mutations that could potentially be introduced by the PCR reaction or by the synthetic oligonucleotides. The sequenced clone was found to have the correct sequence throughout the Bgl II-Pst I segment.

The substitution mutation S132C was constructed using the protocol described above for T135C with the following differences: mutagenic reverse olignucleotide BB29 (5>CTGCTTGAA GATCTGCCCAGTCCGGGGGCAGC-CATCTTC>3) (SEQ.ID.NO. 12) was used instead of BB28 and the PCR reaction with annealing temperature of 50° C. was used for cloning. One of two clones sequenced was found to have the correct sequence.

The substitution mutation T148C was constructed using an analogous protocol but employing a different cloning strategy. The mutagenic forward oligonucleotide BB30 (5>GGGCAGATCTT CAAGCAGACCTACAGCAAGT-TCGACTGCAACTCACACAAC>3) (SEQ.ID.NO. 13) was used in PCR with the non-mutagenic reverse primer BB33 (5>CGCGGTACCCGGGATCCGATTAGAAT CCA-CAGCT>3) (SEQ.ID.NO. 14) which anneals to the most 3' end of the GH coding sequence and spans the Bam H1 site immediately downstream. PCR was performed as described above with the exception that the annealing temperatures used were 46, 51 and 56° C. Following PCR and gel analysis as described above the 46 and 51° C. reactions were pooled for cloning. These were digested with Bam H1 and Bgl II and the resulting 188 bp fragment was gel-purified and cloned into pBBT111 which had been digested with Bam H1 and Bgl II, treated with calf alkaline phosphatase (Promega) according to the vendor protocols, and gel-purified. Tranformants from this ligation were analyzed by digestion with Bam H1 and Bgl II to identify clones in which the 188 bp Bam H1-Bgl II mutagenic PCR fragment was cloned in the proper orientation: because Bam H1 and Bgl II generate compatible ends, this cloning step is not orientation specific. Five of six clones tested were shown to be correctly oriented. One of these was sequenced and was shown to contain the desired T148C mutation. The sequence of the remainder of the 188 bp Bam H1-Bgl II mutagenic PCR fragment in this clone was confirmed as correct.

The construction of the substitution mutation S144C was identical to the construction of T148C with the following exceptions. Mutagenic forward oligonucleotide BB31 (5>GGGCAGATCT TCAAGCAGACCTACTGCAAGTTC-GAC>3) (SEQ.ID.NO. 15) was used instead of BB30. Two of six clones tested were shown to be correctly oriented. One of these was sequenced and was shown to contain the desired S144C mutation. The sequence of the remainder of the 188 bp Bam H1-Bgl II mutagenic PCR fragment in this clone was also confirmed as correct.

A mutation was also constructed that added a cysteine residue to the natural carboxyterminus of GH. The construction of this mutation, termed stp192C, was carried out using the procedures described above for construction of the T148C mutein but employed different oligonucleotide primers. The mutagenic reverse oligonucleotide BB32 (5>CGCGGTAC-CGGATCCTTAGCAGAAGCCACAG CTGCCCTC-CAC>3) (SEQ.ID.NO. 16) which inserts a TGC codon for cysteine between the codon for the carboxy terminal phe residue of GH and the TAA translational stop codon and spans the nearby Bam H1 site was used along with BB34 which is described above. Following PCR and gel analysis as described above the 46° C. reaction was used for cloning. Three of six clones tested were shown to be correctly oriented. One of these was sequenced and was shown to contain the desired stp192C mutation. The sequence of the remainder of the 188 bp Bam H1-Bgl II mutagenic PCR fragment in this clone was confirmed as correct.

The substitution mutation S100C was constructed using mutagenic reverse oligonucleotide BB25 (5>GTCAGAG-GCGCCGTACACCAGGCAGTTGGCGAAGAC>3) (SEQ.ID.NO. 17) which alters the AGC codon for serine at amino acid residue 100 to a TGC codon encoding cysteine. BB25 also spans the nearby Nar I site. PCR reactions using BB25 and BB34 were carried out using the PCR protocol described above for the construction of the T135C mutation. Following gel analysis of the PCR products, the product of the 50° C. annealing reaction was cleaned up using the QIAquick PCR Purification Kit (Qiagen), with digested with Pst I and Nar I. The resulting 178 bp fragment was gel-purified and ligated into pBBT111 which had been digested with Pst I and Nar I and gel-purified. Plasmids isolated from transformants from this ligation were screened by digestion with Pst I and Nar I and subsequently one plasmid was sequenced to confirm the presence of the S100C mutation and the absence of any other mutations in the 178 bp Pst I-Nar I segment.

The substitution mutation A98C was constructed using the procedure described above for S100C with the following differences: the mutagenic reverse oligonucleotide BB26 (5>GTCAG AGGCGCCGTACACCAGGCTGTTGCA-GAAGACACTCCT>3) (SEQ.ID.NO. 18) was used for PCR in place of BB25 and the PCR reaction performed with an annealing temperature of 45° C. was used for cloning. One clone was sequenced and found to have the correct sequence.

The substitution mutation A34C was constructed as follows. The mutagenic reverse oligo BB23 (5>GCGCTGCAG-GAATGAATACTTCTGTTCCTTTGG-GATATAGCATTCTTC AAACTC>3) (SEQ.ID.NO. 19) was designed to change the GCC codon for alanine at amino acid residue 34 to a TGC codon encoding cysteine and to span the Pst I site. This oligonucleotide was used in PCR reactions along with BB11 (5>CCCCCTCTAGACAT ATGAAGAA-GAACATCGC ATTCCTGCTGGCATCTATGT-TCGTTTTCTCTATCG>3) (SEQ.ID.NO. 20) which anneals to the 5' end of the coding sequence of the stII leader sequence and spans the Nde I site that overlaps the initiator methionine codon.

PCR reactions were performed in 50 l in 1×PCR buffer (Promega) containing 1.5 mM MgCl$_2$, 200 µM concentration of each of the four nucleotides dA, dC, dG and dT, with each oligonucleotide primer present at 0.2 M, 1 ng of pBBT111 (described above) as template and 0.8 units of Tac DNA Polymerase (Promega) and 0.33 units of Pfu DNA Polymerase (Stratagene). Reactions were performed in a Robocycler Gradient 96 thermal cycler (Stratagene). The program used entailed: 96° C. for 3 minutes followed by 25 cycles of [95° C. for 60 seconds, 50° C. or 55° C. or 60° C. for 75 seconds, 72° C. for 60 seconds] followed by a hold at 6° C. The PCR reactions were analyzed by agaraose gel electrophoresis which showed that all three different annealing temperatures gave significant product of the expected size; ~220 bp. The 50 and 55° C. reactions were pooled, "cleaned up" using the QIAquick PCR Purification Kit (Qiagen) and digested with Nde I and Pst I. The resulting 207 bp Nde I-Pst I fragment, which includes the putative A34C mutation, was gel-purified and ligated into pBBT111, which had been digested with Nde I and Pst I, treated with alkaline phosphatase, and gel-purified. Transformants from this ligation were initially screened by digestion with Nde I and Pst I and subsequently one clone was sequenced to confirm the presence of the A34C mutation and the absence of any additional mutations that could potentially be introduced by the PCR reaction or by the synthetic oligonucleotides. The sequenced clone was found to have the correct sequence throughout the Nde I-Pst I segment.

The substitution mutation S43C was constructed using the protocol described above for A34C with the following differences: mutagenic reverse oligonucleotide BB24

(5>GCGCTG CAGGAAGCAATACTTCTGTTC-CTTTGG>3) (SEQ.ID.NO. 21) was used instead of BB23. One clone was sequenced and shown to contain the correct sequence.

The substitution mutation T3C was constructed using two sequential PCR steps. The first step created the desired mutation while the second step extended the PCR product of the first reaction to encompass a useful cloning site. The mutagenic forward oligonucleotide BB78 (5>GCAT CTAT-GTTCGTTTTCTCTATCGCTACCAACGCT TACGCAT-TCCCATGCATTCCCT TATCCAG>3) (SEQ.ID.NO. 22) was designed to change the ACC codon for threonine at amino acid residue 3 to a TGC codon encoding cysteine and to span and anneal to the junction of the stII-hGH fusion gene. BB78 was used in the first step PCR along with BB33 which is described above.

The first PCR reaction was performed in 50 µl in 1×PCR buffer (Promega) containing 1.5 mM $MgCl_2$, 200 µM concentration of each of the four nucleotides dA, dC, dG and dT, each oligonucleotide primer at 0.2 µM, 1 ng of pBBT111 (described above) as template and 1.5 units of Tac DNA Polymerase (Promega) and 0.25 units of Pfu DNA Polymerase (Stratagene). Reactions were performed in a Robocycler Gradient 96 thermal cycler (Stratagene). The program used entailed: 96° C. for 3 minutes followed by 25 cycles of [94° C. for 60 seconds, 60° C. for 75 seconds, 72° C. for 60 seconds] followed by a hold at 6° C. The PCR reaction was ethanol precipitated and the ~630 bp product was gel-purified and recovered in 20 µl 10 mM Tris-HCl (pH 8.5). An aliquot of this gel-purified fragment was diluted 100-fold and 2 µl of the diluted fragment was used as template in the second PCR step. The second PCR step employed oligonucleotides BB11 and BB33 (both described above) and used the reaction conditions employed in the first step PCR reaction. The second step PCR reaction was analyzed by agarose gel electrophoresis and the expected ~670 bp fragment was observed. The PCR reaction was "cleaned up" using the QIAquick PCR Purification Kit (Qiagen) and digested with Nde I and Pst I. The resulting 207 bp Nde I-Pst I fragment, which includes the putative T3C mutation, was gel-purified and ligated into pBBT111, which had been digested with Nde I and Pst I, treated with alkaline phosphatase, and gel-purified. Transformants from this ligation were initially screened by digestion with Nde I and Pst I and subsequently one clone was sequenced to confirm the presence of the T3C mutation and the absence of any additional mutations that could potentially be introduced by the PCR reaction or by the synthetic oligonucleotides. The sequenced clone was found to have the correct sequence throughout the Nde I-Pst I segment.

The substitution mutation A105C was constructed using the technique of "mutagenesis by overlap extension" as described in general by Horton, R. M. pp 251-261 in Methods in Molecular Biology, Vol. 15: PCR Protocols: Current Methods and Applications edited by White, B. A. (1993) Humana Press, Inc., Totowa, N.J. With this technique two separate fragments are amplified from the target DNA segment as diagrammed in FIG. 1. One fragment is produced with primers a and b to yield product AB. The second primer pair, c and d, are used to produce product CD. Primers b and c introduce the same sequence change into the right and left ends of products AB and CD, respectively. Products AB and CD share a segment of identical (mutated) sequence, the "overlap", which allows annealing of the top strand of AB to the bottom strand of CD, and the converse. Extension of these annealed overlaps by DNA polymerase in a subsequent PCR reaction using primers a and d with products AB and CD both added as template creates a full length mutant molecule AD.

With the exception of the use of different oligonucleotide primers, the initial PCR reactions for the A105C construction were performed identically to those described in the construction of T3C above. The primer pairs used were: (BB27+BB33) and (BB11+BB79). BB11 and BB33 are described above. BB27 and BB79 are complementary mutagenic oligonucleotides that change the GCC codon for alanine at amino acid residue 105 to a TGC codon encoding cysteine. The sequence of BB27 is (5>AGCCTGGTGTAC GGCTGCTCT-GACAGCAACGTC>3) (SEQ.ID.NO. 23) and the sequence of BB78 is 5>GACGTTGCTG TCAGAGCAGCCGTACAC-CAGGCT>3 (SEQ.ID.NO. 24). The (BB27×BB33) and (BB11×BB79) PCR reactions were ethanol precipitated, gel-purified, and recovered in 20 µl 10 mM Tris-HCl (pH 8.5). The preparative gel showed that the predominant product from each PCR reaction was of the expected size: ~290 bp for the (BB27×BB33) reaction and ~408 bp for the (BB11×BB79) reaction. These two mutagenized fragments were then "spliced" together in a subsequent PCR reaction. In this reaction 1 µl of each of gel-purified fragments from the initial reactions were added as template and BB11 and BB33 were used as primers. Otherwise, the PCR reaction was performed using the same conditions employed for the initial (BB27×BB33) and (BB11×BB79) reactions. An aliquot of the secondary PCR reaction was analyzed by agarose gel electrophoresis and the expected ~670 bp band was observed. The bulk of the PCR reaction was then "cleaned up" using the QIAquick PCR Purification Kit (Qiagen) and digested with Bgl II and Pst I. The resulting 276 bp Bgl II-Pst I fragment, which includes the putative A105C mutation, was gel-purified and ligated into pBBT111, which had been digested with Bgl II and Pst I, and gel-purified. Transformants from this ligation were initially screened by digestion with Bgl II and Pst I and subsequently one clone was sequenced to confirm the presence of the A105C mutation and the absence of any additional mutations that could potentially be introduced by the PCR reaction or by the synthetic oligonucleotides. The sequenced clone was found to have the correct sequence throughout the Bgl II-Pst I segment.

For expression in *E. coli* as proteins secreted to the periplasmic space, the stII-hGH genes encoding the 11 muteins were excised from the pUC19-based pBBT111 derivatives as Nde I-Xba I fragments of ~650 bp and subcloned into the pCYB1 expression vector that had been used to express rhGH. For expression experiments, these plasmids were introduced into *E. coli* W3110.

Using procedures similar to those described here and in Example 23, one can construct other cysteine muteins of GH. The cysteine muteins can be substitution mutations that substitute cysteine for a natural amino residue in the GH coding sequence, insertion mutations that insert a cysteine residue between two naturally occurring amino acids in the GH coding sequence, or addition mutations that add a cysteine residue preceding the first amino acid, F1, of the GH coding sequence or add a cysteine residue following the terminal amino acid residue, F191, of the GH coding sequence. The cysteine residues can be substituted for any amino acid, or inserted between any two amino acids, anywhere in the GH coding sequence. Preferred sites for substituting or inserting cysteine residues in GH are in the region preceding Helix A, the A-B loop, the B-C loop, the C-D loop and the region distal to Helix D. Other preferred sites are the first or last three amino acids of the A, B, C and D Helices. Preferred residues in these regions for creating cysteine substitutions are F1, P2, P5, E33, K38, E39, Q40, Q46, N47, P48, Q49, T50, S51, S55, S57, T60, Q69, N72, N99, L101, V102, Y103, G104, 5106, E129, D130, G131, P133, R134, G136, Q137, K140, Q141, T142, Y143, K145, D147, N149, 5150, H151, N152, D153, 5184, E186, G187, 5188, and G190. Cysteine residues also can be inserted immediately preceding or following these amino acids. One preferred site for adding a cysteine residue would be preceding F1, which is referred to herein as *–1C.

One also can construct GH muteins containing a free cysteine by substituting another amino acid for one of the naturally-occurring cysteine residues in GH. The naturally occurring cysteine residue that normally forms a disulfide bond with the substituted cysteine residue is now free. The non-essential cysteine residue can be replaced with any of the other 19 amino acids, but preferably with a serine or alanine residue. A free cysteine residue also can be introduced into GH by chemical modification of a naturally occurring amino acid using procedures such as those described by Sytkowski et al. (1998), incorporated herein by reference.

Using procedures similar to those described in Examples 1-15, one can express the proteins in prokaryotic cells such as *E. coli*, purify the proteins, PEGylate the proteins and measure their bioactivities in an in vitro bioassay. The GH muteins also can be expressed in eukaryotic cells such as insect or mammalian cells using procedures similar to those described in Examples 16-19, or related procedures well known to those skilled in the art. If secretion is desired, the natural GH signal sequence, or another signal sequence, can be used to secrete the protein from eukaryotic cells.

EXAMPLE 5

Cystine Addition Improves Recovery of Cysteine Mutein T3C

*E. coli* strain W3110 containing the T3C mutation was grown overnight in 3 ml of LB containing 100 μg/ml ampicillin. The saturated overnight culture was diluted to 0.03 O.D. at $A_{600}$ in 300 ml of LB containing 100 μg/ml ampicillin and incubated at 37° C. in 2 L shake flasks. When the culture O.D. reached 0.420, 1.5 ml of 100 mM IPTG was added for a final concentration of 0.5 mM to induce expression of the recombinant protein. The induced culture was incubated at 37° C. overnight (~16 h).

The induced overnight culture reached an O.D of 3.6 at $A_{600}$ and was split into 2×135 ml volumes and centrifuged using a Sorval RC-5 centrifuge with a GSA rotor at 8,000 rpm for 10 minutes at 4° C. The supernatants were discarded and the cell pellets subjected to osmotic shock treatment as follows. The cell pellets were resuspended to approximately 49 O.D. in 10 ml of ice cold Buffer A [20% sucrose, 10 mM Tris-HCl pH 7.5] or Buffer B [20% sucrose, 10 mM Tris-HCl pH 7.5, 5.5 mM cystine (pH adjusted to 7.5-8.0)]. The pellets were resuspended by trituration and vortexing and 1 ml of 0.25 M EDTA pH 8.0 was added to give a final concentration of ~25 mM. Resuspended cells were incubated on ice for 30 minutes and centrifuged in an SS-34 rotor at 8,500 rpm for 10 minutes at 4° C. The supernatants were discarded and the pellets resuspended by trituration and vortexing in 10 ml of ice cold Buffer C [5 mM Tris-HCl pH 7.5] or Buffer D [5 mM Tris-HCl pH 7.5, 5 mM cystine (pH adjusted to 7.5-8.0)] and incubated on ice for 30 minutes. The resuspended cell pellet was centrifuged in an SS-34 rotor at 8,500 rpm for 10 minutes at 4° C. and the resultant supernatant (soluble periplasmic fraction) was recovered and stored at –80° C. SDS-PAGE analysis of the various supernatants revealed that by incorporating cystine into the osmotic shock procedure, the amount of monomeric hGH species recovered in the soluble periplasmic fraction can be significantly improved. In the sample treated with cystine, we observed that a majority of the hGH ran as a single band of about 22 kDa on a non-reduced SDS-PAGE gel and that band co-migrated with pituitary hGH. In the absence of cystine, a number of different molecular weight species were observed in the monomeric range. Larger molecular weight protein aggregates are visible when the gel is developed using Western blotting.

EXAMPLE 6

General Method for Expression and Purification of GH Cysteine Added Variants

A standard protocol for isolation of the hGH cysteine muteins is as follows. Cultures of W3110 *E. coli* strains containing the stII-hGH mutein plasmids were grown to saturation in LB containing 100 μg/ml ampicillin at 37° C. The overnight cultures were typically diluted to 0.025-0.030 O.D. at $A_{600}$ in LB containing 100 μg/ml ampicillin and grown at 37° C. in shake flasks. When culture O.D.'s reached 0.300-0.500 at $A_{600}$, IPTG was added to a final concentration of 0.5 mM to induce expression. The induced cultures were incubated at 37° C. overnight. Induced overnight cultures were pelleted by centrifugation in a Sorval RC-5 centrifuge at 8,000-10,000×g for 10 minutes at 4° C. and the resultant pellets subjected to osmotic shock based on the procedures of Koshland and Botstein (1980) or Hsiung et al., (1986) depending on the size of the culture. For osmotic shock, cell pellets were resuspended at 25-50 O.D. in 20% sucrose, 10 mM Tris-HCl pH7.5. In certain instances 5 or 25 mM EDTA pH 8.0 and/or 5 mM cystine (pH adjusted to 7.5-8.0) were included in the resuspension buffer. The resuspended pellets were incubated on ice for 15-30 minutes and centrifuged as above. The supernatants were discarded and the pellets resuspended at 25-50 O.D. at $A_{600}$ in 5 or 10 mM Tris-HCl pH 7.5. In certain instances 5 mM EDTA pH 8.0 and/or 5 mM cystine (pH adjusted to 7.5-8.0) were included in the resuspension buffer. The resuspended pellets were incubated on ice for 30 minutes and centrifuged as above. The resulting supernatant contains the soluble periplasmic components and the pellet is comprised of insoluble periplasmic, and cell associated components.

Addition of cystine to the osmotic shock buffer resulted in significantly improved recoveries and stabilization of many of the cysteine muteins. In the presence of cystine the cysteine muteins were largely monomeric, whereas in the absence of cystine, a mixture of hGH monomers, dimers and higher order aggregates were observed when the samples were analyzed by non-reducing SDS-PAGE and Western blots. Presumably the higher order aggregates are a consequence of the added cysteine residues in the proteins since they were greatly reduced or absent with wild-type rhGH. Addition of cystine to the osmotic shock buffer largely solved this problem. We believe cystine reacts with the free cysteine residue in the muteins to form a stable mixed disulfide, thus preventing disulfide shuffling and aggregation. We have also tested a second dithiol, cystamine and have seen a similar stabilizing effect on cysteine muteins of hGH. Presumably other dithiols such as oxidized glutathione would also lead to improved recoveries of proteins containing a free cysteine.

Of the 11 hGH muteins analyzed, six expressed at levels sufficient for isolation and purification. Non-reduced SDS-PAGE analysis of the osmotic shock supernatants for the A34C, S43C, A98C, S100C and S132C muteins showed little or no protein present at the correct molecular weight. Addition of cystine did not discernibly improve recovery of these proteins. The relatively low expression levels of these muteins makes it difficult to observe improved yields. Preliminary analyses of whole cell lysates indicated that these mutant proteins were expressed, but insoluble. The T3C, A105C, T135C, S144C, T148C and stp192C muteins showed moderate to good expression levels. Five of these cysteine muteins (T3C, T135C, S144C, T148C and stp192C) showed significantly improved recoveries when cystine was present in the osmotic shock buffer. A105C was not tested in the absence of cystine. General protein purification protocols are described below.

WT-rhGH was purified by ion exchange and gel filtration chromatography. The cysteine muteins were purified by an assortment of chromatographic procedures including ion exchange, hydrophobic interaction (HIC), metal chelation affinity chromatographies (IMAC), Size Exclusion Chromatography (SEC) or a combination of these techniques. Generally, the hGH mutein was captured from the fresh osmotic shock supernatant using a Q-Sepharose fast flow resin (Pharmacia) equilibrated in 20 mM Tris-HCl, pH 8.0. The column was washed with 20 mM Tris-HCl, pH 8.0 and bound proteins eluted with a linear 10 volume increasing salt gradient from 0 to 250 mM NaCl in 20 mM Tris-HCl, pH 8.0. Fractions containing the hGH muteins were identified by SDS-PAGE and Western blotting. These fractions were pooled and stored frozen. Alternative resins can be used to capture hGH muteins from the osmotic shock mixture. These include HIC, cation ion exchange resins or affinity resins.

For hydrophobic interaction chromatography (HIC), the Q column pool was thawed to room temperature and NaCl added to a final concentration of 2 M. The pool was loaded onto the Butyl-Sepharose fast flow resin previously equilibrated in 2 M NaCl, 20 mM sodium phosphate, pH 7.5. hGH muteins were eluted from the resin using a reverse salt gradient form 2 M to 0 M NaCl in 20 mM phosphate, pH 7.5. Fractions containing the hGH muteins were identified by SDS-PAGE and Western blotting, and pooled.

In some instances, the HIC pool was subsequently loaded directly onto a nickel chelating resin (Qiagen) equilibrated in 10 mM sodium phosphate, 0.5 M NaCl, pH 7.5. Following a wash step, muteins were recovered using a 0-30 mM imidizole gradient in 10 mM sodium phosphate, 0.5 M NaCl, pH 7.5. hGH has a high affinity for nickel, presumably through the divalent metal-binding site formed by H18, H21 and E174. As a result, hGH can be obtained in highly pure form using a metal chelation column (Maisano et al., 1989). All of the muteins tested bound tightly to the nickel column and eluted at similar imidazole concentrations (around 15 mM) as wild-type rhGH.

EXAMPLE 7

Purification of T3C

The soluble periplasmic fraction prepared in the presence of cystine (Example 5) was loaded onto a 1 ml HiTrap Q-Sepharose column (Pharmacia Biotech, Uppsala, Sweden) equilibrated in 10 mM Tris-HCl pH 8.0 and the bound proteins were eluted with a 20 column volume linear gradient of 0-250 mM NaCl. The column load and recovered fractions were analyzed by 14% SDS-PAGE. T3C eluted at a salt concentration around 170-200 mM which was significantly later than WT-hGH. Surprisingly, T3C mutein was present in a monomeric form when loaded on the column, but was recovered predominantly as a stable disulfide linked homodimer following elution from the Q column. When reduced, the T3C mutein co-migrated on a SDS-PAGE gel with wild type hGH. Dimer formation occurred during the Q column purification step. Cystine was not present in the Q column buffer or the buffers used for the other column steps. The T3C dimer remained intact throughout any further concentration or purification procedures. The pool from the Q column was adjusted to a final NaCl concentration of 0.5 M and loaded onto 1 ml Ni-agarose column (Qiagen) previously equilibrated in 10 mM sodium phosphate, 0.5 M NaCl, pH 7.5. Following a wash step, highly purified T3C dimers were recovered using a 0-30 mM imidizole gradient in 10 mM sodium phosphate, 0.5 M NaCl, pH 7.5. T3C dimers were active in the bioassay (Example 10 and Table 1).

The A105C, T135C and stp192C muteins also were recovered from the Q column as disulfide-linked dimers. It appears that certain muteins are capable of forming stable disulfide-linked dimers, presumably through the added cysteine residue, once cystine is removed. We believe monomeric forms of these proteins could be stabilized by including cystine or other dithiol compounds and/or cysteine blocking agents in all the column buffers and/or maintaining the pH of the buffers below 7 to prevent disulfide rearrangement.

EXAMPLE 8

Purification of T148C

E. coli strain W3110 expressing the T148C mutein was grown overnight in 3 ml of LB containing 100 µg/ml ampicillin. The saturated overnight culture was diluted to 0.025 O.D. at $A_{600}$ in 500 ml of LB containing 100 µg/ml ampicillin and divided into 2×250 ml volumes and incubated at 37° C. in 2 L shake flasks. When the culture O.D. reached approximately 0.35, 1.25 ml of 100 mM IPTG was added to each flask for a final concentration of 0.5 mM to induce expression of the recombinant protein. The induced culture was incubated at 37° C. overnight (~16 h).

The induced overnight cultures reached an O.D of approximately 3.5 at $A_{600}$ and were centrifuged using a Sorval RC-5 centrifuge with a GSA rotor at 8,000 rpm for 10 minutes at 4° C. The supernatants were discarded and the cell pellets subjected to osmotic shock treatment as follows. The cell pellets were resuspended to approximately 43 O.D. in ice cold 20% sucrose, 10 mM Tris-HCl pH 7.5, 5.0 mM EDTA pH 8.0, 5.0 mM cystine (pH adjusted to 7.5-8.0) by trituration and vortexing. Resuspended cells were incubated on ice for 15 minutes, centrifuged in Sorval centrifuge with an SS-34 rotor at 8,500 rpm for 10 minutes at 4° C. The supernatants were discarded and the pellets resuspended to approximately 43 O.D. in ice cold 1 mM Tris-HCl pH 7.5, 5 mM EDTA pH 8.0, 5 mM cystine (pH adjusted to 7.5-8.0) by trituration and vortexing. Resuspended cells were incubated on ice for 30 minutes and centrifuged in an SS-34 rotor at 8,500 rpm for 10 minutes at 4° C. and the resultant supernatant (soluble periplasmic fraction) was recovered and stored at −80° C.

A second culture of T148C was prepared in a similar manner with the following exceptions: 1) the induced culture volume was 200 ml and reached an O.D. of approximately 4.0 at $A_{600}$ after overnight incubation at 37° C., and 2) The cell pellet resuspensions were done at approximately 30 O.D.s at $A_{600}$.

The soluble periplasmic fraction from the above preparations were combined and dialyzed against 1 L of 10 mM Tris-HCl pH 8.0 overnight at 4° C. The dialysis retentate was loaded onto a 5 ml HiTrap Q-Sepharose column (Pharmacia Biotech, Uppsala, Sweden) equilibrated in 10 mM Tris-HCl pH 8.0 and the bound proteins were eluted with a 20 column volume linear gradient of 0-250 mM NaCl. Column fractions were analyzed by 14% SDS-PAGE (Novex, San Diego, Calif.). T148C mutein eluted as a sharp peak at a salt concentration around 60-80 mM. The appropriate fractions were pooled and concentrated on Centricon 10 concentrators (Amicon, Inc., Beverly, Mass.). The concentrated pool was further purified on a Superdex 200 HR 10/30 column (Pharmacia Biotech Inc., Uppsala, Sweden.) equilibrated in 20 mM sodium phosphate pH 7.5, 150 mM NaCl. The column fractions were again analyzed by SDS-PAGE and the T148C mutein containing fractions were pooled. We observed that the T148C remained monomeric after recovery from the Q-Sepharose column and eluted from the Superdex column at a molecular weight similar to wild type hGH. T148C prepared by Q-Sepharose and size exclusion chromatography is referred to as Lot A.

Alternatively the Q-pool can be loaded directly onto a nickel chelating resin (Qiagen) equilibrated in 10 mM sodium phosphate, 0.5 M NaCl, pH 7.5. Following a wash step, T148C was recovered using a 0-30 mM imidizole gradient in 10 mM sodium phosphate, 0.5 M NaCl, pH 7.5. T148C protein prepared by Q-Sepharose and nickel affinity chromatography is referred to as Lot B.

An osmotic shock T148C supernatant was prepared in the absence of cystine and purification over a Q-Sepharose column was attempted. The identical protocol was followed as described above except cystine was absent from the osmotic shock buffers. The T148C protein product eluted from the Q column over a broad range of salt concentrations, recoveries were lower and the protein preparation was substantially less pure than the cystine treated T148C sample.

EXAMPLE 9

Purification of S144C

E. coli strain W3110 containing the S144C mutation was grown overnight in 3 ml of LB containing 100 μg/ml ampicillin. The saturated overnight culture was diluted to 0.03 O.D.s at $A_{600}$ in 250 ml of LB containing 100 μg/ml ampicillin and incubated at 37° C. in a 2 L shake flask. When the culture O.D. reached approximately 0.3, 1.25 ml of 100 mM IPTG was added for a final concentration of 0.5 mM to induce expression of the recombinant protein. The induced culture was incubated at 37° C. overnight (~16 h).

The induced overnight culture reached an O.D of approximately 3.3 at $A_{600}$ and was centrifuged using a Sorval RC-5 centrifuge with a GSA rotor at 8,000 rpm for 10 minutes at 4° C. The supernatant was discarded and the cell pellet subjected to osmotic shock treatment as follows. The cell pellet was resuspended to approximately 33 O.D. in ice cold 20% sucrose, 10 mM Tris-HCl pH 7.5, 5.0 mM cystine (pH adjusted to 7.5-8.0) by trituration and vortexing and 0.25 M EDTA pH 8.0 was added to a final concentration of 25 mM. Resuspended cells were incubated on ice for 30 minutes, centrifuged in the Sorval RC-5 centrifuge with an SS-34 rotor at 8,500 rpm for 10 minutes at 4° C. The supernatants were discarded and the pellets resuspended to approximately 33 O.D.s in ice cold 5 mM Tris-HCl pH 7.5, 5 mM cystine (pH adjusted to 7.5-8.0) by trituration and vortexing. Resuspended cells were incubated on ice for 30 minutes and centrifuged in an SS-34 rotor at 8,500 rpm for 10 minutes at 4° C. and the resultant supernatant (soluble periplasmic fraction) was recovered and stored at −80° C.

The soluble periplasmic fraction from the above preparation was loaded onto a 5 ml HiTrap Q-Sepharose column (Pharmacia Biotech, Uppsala, Sweden) equilibrated in 10 mM Tris-HCl pH 8.0 and the bound proteins were eluted with a 20 column volume linear gradient of 0-250 mM NaCl. Column fractions were analyzed by 14% SDS-PAGE (Novex, San Diego, Calif.) and S144C mutein-containing fractions, 125-150 mM NaCl, were pooled and frozen. The S144C mutein was monomeric.

EXAMPLE 10

Bioactivities of hGH Cysteine Muteins

The biological activities of the purified T3C, S144C and T148C cysteine muteins were measured using the cell proliferation assay described in Example 1. Protein concentrations were determined using a Bradford assay. All three muteins were biologically active. All of the muteins reached the same level of maximum stimulation as pituitary hGH, within the error of the assay. The mean $EC_{50}$s for the T3C, S144C and T148C muteins were similar to that of pituitary hGH and rhGH (Table 1). Two independent preparations of the T148C mutein and one preparation each of the S144C and T3C muteins (all prepared in the presence of cystine) have been assayed multiple times (Table 1). The partially purified A105C, T135C and stp192C muteins also have been assayed and are biologically active.

EXAMPLE 11

General Methods for Pegylation and Purification of Cysteine Muteins

GH muteins can be PEGylated using a variety of cysteine-reactive PEG-maleimide (or PEG-vinylsulfone) reagents that are commercially available. Generally, methods for PEGylating the proteins with these reagents will be similar to those described in WO 9412219 (Cox and McDermott) and WO 9422466 (Cox and Russell), both incorporated herein by reference, with minor modifications. The recombinant proteins are generally partially reduced with dithiothreitol (DTT), Tris (2-carboxyethyl)phosphine-HCl (TCEP) or some other reducing agent in order to achieve optimal PEGylation of the free cysteine. The free cysteine is relatively unreactive to cysteine-reactive PEGs unless this partial reduction step is performed. The amount of reducing agent required to partially reduce each mutein can be determined empirically, using a range of reducing agent concentrations at different pHs and temperatures. Reducing agent concentrations typically vary from 0.5 equal molar to 10-fold excess. Preferred temperatures are 4° C. to 37° C. The pH can range from 6.5 to 9.0 but is preferrably 7.5 to 8.5. The optimum conditions will also vary depending on the reductant and time of exposure. Under the proper conditions, the least stable disulfides (typically intermolecular disulfides and mixed disulfides) are disrupted first rather than the more thermodynamically stable native disulfides. Typically, a 5-10 fold molar excess of DTT for 30 minutes at room temperature is effective. Partial reduction can be detected by a slight shift in the elution profile of the protein from a reversed-phase column. In the case of a dimeric hGH, a shift in molecular weight is visible by SDS-PAGE analysis run under non-reducing condition. Care must be taken not to over-reduce the protein and expose additional cysteine residues. Over-reduction can be detected by reversed phase-HPLC (the over-reduced protein will have a retention time similar to the fully reduced and denatured protein) and by the appearance of GH molecules containing two PEGs following the PEGylation reaction (detectable by a molecular weight change on SDS-PAGE). Wild type GH can serve as a control since it should not PEGylate under conditions that do not reduce the native intramolecular disulfides. Excess reducing agent can be removed prior to PEGylation by size exclusion chromatography or by dialysis. TCEP need not be removed before addition of the PEGylation reagent as it is does not contain a free thiol group. The partially reduced protein can be reacted with various concentrations of PEG-maleimide or PEG-vinylsulfone (typically PEG:protein molar ratios of 1:1, 5:1, 10:1 and 50:1) to determine the optimum ratio of the two reagents. PEGylation of the protein can be monitored by a molecular weight shift for example, using SDS-PAGE. The lowest amount of PEG that gives significant quantities of mono-pegylated product without giving di-pegylated product is typically considered optimum (80% conversion to mono-pegylated product is generally considered good). Generally, mono-PEGylated protein can be purified from non-PEGylated protein and unreacted PEG by size-exclusion, ion exchange, affinity, reversed phase, or hydrophobic interaction chromatography. Other purification protocols such as 2-phase organic extraction or salt precipitation can be used. The purified PEGylated protein can be tested in the cell proliferation assay described in Example 1 to determine its specific activity.

Experiments can be performed to confirm that the PEG molecule is attached to the protein at the proper site. This can be accomplished by chemical or proteolytic digestion of the protein, purification of the PEGylated peptide (which will have a large molecular weight) by size exclusion, ion exchange or reversed phase chromatography, followed by amino acid sequencing. The PEG-coupled amino acid will appear as a blank in the amino acid sequencing run.

EXAMPLE 12

Preparation and Purification of PEG-T3C

A preliminary titration study was performed to determine appropriate reducing agent and PEG reagent concentrations and to avoid over-reduction of the protein. We monitored partial reduction of the protein by conversion of dimer to non-reduced monomer species on non-reduced SDS-PAGE. One µg aliquots of purified T3C dimer were incubated with increasing concentrations of TCEP for 60 minutes at room temperature. The reactions were immediately analyzed by non-reducing SDS-PAGE. The amount of TCEP that yielded significant amounts of monomer T3C without overreducing and denaturing the protein was used for subsequent experiments. TCEP is a convenient reducing agent for small scale experiments because it does not interfere with the PEGylation reaction; thus the protein:TCEP mixture did not have to be dialyzed prior to PEG addition. At a larger scale inexpensive reducing agents such as DTT are preferred for reducing proteins. Generally, the protein is treated with a reducing agent for an optimal amount of time. The pH of the reaction is then adjusted to 6.5 or below to limit disulfide rearrangements. The reducing agent is removed by dialysis or liquid chromatography. The pH is then readjusted to greater than 6.5 or preferably 7.5 to 8.5 and the PEG reagent is added.

The titration experiments at pH 7.5 indicated that a five-fold molar excess of TCEP for 60 minutes at room temperature converted the majority of the T3C dimer species into properly disulfide-bonded monomer without over reducing the protein. Control experiments indicated that, as expected, the T3C dimer needed to be reduced with TCEP to be PEGylated. These reaction conditions were then scaled to 100 µg reaction scale. A 10-fold molar excess of 5 kDa maleimide-PEG (Fluka) was added to the T3C:TCEP mixture after 10 minutes and the PEGylation reaction was allowed to proceed for 60 minutes at room temperature. The sample was loaded quickly onto a 1 ml Q-Sepharose column equilibrated in 20 mM Tris-HCl, pH 8.0. The column was washed with 20 mM Tris-HCl, pH 8.0 and bound proteins eluted with a linear 10 volume increasing salt gradient from 0 to 250 mM NaCl in 20 mM Tris-HCl, pH 8.0. Fractions containing mono-PEGylated T3C (a single PEG molecule attached to the T3C monomer) were identified by SDS-PAGE and Western blotting. These fractions were pooled and stored frozen. The presence of the PEG moiety decreases the protein's affinity for the resin, allowing the PEGylated protein to be separated from the non-PEGylated protein.

EXAMPLE 13

PEGylation of S144C and other Cysteine Muteins

A preliminary titration study was also performed for S144C to determine appropriate reducing agent, PEG reagent concentrations and to avoid over-reduction of the protein as described in Example 12 for T3C. The larger scale PEGylation was carried out at pH 7.5 at room temperature for 2 h using a 2-fold molar excess of TCEP and a 10-fold molar excess of 5 kDa maleimide-PEG. SDS-PAGE analysis of the reaction mixture showed some species with two or more PEGs present. These were separated from the mono-PEGylated S144C using a Q-Sepharose column as described in Example 12. Separately we performed a PEGylation reaction using 5 kDa vinylsulfone-PEG (Fluka) which resulted in monopegylated S144C under identical reducing conditions.

We have also performed small scale PEGylation reactions on T148C, stp192C and T135C, all of which yielded mono-PEGylated protein with 5 kDa maleimide-PEG and/or 5 kDa vinylsulfone-PEG.

EXAMPLE 14

Bioactivity of the PEG-T3C and PEG-S144C hGH Proteins

The biological activity of the PEG-T3C and PEG-S144C proteins were measured in the cell proliferation assay (Example 1). The PEG-T3C protein showed a similar dose-response curve as pituitary hGH and non-PEGylated T3C protein and reached the same level of maximal stimulation. The mean $EC_{50}$ value for PEG-T3C was 1.6 ng/ml (0.07 nM) (values of 1.3, 1.5, 1.7, 1.8 ng/ml in four experiments). Bioactivity of the PEG-T3C protein is at least 100-fold greater than that of rhGH that has been PEGylated using non-specific NHS-PEG reagents ($EC_{50}$ of 440 ng/ml (20 nM) as described in Clark et al., (1996).

The mean $EC_{50}$ value for PEG-S144C was 43 ng/ml (2 nM) (40 and 45 ng/ml in two experiments). Bioactivity of the PEG-S144C protein is approximately 10-fold greater than that of rhGH that has been PEGylated using non-specific NHS-PEG reagents ($EC_{50}$ of 440 ng/ml (20 nM); Clark et al., 1996).

EXAMPLE 15

Construction of Disulfide-Linked Trimers and Disulfide-Linked Higher Order Multimers of hGH Additional hGH variants having more than one "free" cysteine could be constructed and used to create higher order disulfide-linked multimers of hGH. These multimers could include trimers, tetramers, pentamers, hexamers, septamers, octamers, and any higher order multimers. For example, an hGH variant having two "free" cysteine residues could be constructed by using recombinant DNA technology to recombine in vitro DNA plasmid vectors carrying individual "free" cysteine mutations. Alternatively, mutagenesis of an hGH cysteine variant could be employed to add an additional "free" cysteine mutation. Further iterations of either of these two procedures could be used to construct hGH variants having three or more "free" cysteines.

An hGH variant having two free cysteine residues could be used to generate hGH trimers and higher order multimers as follows. Such a variant would be expressed in *E. coli* and recovered as a monomer in the supernatant of an osmotic shock lysate as disclosed in Examples 5-9 herein. Subsequent processing steps could then be employed to induce di-sulfide bond formation, e.g. Q Sepharose chromatography as described in Examples 6-9 herein. Under such conditions some hGH variants having one free cysteine, such as T3C and stp192C, are converted virtually quantitatively to disulfide-linked dimers. Under the same or similar conditions intermolecular disulfide formation by an hGH variant having two free cysteines, e.g. a double mutant that combined T3C and stp192C, would result in a polymerization of hGH molecules and the chain length of such polymers would in principle be unlimited. The chain length could be limited and to some extent controlled by addition to the polymerization reaction of hGH molecules having only one free cysteine such as the T3C variant and/or the stp192C variant. Disulfide bond formation between the growing polymer and a molecule having only one free cysteine will "cap" or prevent further extension of one of the two polymerization sites in the nascent polymer. A subsequent reaction of a second hGH molecule that has only one free cysteine with the other polymerization site of that nascent polymer terminates polymerization and fixes the length of that polymeric molecule. The average polymer length could be controlled by the stoichiometry of the reactants, i.e. the ratio of hGH molecules with two free cysteines to hGH molecules with one free cysteine. Average shorter polymers would be favored by lower ratios and average longer polymers would be favored by higher ratios. More complex "branched" polymers could be constructed from reactions involving hGH variants with 3 or more free cysteines with hGH variants having only one free cysteine.

Discrete size classes of certain polymers could subsequently be purified by chromatographic methods such as size exclusion chromatography, ion exchange chromatography, hydrophobic interaction chromatography, and the like. Similar procedures to those described for GH could be used to create disulfide-linked dimers and higher order multimers of EPO and alpha interferon.

EXAMPLE 16

Cloning, Expression and Purification of Baculovirus (BV)-Expressed Recombinant Human Erythropoietin (rEPO)

A. Cloning a cDNA Encoding EPO.

A cDNA encoding human EPO was cloned by PCR using forward primer BB45 (5>CCCGGAT CCATGGGGGTG-CACGAATGTCCTG>3) (SEQ.ID.NO. 25) and reverse primer BB47 (5>CCCGA ATTCTATGCCCAGGTGGACA-CACCTG>3) (SEQ.ID.NO. 26). BB45 anneals to the DNA sequence encoding the initiator methionine and amino terminal portion of the EPO signal sequence and contains a Bam HI site for cloning purposes (Jacobs et al., 1985; Lin et al., 1985). BB47 anneals to the 3' untranslated region of the EPO mRNA immediately downstream of the translational stop signal and contains an Eco RI restriction site for cloning purposes. Total RNA isolated from the human liver cell line Hep3B was used in first strand synthesis of single-stranded cDNA for PCR.

For preparation of total cellular RNA, Hep3B cells (American Type Culture Collection) were grown in Delbecco's Modified Eagle's media (DMEM) supplemented with 10% fetal bovine serum (FBS). EPO expression was induced by treating the cells for 18 h with 130 µM Deferoxamine or 100 µM cobalt chloride. Both compounds have been shown to induce EPO mRNA and protein expression in Hep 3B cells (Wang and Semenza, 1993). RNA was isolated from the cells using an RNeasy Mini kit (Qiagen, Inc.), following the manufacturer's directions. Approximately 320 µg of total RNA was isolated from $1.4 \times 10^7$ cells treated with cobalt chloride and 270 µg of total RNA isolated from $1.4 \times 10^7$ cells treated with Deferoxamine. First strand synthesis of single-stranded cDNA was accomplished using a 1st Strand cDNA Synthesis Kit for RT-PCR (AMV) from Boehringer Mannheim Corp and random hexamers were used as the primer. Subsequent PCR reactions using the products of the first strand syntheses as templates were carried out with primers BB45 and BB47. The expected ~600 bp PCR product was observed when reaction products were run out on an agarose gel. Both RNA preparations yielded an EPO PCR product. The PCR product was digested with Bam HI and Eco RI and cloned into vector pUC19 that had been cut with Bam HI and Eco RI and treated with alkaline phosphatase. DNA sequencing identified a clone containing the correct coding sequence for the EPO gene. This plasmid was designated pBBT131 and used in the construction of EPO variants by site directed mutagenesis as described in Example 17.

B. Expression of BV rEPO in Insect Cells

For expression in insect cells the EPO cDNA in pBBT131 was modified at both the 5' and 3' ends. At the 5' end, the sequence CAAA was added immediately upstream of the initiator ATG to enhance translation. This sequence comprises a proposed consensus translational initiation sequence for baculovirus (Ayres et al., 1994; Ranjan and Hasnain, 1995). At the 3' end, DNA encoding the 8 amino acid FLAG epitope sequence (asp-tyr-lys-asp-asp-asp-asp-lys) (SEQ.ID.NO. 27) was added to provide a purification system. The FLAG epitope was fused to the EPO gene via a flexible linker: ser-gly-gly-ser-gly-gly-ser (SEQ.ID.NO. 28). These modifications were made via PCR using oligonucleotide primers that incorporated the desired additions to the EPO sequence. Oligonucleotide primer BB63 (5>CGCGGATC-CAAAATGGGGGTGCAC GAATGTCCT>3) (SEQ.ID.NO. 29) was used to modify the 5' end of the gene. BB63 adds the CAAA sequence upstream of the ATG, anneals to the DNA sequence encoding the initiator methionine and amino terminal portion of the EPO signal sequence, and contains a Bam HI site for cloning purposes. The linker and FLAG sequences were added in two sequential PCR reactions using reverse primers BB60 (5>GTCTTTG-TAGTCCGAGCCTCCGCTTCCGCCCGATCT GTCC CCTGTCCTGCA>3) (SEQ.ID.NO. 30) and BB61 (5>CGC-GAATTCTTATTTATCGTCATCGTCTTTGTAGT CCGAGCCTCC>3) (SEQ.ID.NO. 31). BB60 anneals to 3' of the EPO coding sequence and contains the fused peptide linker sequence and a portion of the FLAG sequence. BB61 overlaps a segment of the BB60 sequence annealing to the junction of the linker-FLAG sequence and adds the remainder of the FLAG sequence followed by a translational stop codon (TAA) and an Eco RI site for cloning purposes. The modified EPO cDNA was cloned as a Bam HI-Eco RI fragment into pUC19 and the DNA sequence of this construct was confirmed. The resulting plasmid was designated pBBT132 and used in the construction of EPO variants as described in Example 17. For expression in baculovirus, the "FLAG-tagged" EPO cDNA was excised from pBBT132 as ~630 bp Bam HI-Eco RI fragment, gel purified, and cloned into the baculovirus transfer vector pBlueBac4.5 (Invitrogen) which had been cut with Bam HI and Eco RI and treated with alkaline phosphatase. One clone was picked for further use and designated pBBT138.

pBBT138 DNA was used to cotransfect *Spodoptera frugiperda* derived cell line Sf 9 along with linearized (Bsu36 I digested) Bac-N-Blue™ (Invitrogen Corporation) baculovirus DNA. The Bac-N-Blue™ genome is engineered so that formation of plaque-forming viral particles requires recombination between the linear Bac-N-Blue™ DNA and the pBlueBac4.5 vector, resulting in the incorporation of the cloned EPO gene into the baculovirus genome. This obligate recombination also results in incorporation of a functional β-galactosidase gene into the baculovirus genome. The co-transfection was performed according to the Invitrogen "B α-N-Blue™ Transfection Kit" protocols using $2 \times 10^6$ Sf 9 cells to generate a ~1 ml supernatant. Dilutions of this supernatant were assayed on Sf 9 cells at 27° C. for blue-plaque formation. Ten blue plaques were picked and subcultured. Each plaque was used to inoculate $2.5 \times 10^6$ Sf 9 cells in a T25 flask containing 5 ml of Grace's Insect Media supplemented with 10% FBS. After 5 days the supernatants from these infected cells (the "P1" stocks) were collected and assayed by Western Blot for EPO expression. The ten resultant supernatants were prepared in SDS sample buffer with the addition of 1% β mercaptoethanol (BME) and electrophoresed on precast 14% Tris-glycine polyacrylamide gels (Novex). Uninfected SF9 cell supernatant was included as a negative control. Following electrophoresis, the proteins were transferred onto 0.45 μm nitrocellulose (Novex). The nitrocellulose membrane was blocked in Tris Buffered Saline (TBS) with 0.05% Tween 20 and 4% powered milk (blocking buffer). Anti-FLAG M2 mouse $IgG_1$ monoclonal antibody (Eastman KODAK) was used at 1:1500 or 1:2500 dilution in blocking buffer and the blot routinely incubated overnight at 4° C. Alkaline phosphatase conjugated Sheep Anti-Mouse $IgG_1$ (The Binding Site Limited) was diluted 1:1000 in blocking buffer and the blot incubated for 1 hour at room temperature. The Western blot was developed using NBT\BCIP color development substrate (Promega). Nine of the ten isolates were positive for EPO expression. The molecular weight of the BV rEPO protein was approximately 30 kDa under reducing conditions and consisted on one major and one to two minor bands in this molecular weight range, which is consistent with a variably glycosylated protein.

Two of the positive supernatants were tested in the in vitro EPO bioassay described in Example 16.D below. Both supernatants stimulated proliferation of the EPO-dependent cell line in a dose-dependent manner, indicating that they contained active EPO. Control supernatants of mock infected Sf 9 cells and the one baculovirus supernatant that was negative for EPO expression by Western blot showed no detectable activity in the EPO bioassay.

In order to produce and purify larger amounts of wild type BV rEPO, one positive recombinant baculovirus, termed bvBBT138A, was chosen for further amplification. A 500 ml high titer viral stock was prepared by subculturing the P1 stock of isolate 138A at 27° C. in a 500 ml spinner flask culture of Sf 9 cells in Grace's Insect Media supplemented with 10% FBS. Grace's Insect Media contains approximately 100 μM L-cystine. The supernatant from this culture was harvested after 7 days and found to have a titer of ~$10^8$ plaque-forming-units/ml. An aliquot of this lysate, termed the "P2" stock, was subsequently used to infect a 500 ml culture for larger scale production of wild type BV rEPO. A 500 ml culture of Sf 9 cells in Grace's Insect Media supplemented with 10% FBS was grown in a spinner flask to a titer of $1.0 \times 10^6$/ml and then infected with bvBBT138A at a multiplicity of infection of 1. After 3 days the supernatant from this culture was harvested and wild type BV rEPO-138A protein purified as described in Example 16.C.

C. Affinity Purification of Wild Type Baculovirus-Produced rEPO

The cell supernatant was clarified by centrifugation and 0.2 μM filtration. Expression of wild type BV rEPO was confirmed by Western blot analysis. Wild type BV rEPO was purified in a single step procedure using Anti-FLAG M2 Affinity Gel (Eastman KODAK). Briefly, 5 ml of the M2 affinity gel was washed with 5 column volumes of 50 mM Tris pH 7.4, 150 mM NaCl (TBS), 5 column volumes of 0.1M glycine pH 3.5, then equilibrated in TBS. The clarified baculoviral cell supernatant was adjusted to 150 mM NaCl and the equilibrated resin was added. Batch loading was allowed to continue at 4° C. overnight on a roller bottle apparatus. After overnight incubation, the resin was recovered using a Pharmacia XK 16/20 FPLC column and washed with TBS until the A280 reached baseline. The bound protein was eluted with 0.1M glycine pH 3.5 and fractions were collected and neutralized with 1.0M Tris pH 9.0. Column fractions were prepared in SDS-PAGE sample buffer with the addition of 1% BME when desirable and electrophoresed on precast 14% Tris-glycine polyacrylamide gels. Fractions from the M2 affinity column that contained most of the BV rEPO were pooled and concentrated on a Centricon 10 spin concentrator (Amicon). The final yield of wild type BV rEPO, as determined using a Bradford protein assay kit (BIO-RAD Laboratories, Inc.) and bovine serum albumin (BSA) as the standard, was approximately 360 μg. The protein was estimated to be greater than 90% pure by Coomassie Blue staining of SDS gels.

D. In Vitro Bioactivity of Wild Type Baculovirus rEPO

A cell proliferation assay using the human UT7/epo cell line (Komatsu et al., 1991) was developed to measure bioactivity of wild type BV rEPO. The human UT7/epo cell line was obtained from Dr. F. Bunn of Harvard Medical School. This cell line is dependent upon EPO for cell proliferation and survival (Boissel et al., 1993). The cells were maintained in Iscove's Modified Delbecco's Media (IMDM) supplemented with 10% FBS, 50 units/ml penicillin, 50 μg/ml streptomycin and 1 unit/ml rEPO (CHO (Chinese Hamster Ovary) cell-expressed; purchased from R&D Systems, Inc.). For bioassays, the cells were washed three times with IMDM media and resuspended at a concentration of $1 \times 10^5$ cells/ml in IMDM media containing 10% FBS, 50 units/ml penicillin and 50 μg/ml streptomycin. Fifty μl ($5 \times 10^3$ cells) of the cell suspension were aliquotted per test well of a flat bottom 96 well tissue culture plate. Serial 3-fold dilutions of the protein samples to be tested were prepared in phenol red-free IMDM media containing 10% FBS, 50 units/ml penicillin and 50 μg/ml streptomycin. Fifty μl of the diluted protein samples were added to the test wells and the plates incubated at 37° C. in a humidified 5% $CO_2$ tissue culture incubator. Protein samples were assayed in triplicate wells. After 60-72 h, 20 μl of CellTiter 96 AQueous One Solution Reagent (Promega Corporation) was added to each well and the plates incubated at 37° C. in the tissue culture incubator for 1-4 h. Absorbance of the wells was read at 490 nm using a microplate reader. Control wells contained media but no cells. Mean absorbance values for the triplicate control wells were subtracted from mean values obtained for each set of triplicate test wells.

Serial dilutions of CHO cell-expressed rEPO or wild type BV rEPO were analyzed in parallel.

The UT7/epo cell line shows a strong proliferative response to rEPO, as evidenced by a dose-dependent increase in cell number and absorbance values. Absorbance is proportional to cell number up to values of 2.0 (Promega Corporation product specifications). In the absence of rEPO, the majority of UT7/epo cells die, giving absorbance values less than 0.1. Commercial CHO cell-expressed rEPO and wild type BV rEPO prepared by us reached the same maximal level of stimulation, within the error of the assay, and had similar mean $EC_{50}$s in the bioassay of approximately 0.4-0.5 ng/ml (Table 2). $EC_{50}$ values for these proteins ranged from 0.21 to 0.65 ng/ml in assays performed on different days (Table 2); therefore comparisons between protein samples were made on samples analyzed on the same day. These $EC_{50}$ values agree with values reported in the R&D Systems specifications for CHO rEPO (0.05-0.1 unit/ml or approximately 0.4-0.8 ng/ml).

EXAMPLE 17

Construction, Expression, Purification and Bioactivity of EPO Cysteine Muteins

A. Construction of EPO Cysteine Muteins.

Eight mutant EPO genes were constructed using site-directed PCR-based mutagenesis procedures similar to those used to construct the Growth Hormone muteins described in Example 4 (Innis et al, 1990; Horton et al., 1993). We constructed four muteins at or near the two N-linked glycosylation sites in the A-B loop (N24C, T26C, N38C and T40C), two muteins at or near the N-linked glycosylation site in the B-C loop (N83C and S85C), one mutein at the O-linked glycosylation site in the C-D loop (S126C) and one mutein (*167C), that adds a cysteine between the natural carboxy-terminal R166 residue and the 15 amino acid carboxyterminal extension consisting of the peptide linker and FLAG sequences. The template for the mutagenic PCR reactions was plasmid pBBT131, in which the unmodified EPO gene is cloned as an Bam HI-Eco RI fragment into pUC19. PCR products were digested with appropriate restriction endonucleases, gel-purified and ligated with pBBT132 vector DNA that had been cut with appropriate restriction enzymes, alkaline phosphatase treated, and gel-purified. As detailed above, pBBT132 is a pUC19 derivative carrying the cloned modified (FLAG tagged) EPO gene. Transformants from these ligations were grown up and plasmid DNAs isolated and sequenced. The sequence of the entire cloned mutagenized PCR fragment was determined to verify the presence of the mutation of interest, and the absence of any additional mutations that potentially could be introduced by the PCR reaction or by the synthetic oligonucleotide primers.

The cysteine substitution mutation N24C was constructed as follows. The mutagenic forward oligonucleotide BB64 (5>GAGGCCAAGGAGGCCGAGTGTATCAC-GACGGGCTGTGCT>3) (SEQ.ID.NO. 32) was designed to change the codon AAT for asparagine at position 24 to a TGT encoding cysteine and to span the nearby Sty I site. This oligo was used in PCR with the reverse, non-mutagenic, primer BB47 (5>CCCGAATTCTGGTGGATATGCCCAGGTG-GAC>3) (SEQ.ID.NO. 33) which anneals to DNA sequences 3' to the coding sequence of EPO. A 50 μl PCR reaction was performed in 1× Promega PCR buffer containing 1.5 mM $MgCl_2$, each primer at 0.2 μM, each of dATP, dGTP, dTTP and dCTP at 200 μM, 1 ng of template plasmid pBBT131 (described in Example 16), 1.5 units of Taq Polymerase (Promega), and 0.25 units of Pfu Polymerase (Stratagene). Reactions were performed in a Robocycler Gradient 96 thermal cycler (Stratagene). The reaction program entailed: 96° C. for 3 minutes, 25 cycles of [95° C. for 1 minute, 60° C. for 1.25 minutes, 72° C. for 1 minute] followed by a hold at 6° C. A 5 μl aliquot of the PCR reaction was analyzed by agarose gel electrophoresis and found to produce a single fragment of the expected size ~470 bp. The remainder of the reaction was "cleaned up" using the QIAquick PCR Purification (Qiagen) according to the vendor protocol, digested with Sty I and Bsr GI (New England BioLabs) according to the vendor protocols, ethanol-precipitated, resuspended in 20 μl of 10 mM Tris-HCl pH 8.5 and run out on a 2% agarose gel. The ~400 bp Sty I-Bsr GI fragment of interest was gel purified using a QIAEX II Gel Extraction Kit (Qiagen) according to the vendor protocol. This fragment was ligated with pBBT132 (described in Example 16) that had been cut with Sty I and Bsr GI, treated with calf intestinal alkaline phosphatase (New England BioLabs) and gel purified. The ligation reaction was used to transform E. coli and plasmids from resulting transformants were sequenced to identify a clone containing the N24C mutation and having the correct sequence throughout the remainder of the ~400 bp Sty I-Bsr GI segment.

The substitution mutation T26C was constructed and its sequence verified using the protocol described above for N24C except that mutagenic forward oligo BB65 (5>GAG-GCCAAGGA GGCCGAGAAATCTGTACGGGCTGT-GCT>3) (SEQ.ID.NO.34) was used instead of BB64.

The substitution mutation N38C was constructed using the technique of "mutagenesis by overlap extension" as described in Example 4. With the exception of the use of different oligonucleotide primers, the initial, or "primary" PCR reactions for the N38C construction were performed identically to those described in the construction of N24C above. The primer pairs used were (BB66+BB47) and (BB67+BB45). BB47 is described above. The forward, non-mutagenic, primer BB45 (5>CCCGGATCCATGGGGGTG-CACGAATGTCCTG>3) (SEQ.ID.NO. 35) anneals to the EPO sequence encoding the first seven amino acids of EPO. BB66 and BB67 are complementary mutagenic oligonucleotides that change the AAT codon for N38 to a TGT codon for cysteine. The sequence of BB66 is (5>AGCTTGAATGAGT-GTATCACTGTCCCAGACACC>3) (SEQ.ID.NO. 36) and the sequence of BB67 is (5>GGTGTCTGGGACAGTGATA-CACTCATT CAAGCT>3) (SEQ.ID.NO. 37). The (BB66× BB47) and (BB67×BB45) PCR reactions gave products of the expected sizes: ~420 bp for (BB66×BB47) and ~220 bp for (BB67×BB45). The PCR products were ethanol-precipitated, gel-purified and recovered in 20 μl 10 mM Tris-HCl as detailed above. These two mutagenized fragments were then "spliced" together in the subsequent, or "secondary" PCR reaction. In this reaction 1 μl of each of the gel-purified PCR products of the primary reactions were used as template and BB45 and BB47 were used as primers. Otherwise, the reaction conditions identical to those used in the primary reactions. An aliquot of the secondary PCR was analyzed by agarose gel electrophoresis and the expected band of ~630 bp was observed. The bulk of the secondary PCR reaction was "cleaned up" using the QIAquick PCR Purification (Qiagen) according to the vendor protocol, digested with Sty I and Bsr GI (New England BioLabs) according to the vendor protocols, ethanol-precipitated, resuspended in 20 μl of 10 mM Tris-HCl pH 8.5 and run out on a 2% agarose gel. The ~400 bp Sty 1-Bsr GI fragment of interest was gel purified using a QIAEX II Gel Extraction Kit (Qiagen) according to the vendor protocol. This fragment was ligated with pBBT132 (described in Example 16) that had been cut with Sty I and Bsr GI, treated with calf intestinal alkaline phosphatase (New England BioLabs) and gel purified. The ligation reaction was used to transform E. coli and plasmids from resulting transformants were sequenced to identify a clone containing the N38C mutation and having the correct sequence throughout the ~400 bp Sty 1-Bsr GI segment.

The substitution mutation T40C was constructed and sequence verified using the procedures described above for N38C except that complementary mutagenic primers BB68 (5>AGCTTG AATGAGAATATCTG TGTCCCAGA-CACC>3) (SEQ.ID.NO. 38) and BB69 (5>GGTGTCTGG-GACACAGATATTCTC ATTCAAGCT>3) (SEQ.ID.NO. 39), which change the ACT codon for T40 to a TGT codon for cysteine, replaced BB66 and BB67 respectively in the primary PCR reactions.

The substitution mutation N83C was constructed and sequence verified using the procedures described above for N38C except that complementary mutagenic primers BB70 (5>GCCCTGT TGGTCTGCTCTTCCCAGCCGTGG-GAGCCCCTG>3) (SEQ.ID.NO. 40) and BB71 (5>CAGGGGCTCCCACGGCTGG GAAGAGCAGACCA ACAGGGC>3) (SEQ.ID.NO. 41), which change the AAC codon for N83 to a TGC codon for cysteine, replaced BB66 and BB67, respectively, in the primary PCR reactions. The sizes of the products of the primary PCR reactions were also different. The (BB70×BB47) reaction gave, as predicted, a product of ~300 bp and the (BB71×BB45) reaction gave, as predicted, a product of ~360 bp.

The substitution mutation S85C was constructed and sequence verified using the procedures described above for N38C except that complementary mutagenic primers BB72 (5>GCC CTGTTGGTCAAC TCTTGCCAGCCGTGG-GAGCCCCTG>3) (SEQ.ID.NO. 42) and BB73 (5>CAGGGGCTCCCACG GCTGGCAAGAGTTGAC-CAACAGGGC>3) (SEQ.ID.NO. 43), which change the TCC codon for S85 to a TGC codon for cysteine, replaced BB66 and BB67 respectively in the primary PCR reactions. The sizes of the products of the primary PCR reactions were also different. The (BB72×BB47) reaction gave, as predicted, a product of ~300 bp and the (BB73×BB45) reaction gave, as predicted, a product of ~360 bp.

The substitution mutation S126C was constructed using the procedures described above for N38C except that complementary mutagenic primers BB74 (5>CCAGATGCGGCCT-GTGCTGC TCCACTC>3) (SEQ.ID.NO. 44) and BB75 (5>GAGTGGAGCAGCACAGGCCGCATCTGG>3) (SEQ.ID.NO. 45), which change the TCA codon for 5126 to a TGT codon for cysteine, replaced BB66 and BB67 respectively in the primary PCR reactions. The sizes of the products of the primary PCR reactions were also different. The (BB74×BB47) reaction gave, as predicted, a product of ~175 bp and the (BB75×BB45) reaction gave, as predicted, a product of ~480 bp.

A mutation was also constructed that added a cysteine following the carboxyterminal amino acid of the EPO coding sequence. This mutant, termed *167C was constructed as follows. A PCR reaction was carried out under the conditions described above for the construction of the N24C mutant, but employing oligonucleotides BB45 (see above) and reverse mutagenic oligonucleotide BB77 (5>TTTGTAGTCCGAG CCTCCGCTTCCGCCCGAACA TCTGTCCCCTGTCCT-GCA>3) (SEQ.ID.NO. 46) and using 2.5 units of Taq Polymerase and 0.5 units of Pfu Polymerase. BB77 anneals to the terminal 21 residues of EPO coding sequence and adds a TGT codon for cysteine following the AGA codon for R166, which is the terminal amino acid in the EPO coding sequence. BB77 also adds sequences encoding the seven amino acid linker -ser-gly-gly-ser-gly-gly-ser- (SEQ.ID.NO. 27), and a portion of the FLAG epitope sequence. The ~630 bp product of this PCR reaction was gel purified and used as template in a subsequent PCR reaction employing the same reaction conditions but using primers BB47 and BB61 (5>CGCGAAT-TCTTATTTATCGTCATCGTCTTTGTAGTCCGAGCC TCC>3) (SEQ.ID.NO.30), which adds the remainder of the FLAG epitope sequence followed by a TAA stop codon and an Eco RI cloning site. The ~675 bp product of this PCR reaction was "cleaned up" using the QIAquick PCR Purification (Qiagen) according to the vendor protocol, digested with Sty I and Eco RI (New England BioLabs) according to the vendor protocols, ethanol-precipitated, resuspended in 20 µl of 10 mM Tris-HCl pH 8.5 and run out on a 2% agarose gel. The ~86 bp Eco RI-Bsr GI fragment of interest was gel purified using a QIAEX II Gel Extraction Kit (Qiagen) according to the vendor protocol. This fragment was ligated with pBBT132 (described in Example 16) that had been cut with Eco RI and Bsr GI, treated with calf intestinal alkaline phosphatase (New England BioLabs) and gel purified. The ligation reaction was used to transform E. coli and plasmids from resulting transformants were sequenced to identify a clone containing the *167C mutation and having the correct sequence throughout the ~86 bp Eco RI-Bsr GI segment.

For expression in baculovirus, the EPO genes encoding the 8 muteins were excised from the pUC19-based pBBT132 derivatives as Bam H1-Eco RI fragments of ~630 bp and subcloned into the pBlueBac4.5 baculovirus transfer vector used to express wild type EPO.

Using procedures similar to those described here, one can construct other cysteine muteins of EPO. The cysteine muteins can be substitution mutations that substitute cysteine for a natural amino residue in the EPO coding sequence, insertion mutations that insert a cysteine residue between two naturally occurring amino acids in the EPO coding sequence, or addition mutations that add a cysteine residue preceding the first amino acid, A1, of the EPO coding sequence or add a cysteine residue following the terminal amino acid residue, R166, of the EPO coding sequence. The cysteine residues can be substituted for any amino acid, or inserted between any two amino acids, anywhere in the EPO coding sequence. Preferred sites for substituting or inserting cysteine residues in EPO are in the region preceding Helix A, the A-B loop, the B-C loop, the C-D loop and the region distal to Helix D. Other preferred sites are the first or last three amino acids of the A, B, C and D Helices. Preferred residues in these regions for creating cysteine substitutions are A1, P2, P3, R4, L5, D8, S9, I25, T27, G28, A30, E31, H32, S34, N36, I39, D43, T44, K45, N47, Y49, A50, K52, R53, M54, E55, G57, Q58, G77, Q78, A79, S84, Q86, W88, E89, T107, R110, A111, G113, A114, Q115, K116, E117, A118, 5120, P121, P122, D123, A124, A125, A127, A128, R131, T132, K154, Y156, T157, G158, E159, A160, T163, G164, D165, R166. Cysteine residues also can be inserted immediately preceding or following these amino acids. Another preferred site for adding a cysteine residue would be preceding A1, which we refer to as *-1C.

One also can construct EPO muteins containing a free cysteine by substituting another amino acid for one of the naturally-occurring cysteine residues in EPO. The naturally-occurring cysteine residue that normally forms a disulfide bond with the substituted cysteine residue is now free. The non-essential cysteine residue can be replaced with any of the other 19 amino acids, but preferably with a serine or alanine residue. A free cysteine residue also can be introduced into EPO by chemical modification of a naturally occurring amino acid using procedures such as those described by Sytkowski et al. (1998).

Using procedures similar to those described in Examples 16-19, one can express the proteins in eukaryotic cells (e.g., insect cells or mammalian cells), purify the proteins, PEGylate the proteins and measure their bioactivities in an in vitro bioassay. The EPO muteins also can be expressed in prokaryotic cells such as *E. coli* using procedures similar to those described in Examples 1-15, or related procedures well known to those skilled in the art.

B. Insect Cell Expression of EPO-Cys Muteins.

For expression experiments, the eight plasmids encoding mutant EPO genes were used to cotransfect Sf 9 cells along with linearized Bac-N-Blue™ DNA using the procedures described above for plasmid pBBT138, which encodes wild type EPO. The transfection supernatants were assayed on Sf 9 cells for blue-plaque formation. For each mutant, ten blue plaques were picked and subcultured as described in Example 16. Five of the ten resulting supernatants were screened by SDS-PAGE and Western blot to detect expression of the EPO muteins. Western blot analysis was carried out using the procedure described in Example 16 for wild type EPO. Western results showed that at least 3 of the 5 supernatants screened from each clone contained FLAG-tagged EPO protein. Western blot results also revealed that plasmids encoding muteins that should prevent glycosylation at one of the N-linked glycosylation sites (N24C, T26C, N38C, T40C, N83C and S85C) yielded proteins with molecular weights approximately 2,200-2,800 daltons smaller than wild type BV rEPO. In contrast, the S126 mutein at the O-linked glycosylation site, and *167C(C-terminal cysteine addition) yielded EPO proteins that co-migrated with wild type BV rEPO. These results are consistent with the observation that insect cells typically perform N-linked glycosylation and that sugar groups attached to O-linked glycosylation sites are generally small and cause minimal increases in a protein's molecular weight. Insect cells are reported to perform O-linked glycosylation (Davies, 1995).

In order to purify larger amounts of the EPO muteins one positive recombinant baculovirus isolate that encoded each mutein was chosen for further amplification. A 500 ml high titer viral stock was prepared from each of the mutant P1 stocks by subculturing as described above for the wild type isolate. An aliquot of each of these P2 lysates was subsequently used to infect a 500 ml culture for larger scale production of each of the EPO muteins using the procedures described for wild type EPO in Example 16. The 500 ml supernatants from baculovirus infected cells were subsequently sterile filtered and stored at 4° C. rEPO-Cys muteins were purified using an anti-FLAG M2 Affinity Gel column (Eastman Kodak), using a different batch of resin for each mutein to ensure no cross-contamination. 5 ml of resin was first washed with 50 mM Tris, 150 mM NaCl, pH 7.4 (TBS), followed by 0.1 M Glycine pH 3.0, and finally re-equilibrated in TBS. Sodium chloride was added to the baculovirus culture filtrate to a final concentration of 0.15 M before the affinity resin was added. The resin was batch-loaded on a roller bottle apparatus overnight at 4° C. The next morning the resin was captured using an XK16 Pharmacia column and washed with TBS until the A280 reached baseline. The rEPO-Cys muteins were eluted with 0.1 M Glycine, pH 3.0. Fractions (1.5 ml) were collected into tubes containing 20 µL of 1 M Tris Base, pH 9.0 to neutralize the solution. Based on the chromatograms and SDS-PAGE analyses, fractions containing predominantly pure rEPO-Cys proteins were pooled and frozen. Protein recoveries from the 500 ml supernatant cultures varied from 75 to 800 µg, depending upon the mutein (Table 2).

The purified rEPO-Cys muteins migrated with apparent molecular weights of 27-30 kDa under non-reducing conditions, consistent with the proteins being monomeric. The apparent molecular weights of the rEPO-Cys muteins fell into two classes, presumably due to glycosylation differences. rEPO-Cys proteins containing mutations at the O-glycosylation site (S126C) and at the C-terminus (*167C) migrated at a position similar to wild type BV rEPO. Proteins containing mutations that should prevent glycosylation of one of the N-linked glycosylation sites (N24C, T26C, N38C, T40C, N83C and S85C proteins) migrated with apparent molecular weights of 27-28 kDa, slightly smaller than wild type BV rEPO. Surprisingly, the S85C protein migrated as a doublet under both reducing and non-reducing conditions; the major band of the doublet was the expected size for a protein lacking glycosylation at one of the N-linked glycosylation sites, while the minor band was the size expected for fully glycosylated wild-type BV rEPO. All of the original recombinant Baculovirus plaques isolated for the S85C mutein yielded rEPO proteins that migrated as doublets, suggesting that the doublet is due to partial glycosylation at N83 (or another amino acid) rather than contamination of S85C with wild type BV EPO or S126C or *167C proteins. Several of the muteins, e.g., S126C, *167C, had small amounts of a second protein that migrated with an apparent molecular weight of 45-55 kDa, depending upon the mutein. This is the molecular weight expected for disulfide-linked rEPO dimers. These bands reacted with the anti-FLAG antibody in Western blots and were absent when the SDS gels were run under reducing conditions. These data indicate that the 45-55 kDa bands represent disulfide-linked rEPO-Cys dimers.

C. Bioactivities of EPO Cysteine Muteins.

Biological activities of the purified rEPO-Cys muteins were measured in the UT7/epo cell proliferation assay described in Example 16. Protein concentrations were determined using a Bradford assay. Because of the large number of samples the muteins were divided into two groups for analysis: muteins T26C, T40C, N83C and S126C comprised one group and muteins N24C, N38C, S85C and *167C comprised the second group. Muteins within a group were analyzed on the same day. Wild type BV rEPO and CHO rEPO were analyzed in parallel on the same days to control for interday variability in the assays. All of the muteins stimulated proliferation of UT7/epo cells and had $EC_{50}$s that were within three-fold of the wild type rEPO control proteins. Mean $EC_{50}$s for the N24C, T26C, N83C, S85C, S126 and *167C muteins were similar to the mean $EC_{50}$s for wild type BV rEPO and CHO rEPO, averaging 0.3-0.8 ng/ml (Table 2). Mean $EC_{50}$s for the N38C and T40C proteins were approximately 1 ng/ml (Table 2).

Bill et al., (1995) reported expression of the EPO cysteine muteins, N24C, N38C and N83C, in *E. coli*. In contrast to our results, they reported that bioactivities of these cysteine muteins were significantly reduced relative to wild type EPO. Bioactivity of the N38C mutein was reduced to less than 20% of wild type EPO bioactivity and bioactivities of the N24C and N83C muteins were reduced to less than 5% of wild type EPO bioactivity. $EC_{50}$s were not reported. Bill et al. (1995) postulated that the reduced activities of the cysteine muteins were due to improper folding due to incorrect formation of disulfide bridges resulting from the extra cysteine residues introduced into the proteins. They did not employ cystine or other cysteine-blocking agents in the solutions used to purify the cysteine muteins.

Based upon the results of Bill et al. (1995), it was surprising that our purified N24C, N38C and N83C muteins had biological activities equal to, or within 3-fold of, wild type EPO. The data indicate that our methods for expression and purification of the EPO cysteine muteins results in proteins with superior in vitro biological activities compared to the methods employed by Bill et al. (1995).

TABLE 2

Properties of Human EPO Cysteine Muteins

| Expression Plasmid | EPO Protein | Protein Recovery μg/500 ml | Mutation Location | Mean EC$_{50}$ (ng/ml) | EC$_{50}$ Range[1] |
|---|---|---|---|---|---|
| — | rEPO (CHO) | — | — | 0.50 | 0.29-0.65 (N = 6) |
| pBBT138 | rEPO (BV) | 345 | — | 0.37 | 0.21-0.51 (N = 6) |
| pBBT150 | N24C | 75 | A-B loop | 0.76 | 0.58, 0.85, 0.85 |
| pBBT151 | T26C | 805 | A-B loop | 0.27 | 0.21, 0.22, 0.39 |
| pBBT152 | N38C | 85 | A-B loop | 1.05 | 0.65, 1.20, 1.30 |
| pBBT161 | T40C | 102 | A-B loop | 0.95 | 0.60, 0.75, 1.50 |
| pBBT162 | N83C | 96 | B-C loop | 0.50 | 0.42, 0.49, 0.60 |
| pBBT153 | S85C | 135 | B-C loop | 0.72 | 0.50, 0.80, 0.85 |
| pBBT154 | S126C | 220 | C-D loop | 0.31 | 0.25, 0.25, 0.42 |
| pBBT155 | *167C | 129 | C-terminus | 0.61 | 0.51, 0.65, 0.68 |

[1]Data from individual experiments. A range is shown when N > 3.

EXAMPLE 18

PEGylation of EPO Cysteine Muteins

A. Small-Scale PEGylation of EPO Cysteine Muteins

Several cysteine muteins and wild type EPO were tested for their ability to be PEGylated with a 5 kDa cysteine-reactive PEG following treatment with the reducing agent TCEP (Tris(2-carboxyethyl)phosphine-HCl). A titration study was performed with the T26C mutein to identity appropriate TCEP and PEG reagent concentrations for PEGylation, while avoiding over-reduction of the protein. We monitored partial reduction of the protein by SDS-PAGE, using wild type BV rEPO as a control. Increasing concentrations of TCEP (0.5 M to 6.0 M excess) in the presence of a 10-40-fold molar excess of either vinylsulfone or maleimide 5 kDa PEG (Fluka) were tested. The reactions were analyzed by non-reducing SDS-PAGE. Wild type BV rEPO was treated in parallel as a control to identify partial reduction conditions that yielded significant amounts of monoPEGylated EPO-Cys muteins (a single PEG molecule attached to the EPO-Cys mutein), but no PEGylation of wild type BV rEPO. A 5-fold molar excess of TCEP and a 30-fold molar excess of 5 kDa vinylsulfone-PEG yielded significant amounts of monoPEGylated T26C protein without PEGylation of wild type BV rEPO.

Based on our findings with the T26C mutein, the following conditions were used to PEGylate several other cysteine muteins. Aliquots (1-2 μg) of purified BV rEPO and EPO-Cys muteins were incubated for 1 hr with a 5× molar excess of TCEP and a 30× molar excess of 5 kDa vinylsulfone PEG at pH 8.0 at room temperature. The reactions were stopped by dilution into SDS sample buffer (without reducing reagent) and analyzed by SDS-PAGE. Four cysteine muteins (N24C, T26C, S126C and *167C) were readily monoPEGylated under these conditions, as evidenced by the appearance of a new protein band migrating at approximately 35 kDa. The 35 kDa species is the size expected for mono-PEGylated EPO; no diPEGylated species, which are expected to have molecular weights of approximately 40 kDa, were detected for any of the EPO-cys muteins under these reaction conditions. Control experiments indicated that the cysteine muteins needed to be reduced with TCEP in order to be PEGylated. Wild type BV EPO did not PEGylate under identical partial reducing conditions. These data indicate that the PEG molecule is attached to the free cysteine introduced into the N24C, T26C, S126C and *167C EPO-Cys muteins.

B. Preparation of PEG-T26C and PEG-S126C for Bioactivity Measurements.

We PEGylated larger quantities of the T26C and S126C proteins so that the PEGylated proteins could be purified for bioactivity measurements. PEGylation reactions were scaled to include 75 μg of each protein and the same molar ratios of TCEP and 5 kDa-PEG used in the smaller 1 μg reactions. After 1 hour, the PEGylation mixture was diluted 10× with 20 mM Tris-HCl, pH 8.0, 20% glycerol (Buffer A) and loaded immediately onto a 1 ml Q-Sepharose column equilibrated in Buffer A. The column was washed with equilibration buffer and bound proteins eluted with a linear 10 volume increasing salt gradient from 0 to 150 mM NaCl in 20 mM Tris-HCl, pH 8.0, 20% glycerol. The presence of the PEG moiety decreased the protein's affinity for the resin, allowing the PEGylated protein to be separated from the non-PEGylated protein. Fractions containing mono-PEGylated protein were identified by SDS-PAGE, followed by Coomassie Blue staining Fractions containing PEG-T26C but no visible underivatized protein, were stored frozen at −80° C. and subsequently used in bioassays. Similar procedures were used to obtain purified PEG-S126C. A Western blot was performed to assess the purity of the PEG-T26C and PEG-S126C preparations used in bioassays. The Western blot was performed as described in Example 16. The Western blot gave strong signals at the sizes expected for PEG-T26C and PEG-S126C, but failed to detect any protein migrating at the positions expected for the unPEGylated S126C and T26C proteins. From these results, we conclude there is little (<5%) unPEGylated protein present in the purified PEGylated muteins.

C. Bioactivities of PEG-T26C and PEG-S126C Cysteine Muteins

The biological activities of the purified PEG-T26C and PEG-S126C proteins were measured in the UT7/epo cell proliferation assay described in Example 16. Protein concentrations of the PEG-EPO-Cys muteins were quantitated using a human EPO ELISA kit (R & D Systems), following the manufacturer's suggested directions. Protein concentrations of the non-PEGylated muteins and wild type BV rEPO also were quantitated by ELISA. The ELISA assay was performed on all the proteins on the same day. Serial three-fold dilutions of the protein samples were prepared and analyzed in the bioassay. Unused material from each serial dilution was stored frozen at −80° C. and later analyzed in the ELISA to determine an accurate protein concentration for the starting material. Several of the serial dilutions for each protein sample were analyzed to ensure that the protein concentration in at least one test sample fell within the linear range of the standard ELISA curve, which is 0.0025-0.2 Units/ml or approximately 0.02-1.6 ng/ml. At least two of the serial dilutions for each sample fell within this linear range.

Biological activities for the PEG-T26C and PEG-S126C muteins were similar to those of the non-modified T26C and S126C proteins and wild type BV rEPO. Mean EC$_{50}$s for the PEG-T26C and PEG-S126C muteins were similar to the mean EC$_{50}$ values determined for the non-PEGylated T26C and S126C muteins and wild type BV rEPO, ranging from 0.48-0.82 ng/ml (Table 3). Biologically active, PEGylated EPO proteins have not been described previously.

TABLE 3

Bioactivities of PEG-Cys EPO Muteins

| EPO Protein | Mean EC$_{50}$ (ng/ml) | EC$_{50}$ Range[1] (ng/ml) |
|---|---|---|
| BV EPO | 0.82 | 0.55, 0.95, 0.95 |
| T26C | 0.73 | 0.50, 0.85, 0.85 |
| PEG-T26C | 0.58 | 0.35, 0.65, 0.75 |
| S126C | 0.74 | 0.65, 0.75, 0.82 |
| PEG-S126C | 0.48 | 0.38, 0.52, 0.55 |

[1]Data from three experiments.

EXAMPLE 19

Expression and Purification of EPO Cysteine Muteins in Mammalian Cells

The EPO cysteine muteins also can be expressed in mammalian cells and purified from the conditioned media. The EPO cysteine muteins can be expressed by transient transfection of mammalian cells or by constructing stably transformed mammalian cell lines expressing the EPO cysteine muteins. For therapeutic applications in humans, it is preferable that the EPO cysteine muteins be expressed without the linker and FLAG sequences. Monkey COS cells (available from the American Type culture Collection) can be used for transient transfection experiments, using procedures well known to those of skill in the art. A number of commercial sources, e.g., GIBCO/BRL sell lipid transfection reagents and provide detailed protocols that can be used to express the EPO cysteine muteins by transient transfection. Wild type EPO is manufactured for use in humans using stably transformed Chinese hamster ovary (CHO) cells expressing the protein. Stably transfected CHO cell lines are widely used for high-level expression of recombinant proteins (Geisse et al. 1996; Trill et al. 1995). In CHO cells, high level expression of chromosomally integrated heterologous genes can be achieved by gene amplification. Typically the gene of interest is linked to a marker gene for which amplification is selectable. A variety of genes which provide selections for amplification have been described (Kaufman 1990) but murine dihydrofolate reductase (dhfr) is frequently employed. Amplification of this gene confers resistance to the folate analog methotrexate (MTX) and the level of resistance increases with dhfr gene copy number (Alt et al., 1978). Utility of MTX selection is enhanced by the availability of CHO cell lines that are deficient in dhfr (Urlaub and Chasin, 1980).

One skilled in the art can construct expression vectors for the EPO cysteine muteins that incorporate the murine dhfr gene into the commercially available pcDNA3.1 expression vector (Invitrogen), which includes the neomycin phosphotransferase (NPT) gene that confers resistance to G418. The murine dhfr expression vector pdhfr2.9 is available from the American Type Culture Collection (catalogue No. 37165). This dhfr gene is selectable in dhfr⁻ CHO cell lines and can be amplified by standard selections for MTX resistance (Crouse et al 1983). The dhfr coding sequence can be excised from pdhfr2.9 as a ~900 bp Bgl II fragment and cloned into the unique Bam HI site of the polylinker of the expression vector pREP4 (Invitrogen). This construct will position the gene downstream of the strong RSV promoter, which is known to function in CHO cells (Trill et al, 1995) and upstream of a polyadenylation site derived from SV40. This dhfr expression cassette can then be excised from pREP4 as a Sal I fragment since Sal I sites closely flank the promoter and polyA addition site. Using oligonucleotide linkers this Sal I fragment can be cloned into the unique Bgl II site of pcDNA3.1.

For expression in mammalian cells such as COS or CHO cells, the EPO cysteine mutein cDNAs can be modified by PCR-based mutagenesis. At the 5' end one can add a Kozak consensus sequence prior to the translational initiator ATG codon in order to enhance translation in mammalian cells. At the 3' end, the linker and FLAG sequences can be removed and the natural coding sequence and translation termination signal restored. These modified EPO cDNAs can then be cloned as Bam HI-Eco RI fragments into the polylinker of pcDNA3.1 for transient transfection experiments or into the polylinker of the pcDNA3.1::dhfr vector for stable expression in mammalian cells. For mammalian cell expression, the mutant EPO genes encoding the cysteine muteins would be modified at the 5' end to incorporate a Kozak consensus sequence (GCCACC) immediately preceding the translational initiator ATG codon in order to enhance translation in mammalian cells. At the 3' end the linker and FLAG sequences would be removed and the natural coding sequence restored. These modifications could be accomplished by a variety of mutagenesis techniques that are well known to those skilled in the art. PCR-based mutagenesis procedures based on those described in Examples 4 and 17 could be employed. PCR primers BB302 (5>CGCGGATCCGCCAC-CATGGGGGTGCAC GAATGTCCT>3) (SEQ.ID.NO.47) and BB303 (5>CGCGAATTCTCATCTGTCCCCTGTCCT-GCAGCC>3) (SEQ.ID.NO. 48) could be used to PCR the mutated EPO genes cloned in pUC19 or pBlueBac4.5 as templates. Forward primer BB302 anneals to the EPO gene sequence encoding the first seven amino acids of the EPO secretion signal, adds a Kozak consensus sequence, GCCACC, immediately preceding the translational initiator ATG codon, and includes a Bam HI site for cloning purposes. The reverse primer BB303 anneals to sequences encoding the carboxyterminal seven amino acids of the EPO coding sequence, adds a TGA translational stop codon following the EPO coding sequence and includes a Eco RI site for cloning purposes. The products of the individual PCR reactions using these primers and any mutant EPO gene template that has a mutation between these two primers, e.g. amino acid substitutions at amino acids 1 through 159 of the mature EPO coding sequence, will produce PCR products that can be purified, digested with Bam HI and Eco RI and cloned into a vector suitable for expression in mammalian cells such as pcDNA3.1(+) (Invitrogen). PCR primers 302 and 303 also could be used to modify EPO cysteine muteins in which a cysteine residue is added preceding the first amino acid, A1, of the mature EPO coding sequence, but distal to the EPO signal sequence. Mutations in the EPO sequence that encode the carboxyterminal seven amino acids, or the *167C mutation described in Example 17, would require the use of alternative reverse primers in place of BB303. These primers would be individually designed to include the mutated cysteine codon, at least 21 nucleotides at the 3' end of the oligo that exactly match the template target, and the Eco RI site for cloning purposes. For example the reverse primer BB304 (5>CGCGAATTCTCAACATCT GTCCCCTGTCCTG CAGCC>3) (SEQ.ID.NO. 49) and BB302 could be used in a PCR reaction with the mutated EPO *167C gene cloned in pUC19 or pBlueBac4.5 as template to generate a modified mutant EPO gene encoding the *167C mutein that would be suitable for expression in mammalian cell expression systems.

Endotoxin free plasmid DNAs are preferred for transfecting mammalian cells such as COS or dhfr⁻ CHO cells. Dhfr⁻ CHO cell lines can be obtained from a number of sources such as Dr. L. Chasin at Columbia University (CHO K1 DUKX B11) or from the American Type Culture Collection (CHO duk⁻, ATCC No. CRL-9096). The cells can be cultured in F12/DMEM medium supplemented with 10% FBS, glutamine, glycine, hypoxanthine, and thymidine (Lucas et al., 1996). Transfections can be carried out by electroporation or by using transfection reagents well known to those of skill in the art such as LipofectAMINE (Gibco BRL), using the vendor protocols and/or those described in the literature (Kaufman, 1990). One can select for dhfr⁺ trasfectants in F12/DMEM supplemented with 7% dialyzed FCS and lacking glutamine, glycine, hypoxanthine, and thymidine (Lucas et al., 1996). Alternatively one can select for G418 resistance (encoded by the NPT gene of pcDNA3.1) and subsequently screen transfectants for the dhfr⁺ phenotype. Dhfr⁺ clones can be expanded in selection medium and culture supernatants screened for EPO cysteine mutein production using commercially available EPO ELISA kits (available from R & D Systems) or by Western blot using anti-EPO antisera (available from R&D Systems). Clones expressing the EPO cysteine mutein can then be pooled and subjected to multiple rounds of selection for MTX resistance at increasing drug concentration as described by Kaufman (1990). After each round of MTX selection, individual clones can be tested for EPO cysteine mutein production. These procedures are well described in the literature and have been used to express a variety of heterologous protein in CHO cells (reviewed in Kaufman, 1990).

Preferably, the media used to grow the CHO cells expressing the EPO cysteine muteins should contain cystine or another cysteine blocking agent. The EPO cysteine muteins can be purified from the conditioned medium of CHO cells using protocols similar to those described by Imai et al. (1990). After removal of the CHO cells by centrifugation, the EPO cysteine muteins can be purified from the supernatant by column chromatography using techniques well known to those of skill in the art. The column chromatography steps employed for the purification of the EPO cysteine muteins could include Blue Sepharose, hydroxyapatite, reversed phase, hydrophobic interaction, size exclusion and ion-exchange chromatography.

EXAMPLE 20

Cloning, Expression and Purification of IFN-α2

A. Cloning DNA Sequences Encoding IFN-α2

There are at least 25 distinct IFN-α genes which encode proteins that share 70% or greater amino acid identity (Blatt et al., 1996). Due to the high degree of DNA sequence homology between IFN-α species, the IFN-α2 gene was cloned in two steps. First, the IFN-α2 gene was amplified by PCR from human genomic DNA using primers corresponding to unique sequences upstream and downstream of the IFN-α2 gene. This PCR product was cloned and sequenced to confirm that it encodes the IFN-α2 gene. Subsequently, the IFN-α2 coding sequence was modified by PCR and subcloned for expression in E. coli and site-directed mutagenesis. DNA encoding IFN-α2 was amplified by PCR from human genomic DNA (CLONTECH). PCR reactions were carried out with BB93 (5>CGCGAATTCGGATATGTAAA TAGATACA-CAGTG>3) (SEQ.ID.NO. 50) and BB94 (5>CGCAAGCT-TAAAAGATTTAAATCGTGTCATGGT>3) (SE-Q.ID.NO.51). BB93 anneals to genomic sequences ~300 bp upstream (i.e. 5' to) of the IFN-α2 coding sequence and contains an Eco RI site for cloning purposes. BB94 anneals to genomic sequences ~100 bp downstream (i.e. 3' to) of the IFN-α2 coding sequence and contains a Hind III site for cloning purposes. The resulting ~1 kb PCR product was digested with Eco RI and Hind III and cloned into similarly digested, and alkaline phosphatased, pcDNA3.1(+) (Invitrogen). A clone having the correct DNA sequence for IFN-α2 (Henco et al, 1985) was identified and designated pBBT160.

For cytoplasmic expression in E. coli the cloned IFN-α2 gene of pBBT160 was modified by PCR to incorporate a methionine codon immediately prior to the first residue (C1) of the mature IFN-α2 protein. A TAA stop codon was added following the carboxy-terminal residue, E165. At the same time, Xba I and Sal I sites were added and a Bgl II site was eliminated in order to provide convenient restriction sites for subsequent mutagenesis. In this reaction pBBT160 was used as template and amplified by primers BB99 5>CGCAAGCT-TCATATGTGTGATCTGCCTCAAACCCACAGCCTG GGTTCTAGAAGGACCTTGATGCTC>3) (SEQ.ID.NO. 52) and BB100 (5>CGCGAATTCTTATT CCTTACTTCT-TAAACTTTCTTGCAAGTTTGTCGACAAA-GAAAAGGATCTCATGAT>3) (SEQ.ID.NO. 53). BB99 anneals to the 5' end of the coding sequence of mature IFN-α2 and encodes an initiator methionine preceding the first amino acid of mature IFN-α2. BB99 introduces an Xba I site ~30 bp downstream of the initiator ATG, but the amino acid sequence of the protein is unaltered. A Hind III site and an Nde I site, which overlaps the ATG, were included for cloning purposes. The reverse primer, BB100, anneals to the 3' end of the coding sequence and adds a TAA stop codon. BB100 introduces a Sal I site ~30 bp upstream of the TAA codon and eliminates a naturally occurring Bgl II site located ~15 bp further upstream. As a result, the naturally occurring Bgl II site located ~185 bp downstream of the initiator ATG becomes a unique site. None of these alterations changed the amino acid sequence. An Eco RI site was added immediately downstream of the stop codon for cloning purposes. The ~520 bp PCR product was digested with Hind III and Eco RI, gel purified and cloned into similarly digested plasmid pcDNA3.1(+). One clone was determined to have the correct DNA sequence. This plasmid was designated pBBT164. For cytoplasmic expression in E. coli, the ~520 bp Nde I-Eco RI fragment of pBBT164 was cloned into similarly digested expression vector, pCYB 1, (New England Biolabs). The plasmid vector pCYB1 allows genes to be expressed as unfused proteins or as fusion proteins; this construct was created so that the protein is expressed as an unfused protein. The resulting plasmid was termed pBBT170 and encodes met-IFN-α2. The Nde I-Eco RI fragment of pBBT164 containing the met-IFN-α2 sequence also was subcloned into Nde I-Eco RI-digested pUC18 to generate plasmid pBBT168.

IFN-α2 also can be expressed in an active form in E. coli by secretion into the periplasmic space (Voss et al., 1994). Secreted IFN-α2 lacks an N-terminal methionine and has an amino acid sequence identical to naturally occurring IFN-α2. In order to express a secreted form of IFN-α2, the leader sequence of the E. coli heat-stable enterotoxin (STII) gene (Picken et al., 1983) was fused to the coding sequence for mature IFN-α2 via PCR. Because of its length, the STII sequence was added in two sequential PCR reactions. The first reaction used forward primer BB101 (5>GCATCTAT-GTTCGTTTTCTCTATCGCTACCAACGCT-TACGCATGTGATCT GCCTCAAACCCAC AGC>3) (SE-Q.ID.NO. 54) and reverse primer BB100 with pBBT164 (described above) as template. The 3' end (21 bp) of BB101 anneals to the 5' end of the coding sequence of mature IFN-α2. The 5' segment (39 nucleotides) of BB101 encodes a portion of the STII leader peptide. The ~550 bp PCR product of this reaction was gel purified and used as template for the second PCR reaction. The second PCR reaction used reverse primer BB100 and forward primer BB11 (5'-CCCCCTCTA-GACATATGAAG AAGAACATCGCATTCCTGCTG-GCATCTATGTTCGTTTTCTC TATCG-3') (SEQ.ID.NO. 7). BB11 adds the remainder of the STII leader peptide and contains an Nde I site overlapping the initiator ATG of the STII leader. The ~590 bp product of this reaction was digested with Nde I and Xba I. The ~100 bp Nde I-XbaI fragment containing the STII leader sequence and amino-terminal ~30 bp of IFN-α2, was gel-purified and ligated with pBBT168 [pUC18::met-IFN-α2] that had been digested with Nde I and Xba I, treated with alkaline phosphatase and gel purified. In this step the ~30 bp Nde I-Xba I amino-terminal segment of the met-IFN-α2 gene is replaced with the PCR derived ~100 bp Nde I-Xba I amino-terminal segment of the STII-IFN-α2 PCR product. The sequence of the resulting pUC18::STII-IFN-α2 construct was confirmed and that plasmid was designated pBBT177. For expression in *E. coli*, pBBT177 was digested with Nde I and Eco RI and the ~570 bp fragment containing the STII-IFN-α2 gene was gel-purified and cloned into the expression vector pCYB1 under the control of the tac promoter. The resulting plasmid was designated pBBT178.

B. Expression of rIFN-α2 in *E. coli*.

pBBT170, which encodes met-IFN-α2, and parental vector, pCYB1, were transformed into *E. coli* JM109. Experiments with these strains resulted in expression of met-IFNα-2. Secreted IFN-α2 is preferable to cytoplasmic met-IFN-α2 in that secreted IFN-α2 has the same amino acid sequence as naturally occurring IFN-α2.

For expression of secreted rIFN-α2, pBBT178 [pCYB1::STII-IFN-α2] and the parental vector pCYB1 were transformed into *E. coli* W3110. The resulting strains were designated BOB202: W3110(pBBT178) and BOB130: W3110 (pCYB1). We performed a series of experiments testing growth and rIFN-α2 expression of BOB202 in phosphate- or 2-(N-morpholino)ethanesulfonic acid (MES)-buffered LB media at initial pHs ranging from 5.0 to 7.0. Saturated overnight cultures were diluted to ~0.025 O.D. at $A_{600}$ in buffered LB containing 100 µg/ml ampicillin and incubated at 37° C. in shake flasks. When culture O.D.s reached ~0.3-0.5, IPTG was added to a final concentration of 0.5 mM to induce expression of rIFN-α2. For initial experiments, cultures were sampled at 0, 1, 3, 5 and ~16 h post-induction. Samples of induced and uninduced cultures were analyzed by SDS-PAGE on precast 14% Tris-glycine polyacrylamide gels stained with Coomassie Blue. In addition to the expected ~19 kDa processed form of IFN-α2, we observed a higher than expected molecular weight (~21.5 kDa) form of the protein. The higher molecular weight form could result from lack of proteolytic processing of the STII leader peptide; the molecular weight of the leader peptide is consistent with this hypothesis. Our results indicated that lower pH enhanced accumulation of the correctly sized rIFN-α2 band. We observed that at or above pH 6.5 the 21.5 kDa form was predominant, while at or below pH 6.0 a band of ~19 kDa, which comigrated with an *E. coli*-expressed rIFN-α2 standard (Endogen, Inc.), was the predominant form of the protein. At or below pH 6.0, the 19 kDa band accounted for at least 80% and probably greater than 90% of the IFN-α2 expressed by the *E. coli* cells. Based on these findings, further expression experiments used LB medium buffered with 100 mM MES to a pH of 5.5. Voss et al. (1994) also reported secretion of IFN-α2 to the *E. coli* periplasm using the STII leader sequence. They also observed that the proportion of rIFN-α2 present in the 21.5 kDa band was reduced, and the proportion migrating at 19 kDa was increased when culture pH was maintained at 6.7 as compared to 7.0. At pH 7.0, Voss et al. (1994) reported that 10-30% of the STII:IFN-α2 fusion protein was processed to yield the 19 kDa mature IFN-α2 protein. The percentage of correctly processed 19 kDa IFN-α2 protein could be increased to 50-60% by growing the *E. coli* at pH 6.7. However, even at this pH, a substantial amount (40-50%) of the STII: IFN-α2 fusion protein remained unprocessed, reducing the yield of correctly processed 19 kDa IFN-α2. Voss et al. (1994) suggested that pH 6.7 was optimal for maximizing the amount of secreted rIFN-α2 migrating at 19 kDa. Voss et al. (1994) varied several growth parameters to attempt to increase the percentage of correctly processed 19 kDa IFN-α2 protein to greater than 50-60%, but were unsuccessful. Our data indicate that lowering the pH to below 6.5, and preferably to 5.5 to 6.0, maximizes the ratio of cleaved (19 kDa) to uncleaved (21.5 kDa) rIFN-α2 product. At these lower pHs, the percent of correctly processed 19 kDa IFN-α2 is increased to at least 80% and probably 90-100% of the total IFN-α2 synthesized by the cells.

Cultures expressing rIFN-α2 were subjected to osmotic shock based on the procedure of Koshland and Botstein (1980). This procedure ruptures the *E. coli* outer membrane and releases the contents of the periplasm into the surrounding medium. Subsequent centrifugation separates the soluble periplasmic components (recovered in the supernatant) from cytoplasmic, insoluble periplasmic, and cell-associated components (recovered in the pellet). Approximately 25-50% of the 19 kDa rIFN-α2 synthesized by BOB202 was recovered in the supernatant. None of the 21.5 kDa form of rIFN-α2 was observed in the soluble periplasmic fraction.

C. Large-Scale Expression and Purification of rIFN-α2 in *E. coli:*

In order to purify the wild type rIFN-α2 protein, fresh saturated overnight cultures of BOB202 were inoculated at ~0.02 OD @ $A_{600}$ in LB 100 mM MES (pH5.5) containing 100 µg/ml ampicillin. Typically, a 325 ml culture was grown in a 2 liter shake flask at 37° C. in a gyrotory shaker water bath at ~160-200 rpm. When cultures reached a density of ~0.3-0.4 OD, IPTG was added to a final concentration of 0.5 mM. The induced cultures were then incubated for ~16 h. Cultures were subjected to osmotic shock based on the procedure of Hsuing et. al. (1986). The cells were pelleted by centrifugation and resuspended at ~25 OD/ml in ice cold 20% sucrose, 10 mM Tris-HCl (pH 8.0). Resuspended cells were incubated on ice for 15 min and centrifuged at 9500×g for 10 min. Pellets were then resuspended in ice cold 10 mM Tris-HCl pH (8.0), incubated on ice for 15 min and centrifuged at 9500×g for 10 min. The resulting supernatant (the osmotic shock lysate) was either processed immediately or stored at −80° C.

rIFN-α2 was purified as follows. The pH of the supernatant from the osmotic shock was adjusted to 3, centrifuged to remove any precipitate, and loaded onto a 5 ml Pharmacia HiTrap S-Sepharose column equilibrated in 20 mM MES pH 5.0 (Buffer A). The bound proteins were eluted with a linear salt gradient from 0-100% Buffer B (500 mM NaCl, 20 mM MES, 10% ethylene glycol). Column fractions were analyzed by non-reducing SDS-PAGE. rIFN-α2 eluted at approximately 225-235 mM NaCl. Fractions that were enriched for rIFN-α2 were pooled and further fractionated on a 1 mL $Cu^{++}$ IMAC (Immobilized Metal Affinity Chromatography) Hi Trap column previously equilibrated in 40 mM sodium phosphate pH 6.0, 1 M NaCl, 0.1% Tween 20. rIFN-α2 was eluted with a reverse pH gradient from 5.5 to 4.1 in 40 mM sodium phosphate, 1 M NaCl, 0.1% Tween 20. rIFN-α2 eluted after the gradient reached 100% buffer B, when the pH of the eluate finally reached pH 4.1. Fractions from the $Cu^{++}$ IMAC column that contained purified, properly folded rIFN-α2 were pooled and stored as frozen aliquots at −80° C. A minor rIFN-α2 variant was detectable in some of the earlier eluting fractions. This variant, which results from incomplete disulfide formation and is biologically active, has been described previously (Khan and Rai, 1990). Fractions containing this variant were not added to the final pool of purified rIFN-α2. The final yield of rIFN-α2, as determined by absorbance at 280 nm and by Bradford analysis, was about 400 µg from 250 ml of culture. Reduced IFN-α2 migrates with a slightly larger apparent molecular weight than non-reduced IFN-α2 when analyzed by SDS-PAGE (Morehead et al., 1984). This apparent molecular weight change is due to the reduction of the native disulfides in IFN-α2. Our rIFN-α2 comigrated with the commercial rIFN-α2 standard under both reducing and non-reducing conditions.

D. In Vitro Bioactivity of Wild Type rIFN-α2.

IFN-α bioactivity can be measured using in vitro antiviral assays or cell proliferation inhibition assays. We developed a cell growth inhibition assay to measure bioactivity of wild type rIFN-α2. The human Daudi B cell line (American Type Culture Collection) is sensitive to the growth inhibiting properties of IFN-α and is routinely used to measure bioactivity of IFN-α (Horoszewicz et al., 1979; Evinger and Pestka, 1981). Daudi cells were maintained in RPMI 1640 media supplemented with 10% FBS, 50 units/ml penicillin and 50 µg/ml streptomycin. For bioassays, the cells were washed three times with RPMI 1640 media and resuspended at a concentration of $4 \times 10^5$ cells/ml in RPMI 1640 media containing 10% FBS, 50 units/ml penicillin and 50 µg/ml streptomycin. Fifty µl ($2 \times 10^4$ cells) of the cell suspension were aliquotted per test well of a flat bottom 96 well tissue culture plate. Serial 3-fold dilutions of the protein samples to be tested were prepared in RPMI 1640 media containing 10% FBS, 50 units/ml penicillin and 50 µg/ml streptomycin. Fifty µl of the diluted protein samples were added to the test wells and the plates incubated at 37° C. in a humidified 5% $CO_2$ tissue culture incubator. Protein samples were assayed in triplicate wells. After 4 days, 20 µl of CellTiter 96 AQueous One Solution Reagent (Promega Corporation) was added to each well and the plates incubated at 37° C. in the tissue culture incubator for 1-4 h. Absorbance was read at 490 nm using a microplate reader. Control wells contained media but no cells. Mean absorbance values for the triplicate control wells were subtracted from mean values obtained for each set of triplicate test wells. Serial dilutions of E. coli-expressed rIFN-α2 (Endogen, Inc.) were analyzed in parallel. $IC_{50}$s (the concentration of protein required for half maximal growth inhibition) were calculated for each sample and used to compare bioactivities of the proteins.

Proliferation of the Daudi cell line is strongly inhibited by rIFN-α2, as evidenced by a dose-dependent decrease in absorbance values. Commercial rIFN-α2 (Endogen) and wild type rIFN-α2 prepared by us reached the same maximal level of growth inhibition, within the error of the assay, and had similar mean $IC_{50}$s of 13-16 pg/ml (Table 4). $IC_{50}$ values for these proteins ranged from 7-29 pg/ml in assays performed on different days (Table 4); therefore comparisons between proteins were made on samples analyzed on the same day.

EXAMPLE 21

Construction, Expression, Purification and Bioactivity of IFN-α2 Cysteine Muteins A. Construction of IFN-α2 Cysteine Muteins.

Seventeen mutant IFN-α2 genes were constructed using site-directed PCR-based mutagenesis procedures similar to those described in Example 4. We constructed one mutein in the amino-terminal region proximal to helix A [Q5C]; six muteins in the A-B loop [N45C, Q46C, F47C, Q48C, A50C and 43C44 (an insertion of a cysteine between residues 43 and 44); one mutein [D77C] in the short, two residue, BC loop; four muteins in the CD loop [Q101C, T106C, E107C, and T108C]; three muteins in the carboxy-terminal region distal to the E helix [5163C, E165C, and *166C (the addition of a cysteine residue to the natural carboxy-terminus)]. We also constructed muteins C1S and C98S, which eliminate the naturally occurring, but non-essential, C1-C98 disulfide (Lydon et al., 1985; Morehead et al., 1994). The C1S substitution in the amino-terminal region proximal to helix A generates a free cysteine in the C helix (C98), whereas the C98S substitution in the C helix generates a free cysteine in the region proximal to helix A (C1).

For mutagenesis, PCR primer oligonucleotides were designed to incorporate nucleotide changes that resulted in the incorporation of a cysteine residue at the chosen position within the IFN-α2 coding sequence. Where feasible, the mutagenic oligo also was designed to span a nearby restriction site that could be used to clone the mutagenized PCR fragment into an appropriate plasmid. When no useful restriction site was located sufficiently near the position of the mutation, the technique of "mutagenesis by overlap extension" was employed (Horton et al., 1993). The template used for the mutagenic PCR reactions was plasmid pBBT177 (described in Example 20) in which the STII-IFN-α2 gene is cloned as an Nde I-Eco RI fragment into pUC18. The PCR products were digested with appropriate restriction endonucleases, gel-purified and ligated with pBBT177 vector DNA that had been cut with those same restriction enzymes, alkaline phosphatase treated, and gel-purified. Transformants from these ligations were grown up and plasmid DNAs isolated and sequenced. The sequence of the entire cloned mutagenized PCR fragment was determined to verify the presence of the mutation of interest, and the absence of any additional mutations that potentially could be introduced by the PCR reaction or by the synthetic oligonucleotide primers.

The substitution mutation Q5C was constructed using the technique of "mutagenesis by overlap extension" as described in Example 4. The initial, or "primary" PCR reactions for the Q5C construction were performed in a 50 µl reaction volume in 1× Promega PCR buffer containing 1.5 mM $MgCl_2$, each primer at 0.2 µM, each of dATP, dGTP, dTTP and dCTP at 200 µM, 1 ng of template plasmid pBBT177 (described in Example 20), 1.5 units of Taq Polymerase (Promega), and 0.25 units of Pfu Polymerase (Stratagene). Reactions were performed in a Robocycler Gradient 96 thermal cycler (Stratagene). The reaction program entailed: 96° C. for 3 minutes, 25 cycles of [95° C. for 1 minute, 60° C. for 1.25 minutes, 72° C. for 1 minute] followed by a hold at 6° C. The primer pairs used were [BB125×BB130] and [BB126×BB129]. BB125 (5>CTATGC GGCATCAGAGCAGATA>3) (SEQ.ID.NO. 55) anneals to the pUC18 vector sequence ~20 bp upstream of the cloned IFN-α2 sequence. BB126 (5>TGTGGAATTGTGAGCG-GATAAC>3) (SEQ.ID.NO. 56) anneals to the pUC18 vector sequence ~40 bp downstream of the cloned IFN-α2 sequence. BB129 and BB130 are complementary mutagenic oligonucleotides that change the CAA codon for Q5 to a TGT codon for cysteine. The sequence of BB129 is (5>TGT-GATCTGCCTTGTACCCACAGCCTG>3) (SEQ.ID.NO. 57) and the sequence of BB130 is (5>CAGGCTGT GGGTA-CAAGGCAGATCACA>3) (SEQ.ID.NO. 58). The [BB125× BB130] and [BB126×BB129] PCR reactions gave products of the expected sizes: ~140 bp for [BB125×BB130] and ~560 bp for [BB126×BB129]. The PCR products were "cleaned up" using the QIAquick PCR Purification Kit (Qiagen) according to the vendor protocol, run out on a 2% agarose gel, gel-purified using a QIAEX II Gel Extraction Kit (Qiagen) according to the vendor protocol and recovered in 20 µl 10 mM Tris-HCl (pH 8.5). These two mutagenized fragments were then "spliced" together in the subsequent, or "secondary" PCR reaction. In this reaction 2 µl of each of the gel-purified PCR products of the primary reactions were used as template and BB125 and BB126 were used as primers. The reaction volume was 100 µl and 2.5 units of Taq Polymerase and 0.5 units of Pfu Polymerase were employed. Otherwise, the reaction conditions were identical to those used in the primary reactions. An aliquot of the secondary PCR was analyzed by agarose gel electrophoresis and the expected band of ~670 bp was observed. The bulk of the secondary PCR reaction was "cleaned up" using the QIAquick PCR Purification (Qiagen), digested with Nde I and Xba I (New England BioLabs) according to the vendor protocols, "cleaned up" using the QIAquick PCR Purification Kit and run out on a 2% agarose gel. The ~100 bp Nde I-Xba I fragment of interest was gel purified using a QIAEX II Gel Extraction Kit (Qiagen) according to the vendor protocol. This fragment was ligated with pBBT177 (described in Example 20) that had been cut with Nde I and Xba I, treated with calf intestinal alkaline phosphatase (New England BioLabs) and gel purified. The ligation reaction was used to transform *E. coli* and plasmids from resulting transformants were sequenced to identify a clone containing the Q5C mutation and having the correct sequence throughout the ~100 bp Nde I-Xba I segment.

The substitution mutation C1S was constructed and sequence verified using the protocols detailed above for Q5C except that complementary mutagenic primers BB128 (5>AGGCAGATC AGATGCGTAAGC>3) (SEQ.ID.NO. 59) and BB127 (5>GCTTACGCATCTGATCTGCCT>3) (SEQ.ID.NO. 60), which change the TGT codon for C1 to a TCT codon for serine, replaced BB130 and BB129 respectively in the primary PCR reactions. The [BB125×BB1128] and [BB126×BB127] PCR reactions gave products of the expected sizes: ~120 bp for [BB125×BB128] and ~570 bp for [BB126×BB127].

The substitution mutation N45C was constructed and sequence verified using the protocols detailed above for Q5C with the following differences. Complementary mutagenic primers BB134 (5>CTTTTG GAACTGGCAGC-CAAACTCCTC>3) (SEQ.ID.NO. 61) and BB133 (5>GAG-GAGTTTGGCTGCCAGTTCCAAAAG>3) (SEQ.ID.NO. 62), which change the AAC codon for N45 to a TGC codon for cysteine, replaced BB130 and BB129 respectively in the primary PCR reactions. The [BB125×BB134] and [BB126×BB133] PCR reactions gave products of the expected sizes: ~255 bp for [BB125×BB134] and ~440 bp for [BB126×BB133]. The product of the secondary PCR reaction was "cleaned up" using the QIAquick PCR Purification (Qiagen), digested with Bgl II and Xba I (New England BioLabs) according to the vendor protocols, "cleaned up" using the QIAquick PCR Purification Kit and run out on a 2% agarose gel. The ~155 bp Bgl II-Xba I fragment of interest was gel purified using a QIAEX II Gel Extraction Kit (Qiagen) according to the vendor protocol. This fragment was ligated with pBBT177 that had been cut with Bgl II and Xba I, treated with calf intestinal alkaline phosphatase (New England BioLabs) and gel purified. The ligation reaction was used to transform *E. coli* and plasmids from resulting transformants were sequenced to identify a clone containing the N45C mutation and having the correct sequence throughout the ~155 bp Bgl II-Xba I segment.

The substitution mutation F47C was constructed and sequence verified using the protocols detailed above for N45C with the following differences. Complementary mutagenic primers BB136 (5>TTCAGC CTTTTG-GCACTGGTTGCCAAA>3) (SEQ.ID.NO. 63) and BB135 (5>TTTGGCAACCAGTGCCAAAAGGCTGAA>3) (SEQ.ID.NO. 64), which change the TTC codon for F47 to a TGC codon for cysteine, replaced BB134 and BB133 respectively in the primary PCR reactions. The [BB125×BB136] and [BB126×BB135] PCR reactions gave products of the expected sizes: ~260 bp for [BB125×BB136] and ~435 bp for [BB126×BB135].

The insertion mutation 43C44 was constructed and sequence verified using the protocols detailed above for N45C with the following differences. Complementary mutagenic primers BB132 (5>TTCAGCCTT TTG-GCACTGGTTGCCAAA>3) (SEQ.ID.NO. 65) and BB131 (5>TTTGGCAACCAGTGCCAAAAGGCTGAA>3) (SEQ.ID.NO. 66), which insert a TGC codon for cysteine between the codons encoding amino acid residues 43 and 44, replaced BB134 and BB133 respectively in the primary PCR reactions. The [BB125×BB132] and [BB126×BB131] PCR reactions gave products of the expected sizes: ~250 bp for [BB125×BB132] and ~445 bp for [BB126×BB131].

The substitution mutation Q46C was constructed and sequence verified using the protocols detailed above for N45C with the following differences. Complementary mutagenic primers BB154 (5>AGCCTT TTGGAAACAGT-TGCCAAACTC>3) (SEQ.ID.NO. 67) and BB153 (5>GAGTTTGGCAACTGTTTCCAAAAGGCT>3) (SEQ.ID.NO. 68), which change the CAG codon for Q46 to a TGT codon for cysteine, replaced BB134 and BB133 respectively in the primary PCR reactions. The primary reactions were performed in a Perkin-Elmer GeneAmp® PCR System 2400 thermal cycler. The reaction program entailed: 95° C. for 5 minutes, 30 cycles of [95° C. for 30 seconds, 62° C. for 30 seconds, 72° C. for 1 minute] followed by 72° C. for 7 minutes and a hold at 4° C. The [BB125×BB154] and [BB126×BB153] PCR reactions gave products of the expected sizes: ~260 bp for [BB125×BB154] and ~440 bp for [BB126×BB153]. The secondary PCR reaction was also performed in a Perkin-Elmer GeneAmp® PCR System 2400 thermal cycler. This reaction program entailed: 96° C. for 5 minutes, 25 cycles of [95° C. for 30 seconds, 60° C. for 30 seconds, 72° C. for 1 minute] and a hold at 4° C. Following digestion with Bgl II and Xba I, the products of this reaction were cleaned up using the QIAquick PCR Purification Kit but not gel purified prior to ligation.

The substitution mutation Q48C was constructed and sequence verified using the protocols detailed above for Q46C with the following differences. Complementary mutagenic primers BB156 (5>GGTTTCA GCCTTACA-GAACTGGTTGCC>3) (SEQ.ID.NO. 69) and BB155 (5>GGCAACCAGTTCTGTAAGGCTGAAACC>3) (SEQ.ID.NO. 70), which change the CAA codon for Q48 to a TGT codon for cysteine, replaced BB154 and BB153 respectively in the primary PCR reactions. The [BB125×BB156] and [BB126×BB155] PCR reactions gave products of the expected sizes: ~265 bp for [BB125×BB156] and ~435 bp for [BB126×BB155].

The substitution mutation A50C was constructed and sequence verified using the protocols detailed above for Q46C with the following differences. Complementary mutagenic primers BB158 (5>AGGGATGGT TTCA-CACTTTTGGAACTG>3) (SEQ.ID.NO. 71) and BB157

(5>CAG TTCCAAAAGTGTGAAAC CATCCCT>3) (SEQ.ID.NO. 72), which change the GCT codon for A50 to a TGT codon for cysteine, replaced BB154 and BB153 respectively in the primary PCR reactions. The [BB125×BB158] and [BB126×BB157] PCR reactions gave products of the expected sizes: ~270 bp for [BB125×BB156] and ~440 bp for [BB126×BB155].

The substitution mutation D77C was constructed and sequence verified using the protocols detailed above for Q5C with the following differences. Complementary mutagenic primers BB138 (5>TAGGAG GGTCTCACACCAAGCAGCAGA>3) (SEQ.ID.NO. 73) and BB137 (5>TCTGCTGCTTGGTGTGAGACCCTCCTA>3) (SEQ.ID.NO. 74), which change the GAT codon for D77 to a TGT codon for cysteine, replaced BB130 and BB129 respectively in the primary PCR reactions. The [BB125×BB138] and [BB126×BB137] PCR reactions gave products of the expected sizes: ~350 bp for [BB125×BB138] and ~345 bp for [BB126×BB137]. The product of the secondary PCR reaction was "cleaned up" using the QIAquick PCR Purification (Qiagen), digested with Bgl II and Sal I (New England BioLabs) according to the vendor protocols, "cleaned up" using the QIAquick PCR Purification Kit and run out on a 2% agarose gel. The ~275 bp Bgl II-Sal I fragment of interest was gel purified using a QIAEX II Gel Extraction Kit (Qiagen) according to the vendor protocol. This fragment was ligated with pBBT177 that had been cut with Bgl II and Sal I, treated with calf intestinal alkaline phosphatase (New England BioLabs) and gel purified. The ligation reaction was used to transform *E. coli* and plasmids from resulting transformants were sequenced to identify a clone containing the D77C mutation and having the correct sequence throughout the ~275 bp Bgl II-Sal I segment.

The substitution mutation T106C was constructed and sequence verified using the protocols detailed above for D77C with the following differences. Complementary mutagenic primers BB140 (5>CAGGGGAGTCTCACACACCCCACCCC>3) (SEQ.ID.NO. 75) and BB139 (5>GGGGTGGGGGTGTGTGAGACTCCCCTG>3) (SEQ.ID.NO. 76), which change the ACA codon for T106 to a TGT codon for cysteine, replaced BB138 and BB137 respectively in the primary PCR reactions. The [BB125×BB140] and [BB126×BB139] PCR reactions gave products of the expected sizes: ~435 bp for [BB125×BB140] and ~260 bp for [BB126×BB139].

The substitution mutation T108C was constructed and sequence verified using the protocols detailed above for D77C with the following differences. Complementary mutagenic primers BB142 (5>CTTCAT CAGGGGACACTCTGTCACCCC>3) (SEQ.ID.NO. 78) and BB141 (5>GGGGTGACAGAGTGTCCCCTGATGAAG>3) (SEQ.ID.NO. 79), which change the ACT codon for T108 to a TGT codon for cysteine, replaced BB138 and BB137 respectively in the primary PCR reactions. The [BB125×BB142] and [BB126×BB141] PCR reactions gave products of the expected sizes: ~440 bp for [BB125×BB142] and ~250 bp for [BB126×BB141].

The substitution mutation Q101C was constructed and sequence verified using the protocols detailed above for D77C with the following differences. Complementary mutagenic primers BB162 (5>CACCCC CACCCCACATATCACACAGGC>3) (SEQ.ID.NO. 80) and BB161 (5>GCCTGTGTGATATGTGGGGTGGGGGTG>3) (SEQ.ID.NO. 81), which change the CAG codon for Q101 to a TGT codon for cysteine, replaced BB138 and BB137 respectively in the primary PCR reactions. The primary reactions were performed in a Perkin-Elmer GeneAmp® PCR System 2400 thermal cycler. The reaction program entailed: 95° C. for 5 minutes, 30 cycles of [95° C. for 30 seconds, 62° C. for 30 seconds, 72° C. for 1 minute] followed by 72° C. for 7 minutes and a hold at 4° C. The [BB125×BB162] and [BB126×BB161] PCR reactions gave products of the expected sizes: ~425 bp for [BB125×BB162] and ~275 bp for [BB126×BB161]. The secondary PCR reaction was also performed in a Perkin-Elmer GeneAmp® PCR System 2400 thermal cycler. This reaction program entailed: 96° C. for 5 minutes, 25 cycles of [95° C. for 30 seconds, 60° C. for 30 seconds, 72° C. for 1 minute] and a hold at 4° C. Following digestion with Bgl II and Sal I, the products of this reaction were cleaned up using the QIAquick PCR Purification Kit but not gel purified prior to ligation.

The substitution mutation E107C was constructed and sequence verified using the protocols detailed above for Q101C with the following differences. Complementary mutagenic primers BB164 (5>CAT CAGGGGAGTACATGTCACCCCCAC>3) (SEQ.ID.NO. 81) and BB163 (5>GTGGGGGTGACATGTACTCCCCTG ATG>3) (SEQ.ID.NO. 82), which change the GAG codon for E107 to a TGT codon for cysteine, replaced BB162 and BB161 respectively in the primary PCR reactions. The [BB125×BB164] and [BB126×BB163] PCR reactions gave products of the expected sizes: ~440 bp for [BB125×BB164] and ~255 bp for [BB126×BB163].

The substitution mutation C98S was constructed and sequence verified using the protocols detailed above for Q101C with the following differences. Complementary mutagenic primers BB160 (5>CCC CTGTATCACAGAGGCTTCCAGGTC>3) (SEQ.ID.NO. 83) and BB159 (5>GACCTGGAAGCCTCTGTGATACA GGGG>3) (SEQ.ID.NO. 84), which change the TGT codon for C98S to a TCT codon for serine, replaced BB162 and BB161 respectively in the primary PCR reactions. The [BB125×BB160] and [BB126×BB159] PCR reactions gave products of the expected sizes: ~415 bp for [BB125×BB160] and ~285 bp for [BB126×BB159].

The cysteine substitution mutation S163C was constructed as follows. The mutagenic reverse oligonucleotide BB143 (5>CGCGAATTCTTATTCCTTACATCTTAAACTTTC>3) (SEQ.ID.NO. 85) was designed to change the codon AGT for serine at position 163 to a TGT encoding cysteine and to span the nearby Eco RI site. This oligo was used in PCR with the forward, non-mutagenic, primer BB125. A 50 µl PCR reaction was performed in 1× Promega PCR buffer containing 1.5 mM MgCl$_2$, each primer at 0.2 µM, each of dATP, dGTP, dTTP and dCTP at 200 µM, 1 ng of template plasmid pBBT131 1.5 units of Taq Polymerase (Promega), and 0.25 units of Pfu Polymerase (Stratagene). Reactions were performed in a Robocycler Gradient 96 thermal cycler (Stratagene). The reaction program entailed: 96° C. for 3 minutes, 25 cycles of [95° C. for 1 minute, 60° C. for 1.25 minutes, 72° C. for 1 minute] followed by a hold at 6° C. A 5 µl aliquot of the PCR reaction was analyzed by agarose gel electrophoresis and found to produce a single fragment of the expected size ~610 bp. The remainder of the reaction was "cleaned up" using the QIAquick PCR Purification (Qiagen) according to the vendor protocol, digested with Sal I and Eco RI (New England BioLabs) according to the vendor protocols, ethanol-precipitated, resuspended in 20 µl of 10 mM Tris-HCl pH 8.5 and run out on a 2% agarose gel. The ~42 bp Sal I-Eco RI fragment of interest was gel purified using a QIAEX II Gel Extraction Kit (Qiagen) according to the vendor protocol. This fragment was ligated with pBBT132 that had been cut with Sal I and Eco RI, treated with calf intestinal alkaline phosphatase (New England BioLabs) and gel purified. The ligation reaction was used to transform E. coli and plasmids from resulting transformants were sequenced to identify a clone containing the E107C mutation and to have the correct sequence throughout the ~42 bp Sal I-Eco RI segment.

A mutation was also constructed that added a cysteine following the carboxyterminal amino acid of the IFN-α2 coding sequence. This mutant, termed *167C was constructed using the protocols described above for the construction of the S163C mutant with the following differences. The mutagenic reverse oligonucleotide BB144 (5>CGCGAAT-TCTTAACATTCCTTACTTCTTAAACTTTC>3) (SE-Q.ID.NO. 86) which adds a TGT codon for cysteine between the GAA codon for E165 and the TAA stop codon and spans the nearby Eco RI site was used in the PCR reaction in place of BB143.

The substitution mutation E165C was constructed and sequence verified using the protocols detailed above for S163C with the following differences. The mutagenic reverse oligonucleotide BB165 (5>CGCGAATTCTTA ACACT-TACTTCTTAAACT>3) (SEQ.ID.NO. 87) which changes the GAA codon for E165 to a TGT codon for cysteine and spans the nearby Eco RI site was used in the PCR reaction in place of BB143. The PCR reaction was performed in a Perkin-Elmer GeneAmp® PCR System 2400 thermal cycler. The reaction program entailed: 95° C. for 5 minutes, 30 cycles of [95° C. for 30 seconds, 62° C. for 30 seconds, 72° C. for 1 minute] followed by 72° C. for 7 minutes and a hold at 4° C. Following digestion with Eco RI and Sal I, the products of this reaction were cleaned up using the QIAquick PCR Purification For expression in E. coli as proteins secreted to the periplasmic space, the STII-IFN-α2 genes encoding the 17 muteins were excised from the pUC18-based pBBT177 derivatives as Nde I-Eco RI fragments of ~590 bp and subcloned into the pCYB1 expression vector that had been used to express wild type STII-IFNα-2. For expression experiments, these plasmids were introduced into E. coli W3110.

Using procedures similar to those described here, one can construct other cysteine muteins of IFN-α2. The cysteine muteins can be substitution mutations that substitute cysteine for a natural amino residue in the IFN-α2 coding sequence, insertion mutations that insert a cysteine residue between two naturally occurring amino acids in the IFN-α2 coding sequence, or addition mutations that add a cysteine residue preceding the first amino acid, C1, of the IFN-α2 coding sequence or add a cysteine residue following the terminal amino acid residue, E165, of the IFN-α2 coding sequence. The cysteine residues can be substituted for any amino acid, or inserted between any two amino acids, anywhere in the IFN-α2 coding sequence. Preferred sites for substituting or inserting cysteine residues in IFN-α2 are in the region preceding Helix A, the A-B loop, the B-C loop, the C-D loop, the D-E loop and the region distal to Helix E. Other preferred sites are the first or last three amino acids of the A, B, C, D and E Helices. Preferred residues in these regions for creating cysteine substitutions are D2, L3, P4, T6, H7, S8, Q20, R22, K23, S25, F27, S28, K31, D32, R33, D35, G37, F38, Q40, E41, E42, F43, G44, K49, T52, N65, S68, T69, K70, D71, S72, S73, A74, A75, D77, E78, T79, Y89, Q90, Q91, N93, D94, E96, A97, G102, V103, G104, V105, P109, M111, K112, E113, D114, S115, K131, E132, K133, K134, Y135, S136, A139, S152, S154, T155, N156, L157, Q158, E159, S160, L161, R162, and K164. Cysteine residues also can be inserted immediately preceding or following these amino acids. Another preferred site for adding a cysteine residue would be preceding C1, which we refer to as *-1C.

One also can construct IFN-α2 muteins containing a free cysteine by substituting another amino acid for one of the naturally-occurring cysteine residues in IFN-α2. The naturally-occurring cysteine residue that normally forms a disulfide bond with the substituted cysteine residue is now free. The non-essential cysteine residue can be replaced with any of the other 19 amino acids, but preferably with a serine or alanine residue. A free cysteine residue also can be introduced into IFN-α2 by chemical modification of a naturally occurring amino acid using procedures such as those described by Sytkowski et al. (1998).

Using procedures similar to those described in Examples 20-22, one can express the proteins in E. coli, purify the proteins, PEGylate the proteins and measure their bioactivities in an in vitro bioassay. The IFN-α2 muteins also can be expressed in eukaryotic cells such as insect or mammalian cells, using procedures similar to those described in Examples 16-20, or related procedures well known to those skilled in the art.

B. E. coli Expression of rIFN-α2 Cysteine Muteins.

To assess expression, cultures of the rIFN-α2 muteins were grown and induced as described above for wild type rIFN-α2. Typically, 45 ml cultures were grown in 250 ml shake flasks at 37° C. in a gyrotory shaker water bath at ~180-200 rpm. We observed that vigorous aeration of shake flask cultures results in reduced levels of IFN-α2 protein in the supernatants of the osmotic shock lysates. Therefore we routinely used conditions that were sub-optimal for aeration but preferable for soluble rIFN-α2 and rIFN-α2 mutein production. The induced cultures were incubated for ~16 h, harvested and subjected to osmotic shock as detailed above for wild-type rIFN-α2 with the exception that cystine was added to a final concentration of 5 mM to the buffers used for the osmotic shock procedure. Adding cystine to the osmotic shock buffers resulted in significantly improved chromatographic properties for the first two muteins analyzed, Q5C and S163C. Interferon muteins not treated with cystine consistently eluted from the S-Sepharose column as broad bands, which, when analyzed by non-reducing SDS-PAGE, showed multiple molecular weight species at and around the expected monomer molecular weight. These species most likely represent misfolded or incompletely folded interferon variants. In contrast, interferon muteins treated with cystine during the osmotic shock procedure eluted from the S-Sepharose column as sharp bands, which, when analyzed by non-reducing SDS-PAGE, consisted of only one interferon species that co-migrated with the interferon wild type standard. Recoveries of the purified interferon muteins from the S-Sepharose column also were 1.5- to 2-fold greater when cystine was included in the osmotic shock buffers. Based upon these results, 5 mM cystine was added to the osmotic shock buffers used to purify all the cysteine muteins.

SDS-PAGE analysis of the osmotic shock supernatants of the muteins showed most to have reduced (as compared to wild type) levels of the 19 kDa rIFN-α2 band. Two muteins, Q5C and S163C, were expressed at levels equivalent to wild type interferon, and several hundred micrograms of each of these muteins were readily purified as detailed below. Eight muteins (C1S, 43C44, N45C, Q46C, Q48C, A50C, D77C and T108C) were essentially undetectable in osmotic shock supernatants. The remaining seven muteins (F47C, C98S, Q101C, T106C, E107C, E165C, *166C) were detected at varyingly reduced levels (as compared to wild type) in osmotic shock supernatants. Some of these muteins (T106C, C98S, E107C, and Q101C) were purified from osmotic shock supernatants, but only small quantities of the pure proteins were recovered. Certain muteins, C98S, Q101C, T106C, E107C and *166C, were expressed at relatively high levels but accumulated primarily in an insoluble form, presumably in the periplasm. These proteins comigrated with wild type rIFN-α2 standards under reducing conditions indicating that the STII leader had been removed. Qualitative assessments of relative expression levels of the muteins are summarized in Table 4.

C. Purification of rIFN-α2 Cysteine Muteins.

In order to purify the rIFN-α2 muteins, typically, a 325 ml culture in a 2 liter shake flask, or a 500 ml culture in a 2 liter baffled shake flask, were grown at 37° C. in a gyrotory shaker water bath (New Brunswick Scientific) ~170-220 rpm. Cultures were grown, induced, harvested, and subjected to osmotic shock as described in Example 20. Resulting osmotic shock supernatants were processed immediately or stored at −80° C.

The soluble IFN-α2 muteins in the osmotic shock supernatants were purified using S-Sepharose and $Cu^{++}$ IMAC chromatography as detailed above for purification of wild type rIFN-α2. All of the muteins tested bound tightly to the copper column and eluted under conditions similar to wild-type rIFN-α2. This result suggests that the conformations of the cysteine muteins are similar to that of native rIFN-α2, at least in the regions that comprise the metal-binding pocket.

Non-reducing SDS-PAGE analysis of the purified Q5C, C98S, Q101C, T106C, E107C, S163C, and *166C cysteine muteins showed that the muteins were recovered predominantly as monomers, migrating at the expected molecular weight of ~19 kDa. C98S migrated with a slightly higher molecular weight than the other rINF-α2 muteins due to the absence of the native Cys1-Cys-98 disulfide bond. Some of the purified muteins contained small amounts of disulfide-linked rIFN-α2 dimers. The molecular weights of the dimer species were approximately 37-38 kDa.

D. Bioactivities of rIFN-α2 Cysteine Muteins.

Biological activities of the purified Q5C and 5163C rIFN-α2 cysteine muteins were measured in the Daudi growth inhibition assay described in Example 20. Protein concentrations were determined using Bradford or BCA protein assay kits (Bio-Rad Laboratories and Pierce). Commercial wild type rIFN-α2 and rIFN-α2 prepared by us were analyzed in parallel on the same days to control for interday variability in the assays. The muteins inhibited proliferation of Daudi cells to the same extent as the wild type rIFN-α2 control proteins, within the error of the assay. The mean $IC_{50}$ for the Q5C mutein was 13 pg/ml, which is similar to the mean $IC_{50}$s of the wild type rIFN-α proteins. The mean $IC_{50}$ for the S163C protein was 27 pg/ml. These data are summarized in Table 4.

TABLE 4

Expression and in vitro Bioactivities of IFN-α2 Cysteine Muteins

| IFN-α2 Protein | Mutation Location | Relative Expression Total Cellular[1] | Percent Soluble[2] | Mean $IC_{50}$ (pg/ml) | $IC_{50}$ Range[3] (pg/ml) |
|---|---|---|---|---|---|
| rIFN-α2[4] | — | — | — | 16 +/− 7 | 8-29 (n = 10) |
| rIFN-α2[5] | — | ++++ | ~33 | 13 +/− 4 | 7-19 (n = 10) |
| C1S | N-terminal region[6] | +/− | 0 | | |
| Q5C | N-terminal region | ++++ | ~20 | 13 | 9, 11, 15, 18 |
| 43C44 | A-B loop | ++ | 0 | | |
| N45C | A-B loop | ++ | 0 | | |
| Q46C | A-B loop | +/− | 0 | | |
| F47C | A-B loop | ++++ | ~5 | | |
| Q48C | A-B loop | +/− | 0 | | |
| A50C | A-B loop | +/− | 0 | | |
| D77C | B-C loop | +/− | 0 | | |
| C98S | C-helix[7] | +++++ | ~5-10 | | |
| Q101C | C-D loop | +++++ | ~5-10 | | |
| T106C | C-D loop | +++++ | ~5-10 | | |
| E107C | C-D loop | +++++ | ~5-10 | | |
| T108C | C-D loop | +/− | 0 | | |
| S163C | C-terminal region | ++++ | ~33 | 27 +/− 8 | 18-40 (n = 6) |
| E165C | C-terminal region | +++ | ~20 | | |
| *166C | C-terminus | +++ | ~20 | | |

[1]Relative accumulation of the IFN-α2 protein in whole cell extracts
[2]Portion of the IFN-α2 protein in the osmotic shock supernatant, estimated from SDS-PAGE gels
[3]$IC_{50}$ values from individual experiments
[4]Commercial wild type rIFN-α2 (Endogen, Inc.)
[5]Wild type rIFN-α2 prepared by Bolder Biotechnology, Inc.
[6]Mutation creates a free cysteine (C98) in the C-helix
[7]Mutation creates a free cysteine (C1) in the N-terminal region

EXAMPLE 22

PEGylation, Purification and Bioactivity of PEG-Q5C and PEG-S163C

A. PEGylation of IFN-α Cysteine Muteins.

A small-scale PEGylation experiment was performed with the purified rIFN-α2 cysteine muteins to identify conditions that allowed the proteins to be monoPEGylated at the free cysteine residue. Over-reduction of the proteins was monitored by non-reducing SDS-PAGE, looking for a shift to a higher than expected apparent molecular weight as a result of protein unfolding, or for the appearance of multiple PEGylated species generated as the result of native disulfide reduction. Initial titration experiments were performed with the Q5C protein. One μg aliquots of purified Q5C were incubated with increasing concentrations of TCEP [Tris(2-carboxyethyl)phosphine]-HCl at room temperature in 100 mM Tris, pH 8.5 in the presence of varying amounts of excess 5 kDa maleimide-PEG. After 60 min, the reactions were stopped and immediately analyzed by non-reducing SDS-PAGE. The amounts of TCEP and PEG reagent that yielded significant amounts of monoPEGylated Q5C protein (molecular weight of approximately 28 kDa by non-reducing SDS-PAGE), without modifying wild type rIFN-α2, were used for further experiments. The titration experiments indicated that a 10-fold molar excess of TCEP and 20-fold excess of 5 kDa maleimide PEG gave around 60% monoPEGylated protein without detectable di or tri-PEGylated protein, or modification of wild type rIFN-α2.

These conditions also were used to PEGylate several other rIFN-α2 muteins. One μg aliquots of purified wild type and the rIFN-α2 muteins (Q5C, T106C, E107C, S163C) were incubated for 1 hour with a 10-fold molar excess TCEP and a 20-fold molar excess of 5 kDA maleimide PEG at pH 8.5 at room temperature. The four muteins were monoPEGylated to varying degrees (estimated to be from 30-60%) based on SDS-PAGE analysis of the reaction mixtures. Wild-type rIFN-α2 showed no detectable PEGylation under these conditions. Control experiments indicated that the Q5C, T106C, E107C and S163C cysteine muteins needed to be reduced with TCEP to be PEGylated. These data indicate that the PEG molecule is attached to the cysteine residue introduced into the Q5C, T106C, E107C and S163C proteins.

B. Preparation and Purification of PEG-Q5C IFN-α2 and PEG-S163C:

Larger quantities of the Q5C and S163 muteins were PEGylated so that biological activities of the PEGylated proteins could be measured. For the Q5C protein, the PEGylation conditions used for the small-scale experiments were scaled to 140 μg protein to give sufficient material for purification and characterization. The larger PEGylation reaction was performed for 1 hr at room temperature, diluted 10× with 20 mM MES, pH 5.0, adjusted to pH 3.0, and then loaded quickly onto an S-Sepharose column using conditions similar to those described for initial purification of the rIFN-α2 muteins. The presence of the PEG moiety decreased the protein's affinity for the resin, allowing the PEGylated protein to be separated from the non-PEGylated protein. The chromatogram from the S-Sepharose column showed two major protein peaks eluting at approximately 190 mM NaCl and 230 mM NaCl. The early eluting major peak (eluting at approximately 190 mM NaCl) was determined to be mono-PEGylated Q5C by SDS-PAGE. The apparent molecular weight of monoPEgylated Q5C is approximately 28 kDa by SDS-PAGE. The later eluting major peak (eluting at approximately 230 mM NaCl) was determined to be unreacted Q5C protein. Fractions from the early eluting peak containing predominantly PEG-Q5C, were pooled and used for bioactivity measurements.

The S163C cysteine mutant was PEGylated at a 90 μg scale and purified using protocols essentially identical to those described for PEG-Q5C.

C. Bioactivities of PEG-Q5C and PEG-S163C Cysteine Muteins:

Biological activity of the purified PEG-Q5C protein was measured in the Daudi cell assay described in Example 20. Concentration of the protein was determined using a Bradford dye binding assay. The PEG-Q5C protein showed a similar dose-response curve and reached the same level of maximal growth inhibition as wild type rIFN-α2 and the non-modified Q5C protein, within the error of the assay. The mean $IC_{50}$ for the PEG-Q5C mutein was ~22 pg/ml, which is within 2-fold of the $IC_{50}$ values determined for wild type IFN-α2 and the unmodified Q5C proteins analyzed on the same days (Table 5). Bioactivity of the PEG-Q5C protein is significantly greater than that of rIFN-α2 that has been PEGylated with non-specific, amine-reactive PEG reagents. The latter protein has an $IC_{50}$ of 164 pg/ml in the Daudi cell assay (Monkarsh et al., 1997). These data are summarized in Table 5.

Bioactivity experiments also were performed with the PEG-S163C protein. The PEG-S163C protein also was biologically active and inhibited Daudi cell proliferation to the same extent as wild type rIFN-α2, within the error of the assay. The average $IC_{50}$ for the PEG-S163C protein was about 42 pg/ml, which is better than the amine-Pegylated IFN-α

TABLE 5

Bioactivity of PEG-Q5C IFN-α

| IFN-α Protein | Mean $EC_{50}$ (pg/ml) | $EC_{50}$ Range[1] (pg/ml) | | |
|---|---|---|---|---|
| | | Exp A | Exp B | Exp C |
| Endogen rIFN-α | 13 | 9 | 11 | 20 |
| rIFN-α[2] | 12 | 10 | 10 | 16 |
| Q5C | 12 | 8.5 | 11 | 18 |
| PEG-Q5C | 22 | 18 | 18 | 30 |
| Amine-PEGylated-IFN-α[3] | 164 | — | — | — |

[1]Data from three experiments.
[2]rIFN-α2 prepared by Bolder Biotechnology, Inc.
[3]Data from Monkarsh et al. (1997)

EXAMPLE 23

In vivo efficacy of the PEGylated GH cysteine muteins can be tested in hypophysectomized (HYPDX) rats. This is a well-characterized model of GH deficiency (Cox et al., 1994; Clark et al., 1996). GH stimulates body weight gain and bone and cartilage growth in HYPDX rats (Cox et al., 1994; Clark et al., 1996). Hypophysectomized Sprague-Dawley rats can be purchased from a commercial supplier such as Charles River (Wilmington, Mass.). Typically, rats are hypophysectomized between 40 and 50 days of age and weigh approximately 120 g. Groups of 8 rats should receive subcutaneous injections of rhGH, PEG-Cys-GH or placebo (vehicle solution) at specified intervals and weight gain measured daily over a 10 day period. Rats should be weighed daily at the same time per day to eliminate possible variables associated with feeding. In addition to overall weight gain, bone growth (tibial epiphysis width) can be measured. At time of sacrifice, the right and left proximal tibial epiphyses can be removed and fixed in formalin. The fixed tibias can be split at the proximal end in a saggital plane, stained with silver nitrate and exposed to a strong light (Greenspan et al., 1949). The width of the cartilaginous epiphseal plate can be measured using a stereomicroscope equipped with a micrometer eyepiece. Ten measurements should be made for each epiphysis and the means+/−SEM for the combined values for the left and right tibias should be calculated. Comparisons between groups can be made using a Students T test for single comparisons and one-way analysis of variance for multiple comparisons. $P<0.05$ should be considered significant.

Efficacy of the GH cysteine muteins modified with 10 kDa or 20 kDa PEGS can be tested by administering the proteins to the rats daily, every other day, every third day, every fourth day or following a single injection. Five μg of non-PEGylated hGH administered twice a day (10 μg BID) by subcutaneous injection gives a strong growth response in the HYPDX rat model (Cox et al., 1994; Clark et al., 1996). In initial experiments different groups of rats should receive subcutaneous injections of 0.08, 0.4, 2, 10, or 50 μg of the PEGylated Cys-GH proteins/injection/rat. Control rats should receive vehicle solution only. Additional control groups should receive non-PEGylated rhGH (10 μg/BID) and 10 μg non-PEGylated hGH using the same dosing regimen as the PEGylated Cys-GH proteins. Administration of the PEGylated GH cysteine muteins to the HYPDX rats should result in an increase in body weight gain and tibial epyphysis width growth compared with the vehicle-treated group.

Efficacy of the PEGylated GH cysteine muteins also can be tested in rodent models of cachexia. Dexamethasone (DEX) can be administered to the rats to induce weight loss. Groups of normal Sprague-Dawley rats (200-225 g) should receive daily subcutaneous injections of dexamethasone (200 μg/rat; approximately 1 mg/kg). This amount of dexamethasone should induce a loss of approximately 5-6 g over an 8 d period. Vehicle or varying doses of the PEGylated GH cysteine muteins can be administered to the rats once, daily, every other day, every third day or every fourth day in different experiments. Different groups of rats should receive subcutaneous injections of 0.08, 0.4, 2, 10, or 50 μg of the PEGylated Cys-GH proteins/injection/rat. Additional controls should include a group of rats that will receive no DEX or injections, a group of rats that receives DEX and non-PEGylated rhGH (10 μg BID) and a group of rats that receives DEX and non-PEGylated rhGH (10 μg daily, every other day, every third day, or every fourth day, depending upon the experiment, i.e., frequency that the PEGylated GH cysteine mutein is administered). Animals should be weighed daily. Food and water consumption should be monitored daily. At time of sacrifice, internal organs should be weighed. Statistical analyses should be performed as described for the HYPDX rat studies. Animals treated with the PEGylated GH cysteine muteins should lose less weight than the vehicle-treated animals.

In vivo efficacy of the PEGylated EPO cysteine muteins can be measured in normal rats by demonstrating that the proteins stimulate increases in hemocrit and erythropoiesis compared to vehicle-treated animals. EPO stimulates a significant increase in hematocrit in rats when dosed on a daily basis (Matsumoto et al., 1990; Vaziri et al., 1994; Baldwin et al., 1998). Sprague-Dawley rats can be purchased from a commercial supplier such as Charles River (Wilmington, Mass.). Groups of 5 rats should receive subcutaneous injections of BV rEPO, PEGylated EPO cysteine mutein or placebo (vehicle solution) at specified intervals for up to five days. On day 6 the animals should be sacrificed and blood samples collected for hematocrit and complete blood cell count (CBC) analysis, which can be performed by a commercial laboratory. Hematopoietic tissues (liver and spleen) should be collected, weighed and fixed in formalin for histopathologic analyses to look for evidence of increased erythropoiesis. Bone marrow should be removed from various long bones and the sternum for unit particle preparations and histopathologic analysis to look for evidence of increased erythropoiesis. Comparisons between groups should be made using a Students T test for single comparisons and one-way analysis of variance for multiple comparisons. $P<0.05$ should be considered significant. The PEGylated EPO cysteine muteins should stimulate increases in hematocrit and erythropoiesis in the rats compared to the vehicle-injected animals. Efficacy of the PEGylated EPO cysteine muteins modified with 10 kDa or 20 kDa PEGS can be tested when administered once, every other day or every third day. 100 IU/kg (~800 ng/kg) of non-PEGylated EPO administered once per day (160 ng SID/200 g rat) by subcutaneous injection gives a significant increase in hematocrit (Matsumoto et al., 1990; Vaziri et al., 1994; Baldwin et al., 1998). In initial experiments different groups of rats should receive subcutaneous injections of 0.32, 1.6, 8, 40 or 160 ng of the PEGylated EPO cysteine muteins. Control rats should receive vehicle solution only. Additional control groups should receive non-PEGylated rEPO (160 ng/SID) and 160 ng non-PEGylated rEPO using the same dosing regimen as the PEGylated EPO cysteine muteins.

Efficacy of the PEGylated EPO muteins also can be tested in chemotherapy-induced anemia models. Cisplatin-induced anemia is a well-characterized rodent model of chemotherapy-induced anemia and has direct relevance to the human clinical setting. rEPO reverses the anemia in this model when administered at daily doses of 100 Units/kg (Matsumoto et al., 1990; Vaziri et al., 1994; Baldwin et al. 1998). Sprague-Dawley rats (~200 g) should be treated on day 0 with an intraperitoneal injection of Cisplatin (3.5 mg/kg) to induce anemia and randomized to various treatment groups. Efficacy of the PEGylated EPO cysteine muteins modified with 10 kDa or 20 kDa PEGS can be tested when administered once (on day 1), every other day or every third day. Different groups of rats should receive subcutaneous injections of 0.32, 1.6, 8, 40 or 160 ng/injection of the PEGylated EPO cysteine muteins. Rats should be injected with the test compounds for up to 8 days. One control group of rats should receive daily subcutaneous injections of rEPO (100 Units/kg). Another control group should not receive the initial Cisplatin injection but should receive injections of saline using the same dosing schedules used for the PEGylated EPO cysteine muteins. On day 9 the rats should be sacrificed and blood and tissue samples obtained for comprehensive CBC and histopathology analyses. The PEGylated EPO cysteine muteins should stimulate increases in hemocrit and erythropoiesis in the rats compared to the vehicle-injected control group.

IFN-α biological activity is relatively species-specific, which limits the range of preclinical animal models that can be studied. One model that can be used to measure in vivo efficacy of PEGylated IFN-α2 cysteine muteins is inhibition of human tumor xenograft growth in athymic nude mice. Human IFN-α2 is not active on mouse cells and inhibition of human tumor xenograft growth in nude mice occurs through a direct antiproliferative effect on the human tumor cells. IFN-α2 inhibits growth of a variety of primary human tumor xenografts and human tumor cell lines in athymic mice (Balkwill et al., 1985; Balkwill, 1986; Johns et al., 1992; Lindner and Borden, 1997). The primary endpoint for the studies should be tumor volume in treated mice. We expect to find that the administration of the PEGylated IFN-α2 cysteine muteins inhibits tumor growth (as measured by tumor volume) in the mice relative to vehicle-treated animals. Athymic nude mice can be purchased from a commercial vendor such as Charles River. Each mouse should be injected with $2 \times 10^6$ NIH-OVCAR-3 or MCF-7 tumor cells (the cell lines are available from the American Type Culture collection) on day 0 and randomly assigned to test groups, consisting of ten mice each. The tumor cells should be injected into the dermis overlying the mammary gland nearest the axillae. The different test groups should receive subcutaneous injections of varying doses of wild type rIFN-α2, 10 kDa-PEGylated IFN-α2 cysteine mutein, 20 kDa-PEGylated IFN-α2 cysteine mutein or placebo (vehicle solution) at specified intervals: every day (SID), every other day (EOD) or every third day (ETD). Tumor volumes should be determined at 4 day intervals by measuring the length and width of the tumors with calipers, as described by Linder and Borden (1997). At time of sacrifice, the tumors should be excised and weighed. Mean tumor volumes+/−SEM for each test group should be calculated for each sampling point. Comparisons between groups should be made using a Students T test for single comparisons and one-way analysis of variance for multiple comparisons. Five μg of non-PEGylated IFN-α2 administered once per day by subcutaneous injection inhibits growth of NIH-OVCAR-3 cells and MCF-7 cells in athymic mice by 80% after 6 weeks (Lindner and Borden, 1997). Either cell line can be used for these studies. The NIH-OVCAR-3 line (available from the ATCC) does not require estrogen for growth, as do the MCF-7 cells. Xenograft experiments with MCF-7 cells require that the mice be oophorectomized and implanted with estrogen pellets (Lindner and Borden, 1997). In initial experiments, different groups of mice should receive subcutaneous injections of 1 or 5 μg per injection of rIFN-α2, 10-kDa-PEGylated IFN-α2 cysteine mutein or 20-kDa-PEGylated IFN-α2 cysteine mutein using every day, every other day or every third day dosing schedules. Dosing should begin on day 2 following injection of the tumor cells into the mice. Control mice should receive vehicle solution only. In the every other day and every third day dosing experiments, an additional positive control group should receive daily subcutaneous injections of 5 μg unmodified rIFN-α2.

REFERENCES

Abdel-Meguid, S. S., Shieh, H-S., Smith W. W., Dayringer, H. E., Violand, B. N. and Bentle, L. A. (1987) Proc. Natl. Acad. Sci. USA 84: 6434-6437.

Abrahmsen, L., Moks, T., Nilsson, B. and Uhlen, M. (1986) Nucleic Acids Res. 14:7487-7500.

Abuchowski, A., Kazo, G. M., Verhoest, C. R., van Es, T., Kafkewitz, D., Nucci, M. L., Viau, A. T. and Davis, F. F. (1984) Cancer Biochem. Biophys. 7: 175-186.

Alt, F. W., Kellems, R. E., Bertino, J. R., and Schimke, R. T. (1978) J. Biol. Chem. 253:1357-1370.

Ayres, M. D., Howard, S. C., Kuzio, J., lopez-Ferber, M., and Possee, R. D. (1994) Virology 202:586-605.

Batik, S. (1993) in "Methods in Molecular Biology", White, B. A., ed. (Humana Press, Totawa, N.J.), 15: 277-286.

Bazan, F. (1991) Immunology Today 11: 350-354.

Bazan, J. F. (1992) Science 257: 410-411.

Becker, G. W. and Hsiung, H. M. (1986) FEBS Lett. 204: 145-150.

Bewley et al., (1969) Biochem. 8: 4701-4708.

Bill, R. M., Winter, P. C., McHale, C. M., Hodges, V. M., Elder, G. E., Caley, J., Flitsch, S. L., Bicknell, R. and Lappin, T. R. J. (1995) Biochem. Biophys. Acta 126: 35-43.

Blatt, L. M., Davis, J. M., Klein, S. B. and Taylor, M. W. (1996) J. Interferon and Cytokine Research 16: 489-499.

Boissel, J.-P., Lee, W.-R., Presnell, S. R., Cohen, F. E. and Bunn, H. F. (1993) J. Biol. Chem. 268:15983-15993.

Bollag, D. M., Rozycki, M. D. and Edelstein, S. J. (1996) Protein Methods, 415 pages, Wiley-Liss, NY, N.Y.

Braxton, S. M. (1998) U.S. Pat. No. 5,766,897.

Chamow & Ashkenazi (1996), Trends in biotech 14:52-60.

Chang, C. N., Rey, B., Bochner, B., Heyneker, H. and Gray, G. (1987) Gene: 189-196.

Cheah, K-C., Harrison, S., King, R., Crocker, L., Wells, J. R. E. and Robins, A. (1994) Gene, 138: 9-15.

Clark, R., Olson, K., Fuh, G., Marian, M., Mortensen, D., Teshima, G., Chang, S., Chu, H., Mukku, V., Canova-Davis, E., Somers, T., Cronin, M., Winkler, M. and Wells, J. A. (1996) J. Biol. Chem. 271: 21969-21977.

Cox, G. N. and McDermott, M. J. (1994) WO 9412219.

Cox, G. N., McDermott, M. J., Merkel, E., Stroh, C. A., Ko, S. C., Squires, C. H., Gleason, T. M. and Russell, D. (1994) Endocrinology 135: 1913-1920.

Cox, G. N. and Russell, D. (1994) WO 9,422,466.

Crouse, G. F., McEwan, R. N., and Pearson, M. L. (1983) Mol. Cell. Biol. 3:257-266.

Cunningham, B. C. and Wells, J. A. (1989) Science 244: 1081-1085.

Cunningham, B. C., Jhurani, P., Ng, P. and Wells, J. A. (1989) Science 243: 1330-1336.

Cunningham, B. C., Ultsch, M., de Vos, A. M., Mulkerrin, M. G., Clauser, K. R. and Wells, J. A. (1991) Science 254: 821-825.

Daopin, S., Piez, K. A., Ogawa, Y., and Davies, D. R. (1992) Science 257: 369-373.

Davis, S., Aldrich, T. H., Stahl, N., Pan, L., Taga, T., Kishimoto, T., Ip, N. Y. and Yancopoulus, G. D. (1993) Science 260: 1805-1808.

Davies, A. H. (1995) Curr. Opin. Biotechnol. 6:543-547.

DeChiara, T. M., Erlitz, F. and Tarnowski, k, S. J. (1986) Methods Enzymology, 119: 403-15.

de la Llosa, P., Chene, N. and Martal, J. (1985) FEBS Letts. 191: 211-215.

Denefle, P., Kovarik, S., Ciora, T. Gosselet, M., Benichou, J.-C., Latta, M. Guinet, F., Ryter, A. and Mayaux, J.-F. (1989) Gene 85, 499-510.

de Vos, A. M., Ultsch, M. and Kossiakoff, A. A. (1992) Science 255: 306-312.

Diederichs, K., Boone, T. and Karplus, A. (1991) Science 154: 1779-1782.

Evinger, M. and Pestka, S. (1981) Methods Enzymol. 79:362-368.

Fuh, G., Cunningham, B. C., Fukunaga, R., Nagata, S., Goeddel, D. V. and Wells, J. A. (1992) Science 256: 1677-1680.

Fujimoto, K., Fukuda., T., and Marumoto., R. (1988) J. Biotechnol. 8:77-86.

Geisse, S., Gram, H., Kleuser, B. and Kocher, H. P. (1996) Prot. Express. Purif. 8:271-282.

Goeddel, D. V., Heyneker, H. L., Hozumi, T., Arentzen, R., Itakura, K., Yansura, D. G., Ross, M. J., Miozzari, G., Crea, R. and Seeburg, P. H. (1979) Nature 281: 544-548.

Goodson, R. J. and Katre, N. V. (1990) Biotechnology 8: 343-346.

Greenspan, F. S., Li., C. H., Simpson, M. E. and Evans, H. M. (1949) Endocrinology 45:455-463.

Ghrayeb, J., Kimura, H., Takahara, M., Hsiung, H., Masui, Y. and Inouye, M. (1984) EMBO J. 3:2437-2442.

Hannum, C., Culpepper, J., Campbell, D., McClanahan, T., Zurawski, S. et al. (1994) Nature 368: 643-648

Hershfield, M. S., Buckley, R. H., Greenberg, M. L. et al., (1987) N. Engl. J. Medicine 316: 589-596.

Hill, C. P., Osslund, T. D. and Eisenberg, D. (1993) Proc. Natl. Acad. Sci. USA 90:5167-5171.

Horisberger, M. A. and Di Marco, S. (1995) Pharmac. Ther. 66: 507-534.

Horoszewicz, J. S., Leong, S. S, and Carter, W. A. (1979) Science 206:1091-1093.

Horton, R. M. (1993) in "Methods in Molecular Biology", White, B. A., ed. (Humana Press. Totawa, N.J.), v.15, 214-250.

Hsiung, H. M., Mayne, N. G. and Becker, G. W. (1986) Biotechnology 4: 991-995.

Imai, N., Kawamura, A., Higuchi, M., Oh-eda, M., Orita, T., Kawaguchi, T., and Ochi, N. (1990) J. Biochem. 107:352-359.

Innis, M. A., Gelfand, D. H, Sninsky, J. J. and White, T. J. eds. (1998) "PCR Protocols: A Guide to Methods and Applications" (Academic Press, San Diego, Calif.).

Jacobs, K., Shoemaker, C., Rudersdorf, R., Neill, S. D., Kaufman, R. J., Mufson, A., Seehra, J., Jones, S. S., Hewick, R., Fritsch, E. F., Kawakita, M., Shimizu, T. and Miyake, T. (1985) Nature 313: 806-810.

Johnson, D. L., Middleton, S. A., McMahon, F. Barbone, F. P., Kroon, D., Tsao, E., Lee, W. H., Mulcahy, L. S, and Jolliffe, L. K. (1996) Protein Expression Purif. 7:104-113.

Kadonaga, J., Gautier, A. Straus, D. R., Charles, A. D., Edge, M. D. and Knowles, J. R. (1984) J. Biol. Chem. 259: 2149-2154.

Khan, F. R. and Rai, V. R. (1990) Bioprocess Technology 7:161-169.

Karasiewicz, R., Nalin, C. and Rosen, P. (1995) U.S. Pat. No. 5,382,657.

Katre, N. V. (1990) J. Immunology 144: 209-213.

Katre, N. V., Knauf, M. J. and Laird, W. J. (1987) Proc. Natl. Acad. Sci. USA 84: 1487, 1491.

Kaufman, R. J. (1990) Meth. Enzymol. 185:537-566.

Kingsley, D. M. (1994) Genes Dev. 8: 133-146.

Kinstler, O. B., Gabriel, N. E., Farrar, C. E. and DePrince, R. B. (1996) International Patent Application Number WO 96/11953.

Knauf, M. J., Bell, D. P., Hirtzer, P., Luo, Z.-P., Young, P. D. and Katre, N. V. (1988) J. Biol. Chem. 263: 15064-15070.

Komatsu, N., Nakauchi, H., Miwa, A., Ishihara, T., Eguchi, M., Moroi, M., Okada, M., Sato, Y., Wada, H., Yawata, Y., et al., (1991) Cancer Research 51: 341-348.

Koshland, D. and Botstein, D. (1980) Cell 20: 749-760.

Kutty G., Kutty, R. K., Samuel, W., Duncan, T., Jaworski, C., and Wiggert, B. (1998) Biochem. Biophys. Res. Commun. 246: 644-649.

Lawton, L. N., Bonaldo, M. F., Jelenc, P. C., Qiu, L., Baumes, S. A., Marcelino, R. A., de Jesus, G. M., Wellington, S., Knowles, J. A., Warburton, D., Brown, S., and Soares, M. B. (1997) Gene 203: 17-26.

Li, C. H. (1982) Mol. Cell. Biochem. 46: 31-41.

Lin, F.-K., Suggs, S., Lin, C.-H., Browne, J. K., Smalling, R., Egrie, J. C., Chen, K. K., Fox, G. M., Martin, F., Stabinsky, Z., Badrawi, S. M., Lai, P.-H. and Goldwasser, E. Proc. Natl. Acad. Sci. USA 82: 7580-7584.

Lu, H. S., Boone, T. C., Souza, L. M., and Lai, P. H. (1989) Arch. Biochem. Biophys. 268: 81-92.

Lucas, B. K., Giere, L. M., DeMarco, M. A., Shen, A., Chisolm, V., and Crowley, C. W. (1996) Nucleic Acids Res. 24:1774-1779.

Lydon, N. B., Favre, C., Bove, S., Neyret, O., Benureau, S., Levine, A. M., Seelig, G. F., Nagabhushan, T. L. and Trotta, P. P. (1985) Biochemistry 24: 4131-4141.

MacGillivray, M. H., Baptista, J. and Johnson, A. (1996) J. Clin. Endocrinol. Metab. 81: 1806-1809.

Maisano, F., Testori, S. A., and Grandi, G. (1989) J. Chromatograph. 472: 422-427.

Mark, D. F., Lin, L. S, and Lu, S-D. Y. (1985) U.S. Pat. No. 4,518,584.

Mark, D. F., Lu, S. d., Creasey, A. a., Yamamoto, R. and Lin, L. S. (1984) Proc. Natl. Acad. Sci. USA 81: 5662-5666.

Martal, J., Chene, N. and de la Llosa, P. (1985) FEBS. Letts. 180: 295-299.

Martin, F. H., Suggs, S. V., Langley, K. E., Lu, H. S., Ting, J., Okino, K. H., Morris, F. C., McNiece, I. K., Jacobsen, F. W., Mendiaz, E. A., Birkett, N. C. et al., (1990) Cell 63: 203-211.

Massague, J. (1990) Annu. Rev. Cell Biol. 6: 597-641.

Matthews, D. J., Topping, R. S., Cass, R. T. and Giebel, L. B. (1996) Proc. Natl. Acad. Sci. USA 93: 9471-9476.

McDonald, N. Q. and Hendrickson, W. A. (1993) Cell 73: 421-424.

McKay, D. B. (1992) Science 257: 412.

Meyers, F. J., Paradise, C., Scudder, S. A., Goodman, G. and Konrad, M. (1991) Clin. Pharmacol. Ther. 49: 307-313.

Milburn, M. V., Hassell, A. M., Lambert, M. H., Jordan, S. R., Proudfoot, A. E., Graber, P. and Wells, T. N. C. (1993) Nature 363: 172-176.

Mills, J. B., Kostyo, J. L., Reagan, C. R., Wagner, S. A., Moseley, M. H. and Wilhelm, A. E. (1980) Endocrinology 107: 391-399.

Mockridge, J. W., Aston, R., Morrell, D. J. and Holder, A. T. (1998) Eur. J. Endocrin. 138: 449-459.

Monkarsh, S. P., Ma, Y., Aglione, A., Bailon, P. et al. (1997) Anal. Biochem. 247: 434-440.

Mordenti, J., Chen, S. A., Moore, J. A., Ferrailo, B. L. and Green, J. D. (1991) Pharmacol. Res. 8:1351-1359.

Morehead, H., Johnson, P. D. and Wetzel, R. (1984) Biochemistry 23: 2500-2507.

Morioka-Fujimoto, K., Marumoto, R. and Fukuda, T. (1991) J. Biol. Chem. 266: 1728-1732.

Mott, H. R. and Campbell, I. D. (1995) Current Opinion in Structural Biology 5: 114-121.

Ostermeier, M., De Sutter., K., Georgiou, G. (1996) J. Biol. Chem. 271: 10616-10622.

Paonessa, G., Graziani, R., de Serio, A., Savino, R., Ciapponi, L., Lahm, A., Ssalvati, A. L., Toniatti, C. and Ciliberto, G. (1995) EMBO J. 14: 1942-1951.

Paul, W. E. ed. (1989) "Fundamental Immunology" (Raven Press, New York, N.Y.).

Pestka, S., Langer, J. A., Zoon, K. C. and Samuel, C. E. (1987) Ann. Rev. Biochem. 56: 727-777.

Picken, R. N., Mazaitis, A. J., Maas, W. K., Rey, M. and Heyneker, H. (1983) Infect. and Immun. 42: 269-275.

Powers, R., Garrett, D. S., March, C. J., Frieden, E. A., Gronenborn, A. M. and Clore, G. M. (1992) Science 256: 1673-1677.

Ranjan, A. and Hasnain, S. E. (1995) Virus Genes 2:149-153.

Redfield, C., Smith L. J., Boyd, J., Lawrence, G. M. P., Edwards, R. G., Smith, R. A. G., and Dobson, C. M. (1991) Biochemistry 30: 11029-11035.

Roitt, I. M., Brostoff, J., and Male, D. K. eds. (1989) "Immumology" (Gower Medical Publishers, New York, N.Y. and London, UK)

Rowlinson, S. W. Barnard, R., Bastiras, S., Robins, A. J., Brinkworth, R. and Waters, M. J. (1995) J. Biol. Chem. 270: 16833-16839.

Shaw, G., Veldman., G. and Wooters, J. L. (1992) U.S. Pat. No. 5,166,322.

Sytkowski, A. J., Lunn, E. D., Davis, K. L., Feldman, L. and Siekman, S. (1998) Proc. Natl. Acad. Sci. USA 95: 1184-1188.

Tanaka, H., Satake-Ishikawa, R., Ishikawa, M., Matsuki, S, and Asano, K. (1991) Cancer Research 51: 3710-3714.

Teh, L.-C. and Chapman, G. E. (1988) Biochem. Biophys. Res. Comm. 150: 391-398.

Thompson, S. A. (1992) J. Biol. Chem. 267: 2269-2273.

Trill, J. J., Shatzman, A. R., and Ganguly, S. (1995) Curr. Opin. Biotechnol. 6:553-560.

Tuma, R., Rosendahl, M. and Thomas, G. (1995) Biochem. 34: 15150-15156.

Urlaub, G. and Chasin, L. A. (1980) Proc. Natl. Acad. Sci. USA 77:4216-4220.

Van Den Berg, C. L., Stroh, C., Hilsenbeck, S. G., Weng, C.-N., McDermott, M. J., Cox, G. N. and Yee, D. (1997) Eur. J. Cancer 33: 1108-1113.

Voss, T., Falkner, E., Ahorn, H. Krystek, E. Maurer-Fogy, I. Bodo, G., Hauptmann, R. (1994) Biochem. J. 298, 719-725.

Walter, M. R., Cook, W. J., Ealick, S. E., Nagabhusan, T. L., Trotta, P. T. and Bugg, C. E. (1992) J. Mol. Biol. 224: 1075-1085.

Wang, G. L. and Semenza, G. L. (1993) Blood 82:3610-3615.

White, B. A. (1993) in Methods in Molecular Biology, Vol. 15: PCR Protocols: Current Methods and Applications edited by Humana Press, Inc., Totowa, N.J.

Wojchowski, D. M., Orkin, S. H. and Sytkowski, A. J. (1987) Biochim. Biophys. Acta 910: 224-232.

Wrighton, N. C., Farrell, F. X., Chang, R. et al., (1996) Science 273: 458-463.

Yamaoka, T., Tabata, Y. and Ikada, Y. (1994) J. Pharm. Sci. 83: 601-606.
Baldwin, M. D., Zhou, X. J., Ing, T. S, and Vaziri, N. D. (1998) ASAIO J. 44: 44-47.
Balkwill, F. R., Goldstein, L. and Stebbing, N. (1985) Int. J. Cancer 35: 613-617.
Balkwill, F. R. (1986) Methods Enzymology 119: 649-657.
Cecil, R. and McPhee, J. R. (1959). Advances in Protein Chemistry 14, 255-389.
Cox, G. N., McDermott, M. J., Merkel, E., Stroh, C. A., Ko, S. C., Squires, C. H., Gleason, T. M. and Russell, D. (1994) Endocrinology 135: 1913-1920.
Greenspan, F. S., Li., C. H., Simpson, M. E. and Evans, H. M. (1949) Endocrinology 45: 455-463.
Johns, T. G., Mackay, I. R., Callister, K. A., Hertzog, P. J., Devenish, R. J. and Linnane, A. W. (1992) J. Natl. Cancer Institute 84: 1185-1190.
Lindner, D. J. and Borden, E. C. (1997) J. Interferon and Cytokine Research 17:681-693.
Matsumoto, T., Endoh, K., Kamisango, K., Akamatsu, K., Koizumi, K., Higuchi, M., Imai, N., Misui, H. and Kawaguchi, T. (1990) Br. J. Haematol. 75: 463-468.
Torchinskii, Y. M. (1971) in "Sulfhydryl and Disulfide Groups of Proteins" in Studies of Soviet Science (1971) Nauka Press, Moscow.
Trotta, P. B. (1986) Seminars in Oncology XIII Supplement 2: 3-12.
Vaziri, N. D., Zhou, X. J., and Liao, S. Y. (1994) Am. J. Physiol. 266: F360-366.

While various embodiments of the present invention have been described in detail, it is apparent that modifications and adaptations of those embodiments will occur to those skilled in the art. It is to be expressly understood, however, that such modifications and adaptations are within the scope of the present invention.

The invention claimed is:

1. A method for treating a condition treatable with growth hormone comprising administering to a patient in need thereof an effective amount of a cysteine variant of human growth hormone, wherein said cysteine variant comprises a cysteine residue substituted for an amino acid selected from the group consisting of amino acid P2, T3, P5, A34, K38, Q40, S43, S55, S57, A98, N99, S100, L101, V102, Y103, A105, S132, P133, R134, T135, Q137, K140, Q141, Y143, S144, D147, T148, N149, E186, and G187, or wherein a cysteine residue is added preceding the first F1 amino acid of human growth hormone or following the terminal F191 amino acid of human growth hormone, wherein the composition is administered to the patient by a route selected from the group consisting of intravenous administration, intraperitoneal administration, and subcutaneous administration.

2. The method of claim 1, wherein the cysteine variant is modified with a cysteine-reactive moiety.

3. The method of claim 1, wherein the cysteine variant is modified with polyethylene glycol.

4. The method of claim 1, wherein said growth hormone protein is a recombinant protein.

5. The method of claim 1, wherein the cysteine variant comprises a cysteine residue substituted for amino acid T3.

6. The method of claim 1, wherein the cysteine variant comprises a cysteine residue substituted for amino acid P133.

7. The method of claim 1, wherein the cysteine variant comprises a cysteine residue substituted for amino acid Y143.

8. The method of claim 1, wherein the cysteine variant comprises a cysteine residue substituted for amino acid P2.

9. The method of claim 1, wherein the cysteine variant comprises a cysteine residue substituted for amino acid R134.

10. The method of claim 1, wherein the cysteine variant comprises a cysteine residue substituted for amino acid L101.

11. The method of claim 1, wherein the cysteine variant comprises a cysteine residue substituted for amino acid V102.

12. The method of claim 1, wherein the cysteine variant comprises a cysteine residue substituted for amino acid Y103.

13. The method of claim 1, wherein the composition is administered by intravenous administration.

14. The method of claim 1, wherein the composition is administered by subcutaneous administration.

15. A method for treating a condition treatable with growth hormone comprising administering to a patient in need thereof an effective amount of a cysteine variant of human growth hormone, wherein said cysteine variant comprises a cysteine residue substituted for an amino acid selected from the group consisting of amino acid P2, T3, P5, A34, K38, Q40, S43, S55, S57, A98, N99, S100, L101, V102, Y103, A105, S132, P133, R134, T135, Q137, K140, Q141, Y143, S144, D147, T148, N149, E186, and G187, or wherein a cysteine residue is added preceding the first F1 amino acid of human growth hormone or following the terminal F191 amino acid of human growth hormone, wherein the condition treatable with growth hormone is selected from the group consisting of growth hormone deficiency, short stature resulting from growth hormone deficiency, short stature resulting from Turner's syndrome, short stature resulting from renal failure, and cachexia.

16. The method of claim 15, wherein the condition treatable with growth hormone is growth hormone deficiency.

17. The method of claim 15, wherein the condition treatable with growth hormone is short stature resulting from growth hormone deficiency.

18. The method of claim 15, wherein the condition treatable with growth hormone is short stature resulting from Turner's syndrome or renal failure.

19. The method of claim 15, wherein the condition treatable with growth hormone is cachexia.

20. The method of claim 15, wherein the cysteine variant is modified with a cysteine-reactive moiety.

21. The method of claim 15, wherein the cysteine variant is modified with polyethylene glycol.

22. The method of claim 15, wherein said growth hormone protein is a recombinant protein.

23. The method of claim 15, wherein the cysteine variant comprises a cysteine residue substituted for amino acid T3.

24. The method of claim 15, wherein the cysteine variant comprises a cysteine residue substituted for amino acid P133.

25. The method of claim 15, wherein the cysteine variant comprises a cysteine residue substituted for amino acid Y143.

26. The method of claim 15, wherein the cysteine variant comprises a cysteine residue substituted for amino acid P2.

27. The method of claim 15, wherein the cysteine variant comprises a cysteine residue substituted for amino acid R134.

28. The method of claim 15, wherein the cysteine variant comprises a cysteine residue substituted for amino acid L101.

29. The method of claim 15, wherein the cysteine variant comprises a cysteine residue substituted for amino acid V102.

30. The method of claim 15, wherein the cysteine variant comprises a cysteine residue substituted for amino acid Y103.

\* \* \* \* \*